(12) United States Patent
Wanders et al.

(10) Patent No.: US 10,705,008 B2
(45) Date of Patent: Jul. 7, 2020

(54) AUTOFOCUS SYSTEMS AND METHODS FOR PARTICLE ANALYSIS IN BLOOD SAMPLES

(71) Applicant: IRIS International, Inc., Chatsworth, CA (US)

(72) Inventors: Bart J. Wanders, Trabuco Canyon, CA (US); Brett Jordan, Los Angeles, CA (US); Gregory A. Farrell, Ridgewood, NJ (US); Thomas H. Adams, Encinitas, CA (US); Warren Groner, Great Neck, NY (US)

(73) Assignee: Iris International, Inc., Chatsworth, CA (US)

( * ) Notice: Subject to any disclaimer, the term of this patent is extended or adjusted under 35 U.S.C. 154(b) by 0 days.

(21) Appl. No.: 14/216,811

(22) Filed: Mar. 17, 2014

(65) Prior Publication Data

US 2014/0273068 A1    Sep. 18, 2014

Related U.S. Application Data

(60) Provisional application No. 61/799,152, filed on Mar. 15, 2013.

(51) Int. Cl.
*G01N 15/14*    (2006.01)
*G01N 21/00*    (2006.01)
(Continued)

(52) U.S. Cl.
CPC .......... *G01N 15/1404* (2013.01); *G01N 1/30* (2013.01); *G01N 15/06* (2013.01); *G01N 15/147* (2013.01);
(Continued)

(58) Field of Classification Search
CPC ............ G01N 15/1404; G01N 15/147; G01N 2015/0065; G01N 2015/1452;
(Continued)

(56) References Cited

U.S. PATENT DOCUMENTS 3,822,095 A    7/1974  Hirschfeld
4,338,024 A    7/1982  Bolz et al.
(Continued)

FOREIGN PATENT DOCUMENTS

CA    2349995 A1    12/2001
CN    1521497 A     8/2004
(Continued)

OTHER PUBLICATIONS

International Search Report and Written Opinion from PCT/US2014/030928 dated Jun. 18, 2014, 13 pages.
(Continued)

*Primary Examiner* — Dean Kwak
(74) *Attorney, Agent, or Firm* — Schwegman Lundberg & Woessner, P.A.

(57) ABSTRACT

Particles such as blood cells can be categorized and counted by a digital image processor. A digital microscope camera can be directed into a flowcell defining a symmetrically narrowing flowpath in which the sample stream flows in a ribbon flattened by flow and viscosity parameters between layers of sheath fluid. A contrast pattern for autofocusing is provided on the flowcell, for example at an edge of a rear illumination opening. The image processor assesses focus accuracy from pixel data contrast. A positioning motor moves the microscope and/or flowcell along the optical axis for autofocusing on the contrast pattern target. The processor then displaces microscope and flowcell by a known distance between the contrast pattern and the sample stream, thus focusing on the sample stream. Blood cell images are (Continued)

collected from that position until autofocus is reinitiated, periodically, by input signal, or when detecting temperature changes or focus inaccuracy in the image data.

14 Claims, 26 Drawing Sheets

(51) Int. Cl.
| | |
|---|---|
| G01N 1/30 | (2006.01) |
| G01N 15/06 | (2006.01) |
| G01N 21/53 | (2006.01) |
| G01N 33/49 | (2006.01) |
| G01N 33/50 | (2006.01) |
| G01N 33/80 | (2006.01) |
| G01N 21/05 | (2006.01) |
| G01N 15/00 | (2006.01) |
| G01N 15/10 | (2006.01) |

(52) U.S. Cl.
CPC ..... *G01N 15/1434* (2013.01); *G01N 15/1463* (2013.01); *G01N 15/1468* (2013.01); *G01N 15/1475* (2013.01); *G01N 21/53* (2013.01); *G01N 33/49* (2013.01); *G01N 33/4915* (2013.01); *G01N 33/5091* (2013.01); *G01N 33/5094* (2013.01); *G01N 33/80* (2013.01); G01N 2015/0065 (2013.01); G01N 2015/1037 (2013.01); G01N 2015/1411 (2013.01); G01N 2015/1413 (2013.01); G01N 2015/1452 (2013.01); G01N 2015/1486 (2013.01); G01N 2021/058 (2013.01)

(58) Field of Classification Search
CPC ........... G01N 15/1434; G01N 15/1463; G01N 15/1475; G01N 2015/1037; G01N 2015/1411; G01N 2015/1413; G01N 2015/1486; G01N 33/5094; G01N 2021/058
USPC ..................... 422/73, 82.05; 436/10; 702/21; 356/338, 391, 621; 435/4, 7.21; 382/134, 254, 255, 256
See application file for complete search history.

(56) References Cited

U.S. PATENT DOCUMENTS

| | | | |
|---|---|---|---|
| 4,428,669 A | 1/1984 | Bessis | |
| 4,732,479 A | 3/1988 | Tanaka et al. | |
| 5,083,014 A | 1/1992 | Kosaka | |
| 5,159,403 A | 10/1992 | Kosaka | |
| 5,457,526 A | 10/1995 | Kosaka | |
| 5,619,032 A | 4/1997 | Kasdan | |
| 5,633,503 A | 5/1997 | Kosaka | |
| 5,812,419 A * | 9/1998 | Chupp et al. | 702/20 |
| 5,822,447 A | 10/1998 | Kasdan | |
| 5,872,627 A * | 2/1999 | Miers | G01N 15/1431 356/338 |
| 5,880,835 A | 3/1999 | Yamazaki et al. | |
| 5,889,881 A * | 3/1999 | MacAulay | G01N 15/1475 382/133 |
| 6,130,745 A | 10/2000 | Manian et al. | |
| 6,184,978 B1 | 2/2001 | Kasdan et al. | |
| 6,424,415 B1 | 7/2002 | Kasdan et al. | |
| 6,441,894 B1 | 8/2002 | Manian et al. | |
| 6,590,646 B2 | 7/2003 | Kasdan et al. | |
| 7,041,952 B2 | 5/2006 | Iffland et al. | |
| 7,071,451 B2 | 7/2006 | Ishikawa et al. | |
| 7,486,329 B2 | 2/2009 | Endo | |
| 7,825,360 B2 | 11/2010 | Karasawa et al. | |
| 7,855,831 B2 | 12/2010 | Wolleschensky et al. | |
| 8,174,686 B2 | 5/2012 | Namba et al. | |
| 8,362,409 B2 | 1/2013 | Cooper et al. | |
| 2002/0028471 A1* | 3/2002 | Oberhardt | G01N 15/147 435/7.21 |
| 2004/0169867 A1* | 9/2004 | Sharpe | G01N 15/14 356/621 |
| 2006/0148028 A1 | 7/2006 | Noda et al. | |
| 2008/0138852 A1 | 6/2008 | Winkleman et al. | |
| 2008/0283722 A1 | 11/2008 | Uchiyama et al. | |
| 2009/0011430 A1 | 1/2009 | Ateya et al. | |
| 2009/0269799 A1 | 10/2009 | Winkleman et al. | |
| 2010/0111768 A1* | 5/2010 | Banerjee | C12Q 1/6869 422/82.08 |
| 2010/0178666 A1 | 7/2010 | Leshansky et al. | |
| 2010/0284602 A1 | 11/2010 | Winkleman et al. | |
| 2011/0014645 A1 | 1/2011 | Winkleman et al. | |
| 2011/0070606 A1 | 3/2011 | Winkleman et al. | |
| 2011/0128545 A1* | 6/2011 | Cox | G01N 35/00069 356/417 |
| 2011/0222051 A1* | 9/2011 | Heng | G01N 15/147 356/73 |
| 2012/0035061 A1 | 2/2012 | Bransky et al. | |
| 2013/0070249 A1 | 3/2013 | Choi et al. | |
| 2014/0193892 A1* | 7/2014 | Mohan | G01N 21/05 435/287.2 |

FOREIGN PATENT DOCUMENTS

| | | |
|---|---|---|
| CN | 101065656 A | 10/2007 |
| CN | 101536016 A | 9/2009 |
| EP | 0 286 088 A2 | 10/1988 |
| EP | 0 468 100 | 1/1992 |
| EP | 0 486 747 | 5/1992 |
| EP | 0 556 971 A2 | 8/1993 |
| EP | 1264205 A2 | 12/2002 |
| EP | 1761817 A1 | 3/2007 |
| EP | 2028264 A1 | 2/2009 |
| EP | 2030062 A1 | 3/2009 |
| GB | 1 471 976 A | 4/1977 |
| GB | 1 557 691 A | 12/1979 |
| GB | 2 121 976 A | 1/1984 |
| JP | 05296915 A | 11/1993 |
| JP | H06281557 A | 10/1994 |
| JP | 2003/005088 A | 1/2003 |
| JP | 2004188042 A | 7/2004 |
| JP | 2009089753 A | 4/2009 |
| WO | 99/05504 A2 | 2/1999 |
| WO | 2001/048455 A2 | 2/2001 |
| WO | 01/048455 | 5/2001 |
| WO | 01/48455 A2 | 7/2001 |
| WO | 2004-022774 A1 | 3/2004 |

OTHER PUBLICATIONS

International Search Report and Written Opinion for Application No. PCT/US2014/030942 dated Oct. 14, 2014, 31 pages.

Cubaud et al, "High-viscosity fluid threads in weakly diffusive microfluidic systems," New Journal of Physics, Jul. 31, 2009, p. 75029, vol. 11, No. 7, Institute of Physics Publishing, GB.

Kachel et al, Uniform Lateral Orientation, Cause by Flow Forces, of Flat Particles in Flow-Through Systems, Journal of Histochemistry and Cytochemistry, Jan. 1, 1977, pp. 774-780, vol. 25, No. 7, Histochemical Society, New York, NY, US.

Zhigang et al, "Rapid Mixing Using Two-Phase Hydraulic Focusing in Microchannels", Biomedical Devices, Mar. 1, 2005, pp. 13-20, vol. 7, No. 1, Kluwer Academic Publishers, BO.

JP Application No. 2016-502591 received an office action dated Jan. 5, 2018, 10 Pages.

JP2016-502591 received an Office Action dated Aug. 27, 2018 7 pages.

"Korean Application Serial No. 10-2015-7024439, Response filed Aug. 29, 2019 to Notice of Preliminary Rejection dated Jul. 16, 2019", w/ English claims, 15 pgs.

"Korean Application Serial No. 10-2015-7024466, Notice of Preliminary Rejection dated Jul. 17, 2019", w/ English Translation, 13 pgs.

(56) References Cited

OTHER PUBLICATIONS

"European Application Serial No. 14718878.3, Communication Pursuant to Article 94(3) EPC dated Oct. 8, 2019", 2 pgs.
"Koean Application Serial No. 10-2015-7024466, Response filed Sep. 17, 2019 to Notice of Preliminary Rejection dated Jul. 17, 2019", w/ English claims, 20 pgs.
"European Application Serial No. 14722049.5, Communication Pursuant to Article 94(3) EPC dated Oct. 18, 2019", 8 pgs.
"European Application Serial No. 18202980.1, Examiner Interview Summary dated Oct. 18, 2019", 5 pgs.
"European Application Serial No. 18213038.5, Response filed Nov. 14, 2019 to Extended European Search Report dated Apr. 30, 2019", 37 pgs.
"Korean Application Serial No. 10-2015-7024466, Final Office action dated Oct. 30, 2019", w/ English Translation, 5 pgs.

\* cited by examiner

AUTOFOCUS SYSTEMS AND METHODS FOR PARTICLE ANALYSIS IN BLOOD SAMPLES

CROSS-REFERENCES TO RELATED APPLICATIONS

This application is a non-provisional of, and claims the benefit of priority to, U.S. Provisional Patent Application No. 61/799,152 filed Mar. 15, 2013, the content of which is incorporated herein by reference. This application is also related to U.S. patent application Ser. Nos. 14/215,834, 14/216,533, 14/216,339, and 14/217,034, and International Patent Application Nos. PCT/US14/30850, PCT/US14/30902, and PCT/US14/30851, all filed Mar. 17, 2014. The content of each of these filings is incorporated herein by reference.

BACKGROUND OF THE INVENTION

This disclosure relates to the field of apparatus, systems, compositions, and methods for analysis of particles, including imaging of particles in fluid samples, using wholly or partly automated devices to discriminate and quantify particles such as blood cells in the sample. The present disclosure also relates to a particle and/or intracellular organelle alignment liquid (PIOAL) useful for analyzing particles in a sample from a subject, methods for producing the liquid, and methods for using the liquid to detect and analyze particles. Compositions, systems, devices and methods useful for conducting image-based biological fluid sample analysis are also disclosed. The compositions, systems, devices, and methods of the present disclosure are also useful for detecting, counting and characterizing particles in biological fluids such as red blood cells, reticulocytes, nucleated red blood cells, platelets, and for image and morphologically-based white blood cell differential counting, categorization, subcategorization, characterization and/or analysis.

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PLTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

Although such currently known particle analysis systems and methods, along with related medical diagnostic techniques, can provide real benefits to doctors, clinicians, and patients, still further improvements are desirable. Embodiments of the present invention provide solutions for at least some of these outstanding needs.

BRIEF SUMMARY OF THE INVENTION

Embodiments of the present invention encompass certain focusing techniques that allow hematology systems and methods to produce high quality images of particles that are present in fluid blood samples. Such high quality images provide the foundation for achieving high levels of discrimination which are useful to accurately classify cells allows for the use of optical systems having a high magnification and high numerical aperture objective. Exemplary optical alignment or focusing techniques facilitate the production of images with high level of resolution, with a short depth of field that corresponds to a thin ribbon of fluid sample which carries the particles.

In some cases, hematology systems may be re-focused on a regular basis to adjust for changes in local temperature and other factors. For example, autofocus techniques as discussed herein can compensate for thermal expansion or other factors present in a hematology analyzer which change the distance between an imaging objective and a flowcell and therefore negatively impact imaging results, for example by producing an image which is out of focus. Embodiments of the present invention also encompass autofocus systems and methods for hematology instruments that involve automatically focusing an imaging system without the need for a focusing liquid or solution or other user intervention. For example, exemplary autofocus techniques can involve obtaining an initial focus on a target fixed relative to the flowcell, rather than using techniques that are based on maximizing the contrast of the subject itself that appears in the image.

Certain embodiments of the present invention are based at least in part on the observation that the stream position within the flowcell does not change in response to temperature fluctuations, and may involve focusing on a target somewhere in the flowcell and then using a fixed offset to achieve good focus on the sample stream. Such approaches can be implemented without the use of a focusing solution that is flowed through the flowcell, and can be performed automatically and totally transparently to the user.

According to some embodiments, this disclosure relates to a visual analyzer for imaging a sample comprising particles suspended in a liquid, in which the apparatus includes a flowcell coupled to a source of the sample and to a source of a PIOAL, wherein the flowcell defines an internal flowpath, the flowcell being configured to direct a flow of a ribbon-shaped sample stream enveloped with the PIOAL through a viewing zone in the flowcell. An objective lens associated with a high optical resolution imaging device is disposed on an optical axis that intersects the ribbon-shaped sample stream. The relative distance between the objective and the flowcell is variable by operation of a motor drive coupled to a controller, for resolving and collecting a digitized image on a photosensor array. An autofocus pattern or imaging target is provided at a position fixed relative to the flowcell, the autofocus pattern being located at a predetermined distance from the plane of the prepared ribbon-shaped sample stream. A light source illuminates the ribbon-shaped sample stream and the autofocus pattern. At least one digital processor is associated with the controller coupled to operate the motor drive. The processor is also arranged to analyze the digitized image. The processor determines a focus position of the autofocus pattern to generate a focused image and then relatively displaces the objective and the flowcell over the predetermined distance (e.g. a displacement distance) from the focused position, to focus the high optical resolution imaging device on the ribbon-shaped sample stream.

In one aspect, embodiments of the present invention encompass methods for imaging particles in a blood fluid sample using a particle analysis system. The particle analysis system can be configured for geometric hydrofocusing. In some cases, the system can be configured for combined viscosity and geometric hydrofocusing. In some cases, the particles can be included in a blood fluid sample having a sample fluid viscosity. Exemplary methods can include flowing a sheath fluid along a flowpath of a flowcell of the particle analysis system. In some cases, the sheath fluid can have a sheath fluid viscosity that differs from the sample fluid viscosity by a viscosity difference in a predetermined viscosity difference range. Methods can also include injecting the blood fluid sample into the flowing sheath fluid within the flowcell so that the blood fluid sample fluid flows in a sample flowstream with a flowstream width greater than a flowstream thickness, the sample flowstream flowing through a decrease in flowpath size and traversing an imaging axis. Further, methods can include focusing an image capture device by imaging an imaging target having a position fixed relative to the flowcell. What is more, methods can include acquiring a focused image of the particles, suitable for particle characterization and counting, within the flowstream with the image capture device, where the image capture device is focused on the sample flowstream using a displacement distance. According to some embodiments, a viscosity difference between the sheath fluid and blood fluid sample, in combination with the decrease in flowpath size, is effective to hydrofocus the sample flowstream at the imaging axis while a viscosity agent in the sheath fluid retains viability of cells in the sample flowstream leaving structure and content of the cells intact when the cells extend from the sample flowstream into the flowing sheath fluid. In some cases, the sample flowstream has a thickness at the imaging axis within a range from about 2 μm to about 10 μm. In some cases, the flowpath has a thickness of about 150 μm at the imaging axis. In some cases, the imaging target is located on a viewport window disposed between the sample flowstream and the image capture device. In some cases, the imaging target is located on an illumination window, and the sample flowstream is disposed between the illumination window and the image capture device. In some cases, the displacement distance is zero. In some cases, the imaging target is located between an illumination window and a viewport window. In some cases, in the acquiring step, the image capture device is focused on the on the sample flowstream by adjusting a focal distance of the image capture device based on the displacement distance.

According to some embodiments, the process of acquiring the focused image includes adjusting a distance between the image capture device and the flowcell using the displacement distance. In some cases, adjusting the distance between the image capture device and the flowcell includes moving a component of the image capture device. The component of the image capture device can be a zoom lens, a mirror of the image capture device, or an assembly that includes the image capture device. In some cases, adjusting the distance between the image capture device and the flowcell includes moving the flowcell. In some cases, adjusting the distance between the image capture device and the flowcell includes moving at least an optical element of the image capture device and the flowcell. In some cases, the displacement distance is a distance along the imaging axis between the imaging target and the sample flowstream. In some cases, displacement distance is a distance difference between a first focal distance between the image capture device and the target and a second focal distance between the image capture device and the sample flowstream. In some cases, methods include an autofocusing step that involves injecting a test fluid sample into the sheath fluid to form a test sample flowstream within the flow cell, obtaining a first focused image of the imaging target using the image capture device, such that the focused imaging target and the image capture device define a first focal distance, obtaining a second focused image of the test sample flowstream using the image capture device, such that the focused test sample flow stream and the image capture device defining a second focal distance, and obtaining the displacement distance by calculating a difference between the first focal distance and the second focal distance. In some cases, the test fluid sample is the same blood fluid sample and the test sample flowstream is the same as the sample flowstream. In some cases, the autofocusing step establishes a focal plane associated with the image capture device, and the focal plane remains stationary relative to the image capture device. In some cases, the image capture device is focused on the sample flowstream using a temperature such as a sample fluid temperature, a sheath fluid temperature, a flowcell temperature, or an image capture device temperature. In some cases, the image capture device can be focused on the sample flowstream using a temperature, such as a flowcell temperature at the imaging site, a flowcell temperature at a location upstream of the imaging site, and a flowcell temperature at a location downstream of the imaging site. In some cases, the image capture device can be focused on the sample flowstream using a temperature rate of change, such as a sample fluid temperature rate of change, a sheath fluid temperature rate of change, a flowcell temperature rate of change, or an image capture device temperature rate of change.

According to some embodiments, methods may include detecting an autofocus re-initiation signal, and repeating autofocusing and image acquisition steps in response to the autofocus re-initiation signal. In some cases, the autofocus re-initiation signal includes or is based on a change in temperature, a decrease in focus quality, a lapsed time interval, or a user-input. In some cases, the focusing of the image capture device on the sample flowstream is performed independently of a temperature of the image capture device. In some cases, the imaging target includes a scale for use in positioning the imaging axis of the image capture device relative to the sample flowstream. In some cases, the imaging target includes an iris aligned relative to the imaging axis, such that the imaged particles are disposed within an aperture defined by the iris, and one or more edge portions of the iris are imaged during autofocusing. In some cases, the image capture device is focused on the sample flowstream by implementing axial rotation of the image capture device about the imaging axis, axial rotation of the flowcell about an axis extending along the imaging axis and within the field of view of the imaging device, tip rotation of the image capture device about an axis extending along the flowpath, tip rotation of the flowcell about an axis extending along and within the flowpath, tilt rotation of the image capture device about an axis traversing the flowpath and the imaging axis, and/or tilt rotation of the flowcell about an axis traversing the flowpath and the imaging axis and within the field of view of the image capture device. In some cases, the image capture device is focused on the sample flowstream by implementing a rotation of the flowcell, the rotation centered in the field of view of the image capture device. In some cases, the autofocusing of the image capture device includes determining an optimal focus position from among a plurality of focus positions.

In another aspect, embodiments of the present invention encompass methods for imaging particles in a blood fluid sample. Exemplary methods can include flowing a sheath fluid along a flowpath of a flowcell, and injecting the blood fluid sample into the flowing sheath fluid within the flowcell so that the blood fluid sample flows in a sample flowstream with a flowstream width greater than a flowstream thickness. The flowcell can have an associated temperature. Methods can also include focusing an image capture device, along an imaging axis, on the flowstream to a first focal state while the temperature associated with the flowcell is at a first temperature, and acquiring a first focused image of a first subset of the particles within the flowstream with the image capture device at the first focal state. Methods can further include determining that the temperature associated with the flowcell has undergone a change from the first temperature to a second temperature, and automatically adjusting focus of the image capture device from the first focal state to a second focal state in response to the change in temperature and a known relationship between flowcell temperature and desired focus. Further, methods can include acquiring a second focused image of a second subset of the particles within the flowstream with the image capture device at the second focal state. In some cases, adjusting focus of the image capture device involves adjusting a distance between the image capture device and the flowcell using the change in temperature and the known relationship between flowcell temperature and desired focus. In some cases, adjusting focus of the image capture device involves adjusting a focal distance of the image capture device using the change in temperature and the known relationship between flowcell temperature and desired focus. In some cases, adjusting focus of the image capture device involves implementing axial rotation of the image capture device about the imaging axis, axial rotation of the flowcell about an axis extending along the imaging axis and within the field of view of the imaging device, tip rotation of the image capture device about an axis extending along the flowpath, tip rotation of the flowcell about an axis extending along and within the flowpath, tilt rotation of the image capture device about an axis traversing the flowpath and the imaging axis, and/or tilt rotation of the flowcell about an axis traversing the flowpath and the imaging axis and within the field of view of the image capture device. In some cases, the image capture device is focused on the sample flowstream by implementing a rotation of the flowcell, the rotation centered in the field of view of the image capture device.

In another aspect, embodiments of the present invention encompass particle analysis systems that perform geometric hydrofocusing, or in some cases combined viscosity and geometric hydrofocusing, for imaging particles in a blood fluid sample. Exemplary systems can include a flowcell having a flowpath with an injection tube and an imaging window with an imaging axis therethrough. The flowpath of the flowcell can have a decrease in flowpath size. Systems can also include a sheath fluid input in fluid communication with the flowpath. Further, systems can include a blood fluid input in fluid communication with the infection tube. The blood fluid input can be configured for injecting the blood fluid sample into the flowing sheath fluid within the flowcell so that the blood fluid sample flows in a sample flowstream with a flowstream width greater than a flowstream thickness. In some cases, the sheath fluid can have a viscosity that is greater than a viscosity of the blood fluid sample. What is more, systems can include an image capture device, a focusing mechanism configured to set a focal state of the image capture device relative to the flowcell, and an imaging target having a position fixed relative to the flowcell. In some cases, the imaging target and sample flowstream can define a displacement distance along the imaging axis. Further, systems can include a processor, and a focusing module having a tangible medium embodying machine-readable code executed on the processor for operating the focusing mechanism to set the focal state of the image capture device, suitable for particle characterization and counting, using the displacement distance. In some cases, a viscosity difference between the sheath fluid and blood fluid sample, in combination with the decrease in flowpath size, is effective to hydrofocus the sample flowstream at the imaging axis while a viscosity agent in the sheath fluid retains viability of cells in the sample flowstream leaving structure and content of the cells intact when the cells extend from the sample flowstream into the flowing sheath fluid. In some cases, the focusing mechanism can include a drive motor configured to adjust a distance between the image capture device and the flowcell. In some cases, the imaging target is located on a viewport window disposed between the sample flowstream and the image capture device. In some cases, the imaging target is located on an illumination window, and the sample flowstream is disposed between the illumination window and the image capture device. In some cases, the system is configured to perform an acquiring step that includes focusing the image capture device on the sample flowstream by adjusting a focal distance of the image capture device based on the displacement distance. In some cases, the system is configured to perform an acquiring step for obtaining a focused image by adjusting a distance between the image capture device and the flowcell using the displacement distance. In some cases, the system is configured to adjust the distance between the image capture device and the flowcell by moving the flowcell. In some cases, the system is configured to perform an autofocusing step that includes injecting a test fluid sample into the sheath fluid to form a test sample flowstream within the flow cell, obtaining a first focused image of the imaging target using the image capture device, such that the focused imaging target and the image capture device define a first focal distance, obtaining a second focused image of the test sample flowstream using the image capture device, such that the focused test sample flow stream and the image capture device define a second focal distance, and obtaining the displacement distance by calculating a difference between the first focal distance and the second focal distance. In some cases, the system is configured to focus the image capture device on the sample flowstream using a temperature, such as a sample fluid temperature, a sheath fluid temperature, a flowcell temperature, or an image capture device temperature. In some cases, the system is configured to detect an autofocus re-initiation signal, and repeat autofocusing and image acquisition steps in response to the auto-focus re-initiation signal.

In another aspect, embodiments of the present invention encompass systems for imaging particles in a blood fluid sample. Exemplary systems can include a flowcell having a flowpath with an injection tube and an imaging window with an imaging axis therethrough, a sheath fluid input in fluid communication with the flowpath, and a blood fluid input in fluid communication with the injection tube. The blood fluid input can be configured for injecting the blood fluid sample into the flowing sheath fluid within the flowcell so that the blood fluid sample flows in a sample flowstream with a flowstream width greater than a flowstream thickness. Systems can also include an image capture device, a focusing mechanism configured to set a focal state of the image capture device relative to the flowcell, a temperature sensor thermally coupled to the flowcell, a processor, and a focusing module. The focusing module can include a tangible medium embodying machine-readable code executed on the processor for operating the focusing mechanism to set the focal state of the image capture device, suitable for particle characterization and counting, in response to a change in temperature sensed by the temperature sensor and a known relationship between temperature and desired focus. In some cases, the focusing mechanism includes a drive motor configured to adjust a distance between the image capture device and the flowcell.

In another aspect, embodiments of the present invention encompass methods for the analysis of cells in a blood fluid sample. Exemplary methods can include flowing a sheath fluid along a flowpath of a flowcell, and injecting the blood fluid sample into the flowing sheath fluid within the flowcell so that the blood fluid sample fluid flows in a sample flowstream with a flowstream width wider than a flowstream thickness. The sample flowstream can be offset, along an imaging axis, from an imaging window of the flowcell by a first distance. Methods can also include autofocusing an image capture device by imaging an imaging target affixed to the flowcell. The imaging target can be positioned at a second distance from the imaging window along the imaging axis. Further, methods can include acquiring focused images of the cells, suitable for cell characterization and counting, within the flowstream with the image capture device. In some cases, the image capture device can be focused on the sample flowstream using the autofocusing step and a known relationship between the first distance and the second distance.

In another aspect, embodiments of the present invention encompass systems for the analysis of cells in a blood fluid sample. Exemplary systems can include a flowcell having a flowpath with an injection tube and an imaging window with an imaging axis therethrough. Systems can also include a sheath fluid input in fluid communication with the flowpath, and a blood fluid input in fluid communication with the infection tube. The blood fluid input can be configured for injecting the blood fluid sample into the flowing sheath fluid within the flowcell so that the blood fluid sample flows in a sample flowstream with a flowstream width greater than a flowstream thickness. The sample flowstream can be offset, along the imaging axis, from the imaging window of the flowcell by a first distance. Systems can also include an image capture device orientable along the imaging axis. The image capture device can include a focusing mechanism. Further, systems can include an imaging target affixed to the flowcell. The imaging target can be at a second distance from the imaging window surface along the imaging axis. What is more, systems can include a processor coupled to the focusing mechanism. The processor can be configured to acquire focused images of the particles within the flowstream, sufficient for characterization and counting of the cells, by focusing the image capture device on the target, and by using a known relationship between the first distance and the second distance.

In yet another aspect, embodiments of the present invention encompass systems for the analysis of cells in a blood fluid sample. Exemplary systems can include a flowcell having a flowpath with an injection tube and an imaging window with an imaging axis therethrough. Further, systems can include a sheath fluid input in fluid communication with the flowpath, and a blood fluid sample input in fluid communication with the injection tube. The sample fluid input can be configured for injecting the blood fluid sample into the flowing sheath fluid within the flowcell so that the blood fluid sample flows in a sample flowstream with a flowstream width greater than a flowstream thickness. Further, systems can include an image capture device orientable along the imaging axis, and the image capture device can include a focusing mechanism. Systems can also include a temperature sensor thermally coupled to the flowcell, and a processor coupled to the temperature sensor and the focusing mechanism. In some cases, the processor is configured to adjust focus of the image capture device, sufficient for characterization and counting of the cells, in response to a change in temperature and a known relationship between temperature and desired focus.

According to some embodiments, a visual analyzer can include a flowcell coupled to a source of a sample and to a source of a sheath fluid. The flowcell can define an internal flowpath, and can be configured to direct a flow of the sample enveloped with the sheath fluid through a viewing zone in the flowcell. The analyzer can also include a high optical resolution imaging device with an objective on an optical axis that intersects the ribbon-shaped sample stream, and a relative distance between the objective and the flowcell can be variable by operation of a motor drive, for resolving and collecting a digitized image on a photosensor array. The analyzer can also include an autofocus pattern having a position fixed relative to the flowcell, the autofocus pattern being located at a displacement distance from the plane of the ribbon-shaped sample stream. The displacement distance can be predetermined. The analyzer can also include a light source configured to illuminate the ribbon-shaped sample stream and the autofocus pattern. Further, the analyzer can include at least one digital processor coupled to operate the motor drive and to analyze the digitized image. The processor can be configured to determine a focus position of the autofocus pattern and to relatively displace a high optical resolution imaging device and the flowcell over the displacement distance from the focused position, whereby the high optical resolution imaging device becomes focused on the ribbon-shaped sample stream. According to some embodiments, the autofocus pattern includes forms with limited size and the displacement distance is sufficient that the forms are substantially invisible in the digitized image when focused on the ribbon-shaped sample stream. In some cases, the optical axis is substantially perpendicular to the ribbon-shaped sample stream.

In another aspect, embodiments of the present invention encompass methods of focusing a visual analyzer for sample analysis. Exemplary methods can include focusing a high optical resolution imaging device on an autofocus pattern fixed relative to a flowcell, the autofocus pattern being located at a displacement distance from a ribbon-shaped sample stream that is predetermined, the high optical resolution imaging device with an objective on an optical axis that intersects the ribbon-shaped sample stream, a relative distance between the high optical resolution imaging device and the flowcell being variable by operation of a motor drive, the high optical resolution imaging device configured to resolve and collect a digitized image on a photosensor array. Further, methods can include operating the motor drive over the displacement distance to focus the high optical resolution imaging device on the ribbon-shaped sample stream.

In another aspect, embodiments of the present invention encompass methods of imaging particles in a sample. Exemplary methods can include providing a visual analyzer for a sample comprising particles suspended in a liquid, establishing a flow having laminar sections that are of higher and lower viscosity in the visual analyzer. The analyzer can include a flowcell coupled to a source of the sample and to a source of a PIOAL having a higher viscosity than the viscosity of the sample. The flowcell can define an internal flowpath, and can direct a flow of the sample enveloped with the PIOAL through a viewing zone in the flowcell. The analyzer can also include a high optical resolution imaging device with an objective on an optical axis that intersects the ribbon-shaped sample stream, a relative distance between the high optical resolution imaging device and the flowcell being variable by operation of a motor drive, for resolving and collecting a digitized image on a photosensor array. The analyzer can also include an autofocus pattern having a position fixed relative to the flowcell, the autofocus pattern being located at a displacement distance from the plane of the ribbon-shaped sample stream that has been predetermined, a light source configured to illuminate the ribbon-shaped sample stream and the autofocus pattern, at least one digital processor coupled to operate the motor drive and to analyze the digitized image, where the processor is configured to determine a focus position of the autofocus pattern and to relatively displace the high optical resolution imaging device and the flowcell over the displacement distance from the focused position, whereby the high optical resolution imaging device becomes focused on the ribbon-shaped sample stream. In some cases, an analyzer can include a flowcell coupled to a source of the sample and to a source of a PIOAL where the flowcell defines an internal flowpath and is configured to direct a flow of the sample enveloped with the PIOAL through a viewing zone in the flowcell, a high optical resolution image device with an objective on an optical axis that intersects the ribbon-shaped sample stream, a relative distance between the objective and the flowcell being variable by operation of a motor drive, for resolving and collecting a digitized image on a photosensor array, an autofocus pattern having a position fixed relative to the flowcell, the autofocus pattern being located at a displacement distance from the plane of the ribbon-shaped sample stream that has been predetermined, a light source configured to illuminate the ribbon-shaped sample stream and the autofocus pattern, and at least one digital processor coupled to operate the motor drive and to analyze the digitized image, where the processor is configured to determine a focus position of the autofocus pattern and to relatively displace the high optical resolution imaging device and the flowcell over the displacement distance from the focused position, whereby the high optical resolution imaging device becomes focused on the ribbon-shaped sample stream.

In some cases, the images obtained by the systems and methods described herein can be digitized images. In some cases, the images can be microscopy images. In some cases, the images can be observed manually or by automation.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 4A-1 and 4A-2 depict cross-section views of sheath fluid (e.g. PIOAL) envelope and sample fluidstream dimensions within a flowcell at a cannula exit port and an image capture site, respectively, according to embodiments of the present invention.

FIGS. 4K-1, and 4K-2 show a target imaging site according to embodiments of the present invention.

FIG. 4K-3 depicts aspect of particle alignment in a sample flowstream, according to embodiments of the present invention.

DETAILED DESCRIPTION OF THE INVENTION

Figure 1:
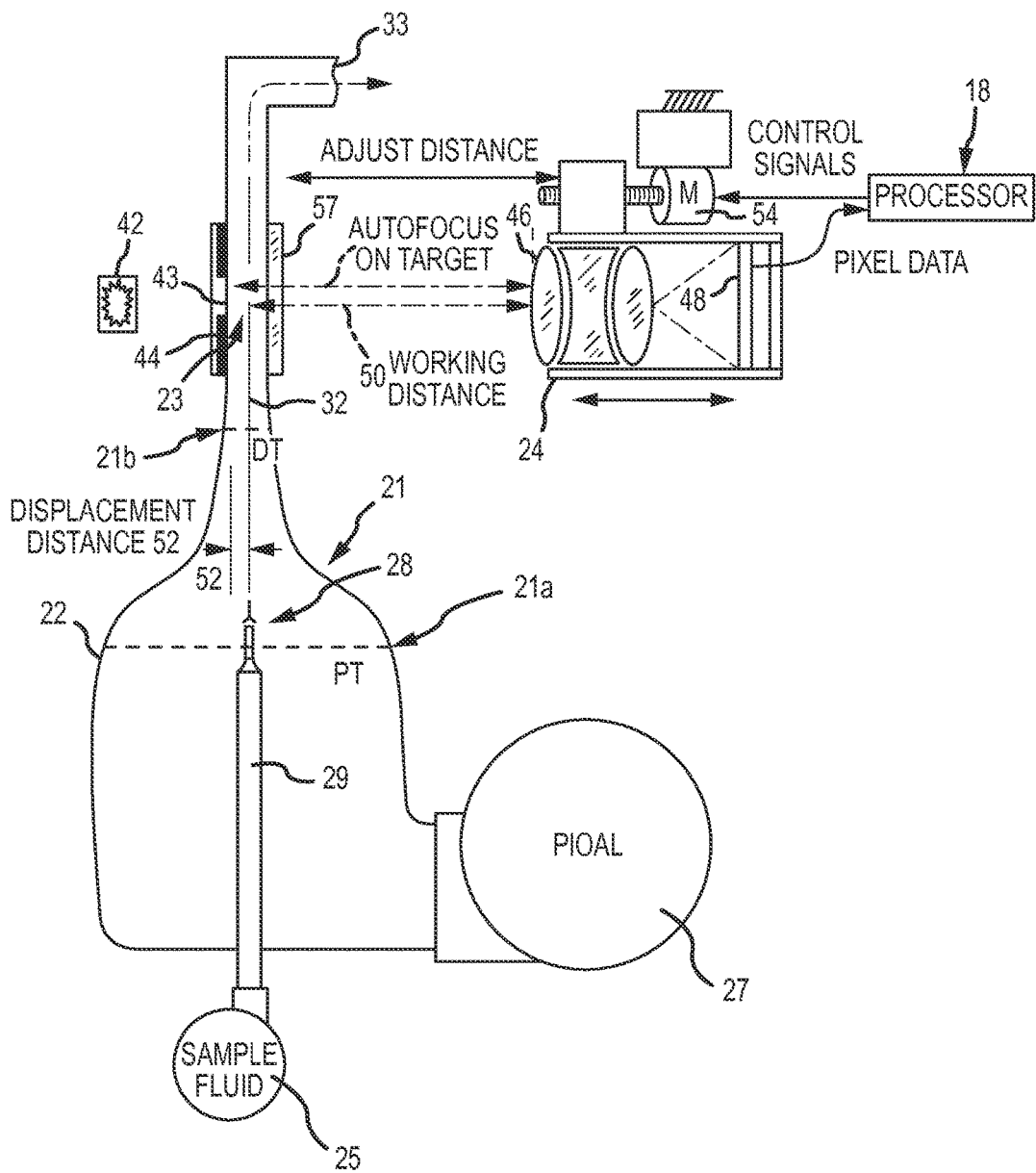
FIG. 1 is a schematic illustration, partly in section and not to scale, showing operational aspects of an exemplary flowcell, autofocus system and high optical resolution imaging device for sample image analysis using digital image processing.

The present disclosure relates to apparatus, systems, compositions, and methods for analyzing a sample containing particles. In one embodiment, the invention relates to an automated particle imaging system which comprises an analyzer which may be, for example, a visual analyzer. In some embodiments, the visual analyzer may further comprise a processor to facilitate automated analysis of the images.

Exemplary particles can include any of the formed elements in biological fluid samples as disclosed herein, including, for example, spherical and non-spherical particles. The PIOAL aligns non-spherical particles in a plane substantially parallel to the flow direction, which results in image optimization. The PIOAL also assists spherical cells in positioning, repositioning and/or better-positioning of intracellular structures, organelles or lobes substantially parallel to the direction of flow. In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

The PIOAL can be introduced into a flowcell and carries the sample through the imaging area, then along toward the discharge. The stream of sample fluid can be injected through a cannula with a flattened opening to establish a flowpath with a considerable width. For example, the PIOAL can have a relatively higher viscosity than the sample fluid, suitable density, and flow rates at the point of injection of the sample are such that the sample fluid flattens into a thin ribbon shape. The ribbon of sample fluid is carried along with the PIOAL, to pass in front of a viewing port where a high optical resolution imaging device and a light source are arranged to view the ribbon-shaped sample stream.

The ribbon-shaped sample stream is carried along with the PIOAL, to pass in front of a viewing port where a high optical resolution imaging device and a light source (e.g., UV, visible, or IR) are arranged to view the ribbon-shaped sample stream. The high optical resolution imaging device and light source can be placed on opposite sides of the flowcell, for obtaining backlit images of the particles such as blood cells. The high optical resolution imaging device captures pixel data images of the sample through a viewing port in the flowcell. For example, the high optical resolution imaging device captures images at a repetition rate consistent with the sample flow velocity such that sections of the ribbon-shaped sample stream are imaged without substantial gaps or overlap.

Embodiments of the present invention provide a number of unique structural and functional features implemented in the design and operation of a system for collecting images of a ribbon-shaped sample stream flowing through a flowcell. Exemplary embodiments are configured to obtain sufficiently focused images of the particles, with sufficient clarity and resolution to reveal the different features of the various particles such as blood cells, that allow the particle and/or cell types to be distinguished from one another.

In order to bring the ribbon-shaped sample stream into focus, the distance between the high optical resolution imaging device and the ribbon-shaped sample stream can be set such that the ribbon-shaped sample stream is at a desired distance (e.g., the focusing distance) from the high optical resolution imaging device along the optical axis.

A focusing distance is a characteristic of the lenses of the high optical resolution imaging device used to resolve the image on a photosensor array, namely defined by the material, shape and dimensions of the lens elements and their configuration and placement along the optical axis. The dimensions of the area of the sample that is imaged, and the depth of field that is in focus in the sample, are determined by the lens configuration.

Aperture adjustments and zoom adjustments are possible, but for purposes of simplicity, certain examples in this disclosure are such that focusing the high optical resolution imaging device on the particles in the ribbon-shaped sample stream simply requires relatively positioning the high optical resolution imaging device and the ribbon-shaped sample stream in the flowcell at a correct distance, namely the distance that resolves a focused image on the photosensor array (e.g., a charge-coupled device array) of particles in the ribbon-shaped sample stream. The high optical resolution imaging device may include a camera that records or transmits still images or video images for display and/or processing and/or transmission.

In one aspect, the symmetrical nature of the flowcell and the manner of injection of the sample fluid and PIOAL provide a repeatable position within the flowcell for the ribbon-shaped sample stream in the PIOAL. However, the relative positions of the flowcell and the high optical resolution imaging device are subject to change and require occasional position adjustments to maintain the optimal distance between the high optical resolution imaging device and the ribbon-shaped sample stream, thus providing a quality focus image.

Embodiments of the present invention encompass automated visual analyzer systems and methods for blood and/or other biological fluids that incorporate an autofocus device/apparatus to provide reliably focused images of the sample by very accurately setting the distance between the ribbon-shaped sample stream and the high optical resolution imaging device. In one aspect, autofocus system embodiments disclosed herein can very accurately set the distance between the ribbon-shaped sample stream and the high optical resolution imaging device and capture reliably focused images of the sample. In some embodiments, algorithms are used to establish the distance that achieves good focus results.

It is an object to employ a flowcell, that provides a stable and highly repeatable position for a ribbon-shaped sample stream enveloped in a flow of PIOAL, in combination with a high optical resolution imaging device and autofocus device/apparatus that maintains the optimal distance between the high optical resolution imaging device and the ribbon-shaped sample stream, thus providing a quality focused image.

Such apparatus and methods are disclosed and claimed herein. A symmetrical flowcell is provided, which has been found to produce a repeatable ribbon-shaped sample stream position within the flowcell. Focusing involves setting a precisely correct relative position of the high optical resolution image device relative to the ribbon-shaped sample stream, so as to maintain focus on the ribbon-shaped sample stream.

Advantageously, the flowcell and/or the high optical resolution image device can be moved relative to one another in an autofocusing process using an autofocus pattern such as a high contrast pattern or similar focusing target, preferably a planar target with sharply contrasting features such as edges, the autofocus pattern being fixed in position relative to the flowcell and used as a focusing subject in lieu of the sample itself. The ribbon-shaped sample stream is a thin ribbon at a fixed distance from the autofocus pattern along the line parallel to the optical axis of the high optical resolution imaging device. The displacement distance between the autofocus pattern and the ribbon-shaped sample stream position is a constant distance, which is determined initially and programmed into the autofocus procedure. The exemplary technique thereafter is to autofocus on the autofocus pattern, then to displace the high optical resolution image device and/or flowcell relative to one another by the known and constant predetermined distance, whereupon the distance between the high optical resolution image device and the location of the ribbon-shaped sample stream is the optimal distance to provide a quality focused image of the ribbon-shaped sample stream. For example, at first, an autofocus algorithm focuses the position of the high optical resolution imaging device on the autofocus pattern located at a fixed distance from the ribbon-shaped sample stream. Having focused on the autofocus pattern, the processor operates the motor drive over the fixed distance, thereby bringing the ribbon-shaped sample stream into focus of the high optical resolution imaging device.

An exemplary high optical resolution image device comprises an objective lens and associated pixel image sensor, capable of capturing an image that reveals the particles at sufficient magnification and resolution to provide sufficient detail to resolve visual features of the particles. In certain embodiments, the magnification is higher by a factor of at least 2× (thus providing a 2× image area per each image taken), thereby generating more detailed information for each particle as compared to traditional urine analyzers.

The PIOAL flowpath can be arranged symmetrically such that equal amounts of PIOAL flow above and below the ribbon-shaped sample stream which stretches and locates the ribbon-shaped sample stream as a thin ribbon at a fixed distance from the autofocus pattern along the line parallel to the optical axis of the high optical resolution imaging device. In one embodiment the autofocus pattern comprises an opaque border around an opening admitting light from a source of rear illumination and the distance of the autofocus pattern is readily and unambiguously homed in upon by the autofocus controls. Then, the ribbon-shaped sample stream is brought into focus by displacing the high optical resolution imaging device relatively to the flow cell over the predetermined and constant displacement distance. There is no need for autofocusing directly on the image content of the sample, although further autofocusing is conceivable.

An automated focusing configuration includes a motor drive that adjusts the relative position of the flowcell and a high optical resolution imaging device along the optical axis, responsive to control signals from a processor that assesses one or more measures of focus quality over a range of distances and seeks an optimal distance. For example, the processor may assess a measure of contrast and operate the motor drive for autofocusing. In normal operation the processor operates the motor drive to autofocus on the target and then adjusts the distance between the high optical resolution imaging device and the flowcell by the recorded displacement from the target to bring the ribbon-shaped sample stream into focus. So long as the device continues to move the ribbon-shaped sample stream in the same way, and thermal expansion or similar confounding factors do not arise, the image of the ribbon-shaped sample stream will remain in focus.

A preliminary set-up or calibration process can be used to determine and record the displacement distance between the target and the ribbon-shaped sample stream position in the flowcell. The exact displacement distance, which may differ slightly for different flowcells, is established by preliminary testing, such as by autofocusing alternatively on the target and on a test ribbon-shaped sample stream several times, and recording the mean result as a constant associated with the flowcell.

Accordingly, a sample to be imaged, such as a prepared blood sample or another type of sample, is directed along a defined flowpath through a viewing zone in a flowcell. The PIOAL flowpath preferably is symmetrical and the sample is injected in the center of the PIOAL flow, with which the sample is enveloped. The flow rates and viscosity and density characteristics of the sample and the sheath material such as a PIOAL, together with the contour of the flowcell, cooperate so as to form the ribbon-shaped sample stream into a flat ribbon flowing consistently through the viewing zone at a repeatable position.

The sample may be imaged by a camera component of the high optical resolution imaging device and digital images collected to be analyzed by at least partly automated image analysis processes, including an autofocus process as described herein.

One object is to distinguish, categorize, subcategorize and/or count particles such as blood cells in blood samples as well as other biological samples described herein, which may be associated with particular conditions. In one aspect, the particle contrast agent compositions of this disclosure can be combined with a visual analyzer such as the analyzer described herein in a method to provide surprisingly high quality focused images of cells in flow. The cells may be automatically captured and processed.

The images allow for automated image based WBC differential counting, as well as automated identification of morphological abnormalities useful in determining, diagnosing, prognosing, predicting, and/or supporting a diagnosis of whether a subject is healthy or has a disease, condition, abnormality and/or infection and/or for determining or monitoring whether the subject is responsive or non-responsive to treatment. Cell category and/or subcategory counts in blood samples are used in this disclosure as nonlimiting examples of the sort of fluids that may be analyzed.

In one aspect, the image analyzers for use with the compositions of this invention can capture reliably focused images of the sample by very accurately setting the distance between the ribbon-shaped sample stream and the high optical resolution imaging device of the optical system. In some embodiments, the visual analyzers can be used in combination with the compositions of this invention and algorithms to establish said distance that can achieve good focus results. The sample is arranged in the flowcell and illuminated to enable viewing through a viewing port. The individual cells or particles appear clearly in the captured pixel data image, with sufficient feature detail to reveal attributes that are then compared and contrasted with parameters known to distinguish categories and subcategories of cells from one another.

It is an object to employ a flowcell in combination with the exemplary particle contrast agent compositions described herein, and an exemplary PIOAL, that provides images of optimal quality and detail for particle recognition. In addition, the PIOAL and apparatus provides a stable and highly repeatable position for a ribbon-shaped sample stream enveloped in a flow of PIOAL. This, in combination with a high optical resolution imaging device and the autofocus device/apparatus that maintains the optimal distance of the high optical resolution imaging device to the ribbon-shaped sample stream, provides a quality focused image.

In certain aspects, the analyzer and the processor can be configured to provide additional information to correct categorizing errors associated with the particle counter, and further determine accurate particle count or concentration of different categories and/or subcategories of particles and the members in each category, or in each subcategory of particles in the sample.

According to this disclosure, a system comprising a visual analyzer is provided for obtaining images of a sample comprising particles suspended in a liquid. The system may be useful, for example, in characterizing particles in biological fluids, such as detecting and quantifying erythrocytes, reticulocytes, nucleated red blood cells, platelets, and white blood cells, including white blood cell differential counting, categorization and subcategorization and analysis. Other similar uses such as characterizing blood cells from other fluids are also contemplated.

The discrimination of blood cells in a blood sample is an exemplary application for which the subject matter is particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a blood sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. The flowcell is coupled to a source of sample fluid, such as a diluted and/or treated blood sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

The instant disclosure provides methods and compositions useful for particle and/or intracellular organelle alignment in conducting image-based sample analysis. In some embodiments, this disclosure relates to methods and compositions for combined counting and imaging system with the ability to perform a complete blood count (CBC) and an image based expanded white blood cell (WBC) differential able to identify and count cell types, such as WBCs, RBCs, and/or platelets, including, for example, neutrophils, lymphocytes, monocytes, eosinophils, basophils, reticulocytes, nucleated RBCs, blasts, promyelocytes, myelocytes, or metamyelocytes, and to provide image based information for WBC counts and morphologies, red blood cell (RBC) counts and morphologies and platelet (PLT) counts and morphologies.

In other embodiments, this disclosure relates to a PIOAL that can be used in image based analysis of particles as described herein. Cell category and/or subcategory count in blood samples is used in this disclosure as nonlimiting examples of the sort of samples that may be analyzed. In some embodiments, cells present in samples may also include bacterial or fungal cells as well as white blood cells, red blood cells and/or platelets. In some embodiments, particle suspensions obtained from tissues or aspirates may be analyzed.

The discrimination of blood cells in a blood sample is an exemplary application for which the subject matter is particularly well suited. The sample is prepared by automated techniques and presented to a high optical resolution imaging device as a ribbon-shaped sample stream to be imaged periodically while the sample flows across a field of view. The images of the particles (such as blood cells) can be distinguished from one another, categorized, subcategorized, and/or counted, using pixel image data programmed processing techniques, either exclusively automatically or with limited human assistance, to identify and count cells or particles. In addition to the cell images, which can be stored and made available in the case of unusual or critical features, the output data includes a count of the occurrences of each particular category and/or subcategory of cell or particle distinguished in the recorded sample images. The counts of the different particles found in each image can be processed further, for example used to accumulate accurate and statistically significant proportionate ratios, or functions thereof of cells of each distinguished category and/or subcategory in the sample as a whole. The sample used for visual discrimination can also be highly diluted, but the proportions of cells in each category and/or subcategory are represented in the distribution for the diluted sample, particularly after a number of images have been processed.

In some aspects, samples are presented, imaged and analyzed in an automated manner. In the case of blood samples, the sample may be substantially diluted with water or saline solution, which reduces the extent to which the view of some cells might be hidden by other cells in an undiluted or less-diluted sample. The cells can be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flowcell and imaging.

The particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference.

To facilitate the capacity, speed and effectiveness by which particles such as cells are categorized and/or subcategorized, it is advantageous to provide clear high quality images of the blood cells for automated analysis by the data processing system. According to the present disclosure, a prepared sample stream is arranged in a thin ribbon having a stable position between opposite walls of a flowcell. The positioning of the sample stream and its flattening into a thin ribbon shape may be achieved by flow between layers of a PIOAL introduced into the flowcell that differs in viscosity from the sample fluid and is flowed through a symmetrical flow channel.

The PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location. The sample fluid stream may be compressed to approximately 2 to 3 µm in fluid flow thickness. Several blood cell types have diameters larger than the stream thickness. Sheer forces in the direction parallel to the direction of the flow cause an increase of an image projection of the particles under imaging conditions in the focal plane of the high optical resolution imaging device and/or causing the intraparticle structures, for example, intracellular structures, organelles or lobes, to be positioned, repositioned, and/or better-positioned to be substantially parallel to the direction of flow. The high optical resolution imaging device depth of field is up to 7 µm, for example, 1-4 µm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure is based on the surprising and unexpected discovery that the addition of a suitable amount of a viscosity agent in the PIOAL significantly improves particle/cell alignment in a flowcell, leading to a higher percentage of in-focus cells, or cellular components, and higher quality images of cells and/or particles in flow. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow. In some embodiments, a reduction in RBC misalignment and/or increase in RBC alignment is achieved by increasing the viscosity of the PIOAL.

The ribbon-shaped sample stream thickness can be affected by the relative viscosities and flow rates of the sample fluid and the PIOAL. The source of the sample and/or the source of the PIOAL, for example comprising precision displacement pumps, can be configured to provide the sample and/or the PIOAL at controllable flow rates for optimizing the dimensions of the ribbon-shaped sample stream, namely as a thin ribbon at least as wide as the field of view of the high optical resolution imaging device or the digital image capture device.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

In one aspect of the methods of this invention, the cells contacted with particle contrast agent composition and/or imaged are nucleated red blood cells. In yet another aspect, the methods of this invention relate to a method for performing image-based red blood cell categorization and subcategorization comprising: a) imaging a portion of the red blood cells; and b) determining the morphology of the imaged red blood cells. As used herein, red blood cells (RBC) can include, for example, normal or abnormal red blood cells, reticulocytes, nucleated red blood cells, and/or malaria-infected cells. In some embodiments, the imaging is performed using the apparatus of this disclosure such as an apparatus comprising a particle counter, a visual analyzer and a processor.

As used herein, an exemplary complete blood count (CBC) can include a test panel typically requested by a doctor or other medical professional that provides information about the particles and/or cells in a patient's blood sample. Exemplary cells that circulate in the bloodstream can be generally divided into three types: including but not limited to, for example, white blood cells (e.g., leukocytes), red blood cells (e.g., erythrocytes), and platelets (e.g., thrombocytes).

As used herein, abnormally high or low counts may indicate the presence of disease, disorder, and/or condition. Thus, a CBC is one of the commonly performed blood tests in medicine, as it can provide an overview of a patient's general health status. Accordingly, a CBC is routinely performed during annual physical examinations.

As used herein, typically a phlebotomist collects the blood sample from the subject, the blood is generally drawn into a test tube typically containing an anticoagulant (e.g., EDTA, sometimes citrate) to stop it from clotting. The sample is then transported to a laboratory. Sometimes the sample is drawn off a finger prick using a Pasteur pipette for immediate processing by an automated counter. In one embodiment, the particle image is acquired while the particle is enveloped in a sheath fluid or PIOAL. In certain embodiments, the blood sample may be viewed on a slide prepared with a sample of the patient's blood under a microscope (a blood film, or peripheral smear). In certain embodiments, the complete blood count is performed by an automated analyzer.

As used herein, in general, blood analyzers can aspirate a very small amount of the specimen through narrow tubing. Sensors can detect the count and/or the number of cells passing through the tubing, and can identify the type of cell. Exemplary sensors may include detectors of light (e.g., visible, UV or IR) and/or electrical impedance. Exemplary detection parameters may include size, volume, and/or cellular features. In certain embodiments, the sensors can detect visible and non-visible light in a wavelength spectrum ranging from about 200 nm to about 10000 nm. In certain embodiments, the sensors can detect a wavelength of between about between 380 nm and about 760 nm.

As used herein, data/parameters of a blood count can include, for example, total red blood cells; hemoglobin—the amount of hemoglobin in the blood; hematocrit or packed cell volume (PCV); mean corpuscular volume (MCV)—the average volume of the red cells (anemia is classified as microcytic or macrocytic based on whether this value is above or below the expected normal range. Other conditions that can affect MCV include thalassemia, reticulocytosis and alcoholism); mean corpuscular hemoglobin (MCH)—the average amount of hemoglobin per red blood cell, in picograms; mean corpuscular hemoglobin concentration (MCHC)—the average concentration of hemoglobin in the cells; red blood cell distribution width (RDW)—the variation in cellular volume of the RBC population; total white blood cells; neutrophil granulocytes (may indicate bacterial infection, typically increased in acute viral infections). Due to the segmented appearance of the nucleus, neutrophils are sometimes referred to as "segs" The nucleus of less mature neutrophils is not segmented, but has a band or elongated shape. Less mature neutrophils—those that have recently been released from the bone marrow into the bloodstream—are known as "bands". Other data/parameters for a blood count can also include, for example, lymphocytes (e.g., increased with some viral infections such as glandular fever, and in chronic lymphocytic leukemia (CLL), or decreased by HIV infection); monocytes (may be increased in bacterial infection, tuberculosis, malaria, Rocky Mountain spotted fever, monocytic leukemia, chronic ulcerative colitis and regional enteritis; eosinophil granulocytes (e.g., increased in parasitic infections, asthma, or allergic reaction); basophil granulocytes (e.g., increased in bone marrow related conditions such as leukemia or lymphoma.

As used herein, data/parameters of a blood count can also include, for example, data associated with platelets, including platelet numbers, information about their size and the range of sizes in the blood; mean platelet volume (MPV)—a measurement of the average size of platelets.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

In another aspect of the methods of this invention, the cells are platelets.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

As used herein, detectable and measurable particle parameters can include, for example, visual and/or non-image based indices of size, shape, symmetry, contour and/or other characteristics.

The sample can be an isolated and/or prepared biological sample, including for example, a body fluid sample, a blood, serum, cerebrospinal fluid, pleural fluid, peritoneal fluid, saliva, seminal fluid, tears, sweat, milk, amniotic fluid, lavage fluid, bone marrow asirate, effusions, exudates, or other sample obtained from a subject (e.g., biopsy sample that has been treated to produce a cell suspension, or a laboratory or production line sample comprising particles). In some embodiments, the sample can be a solid tissue sample, e.g., a biopsy sample that has been treated to produce a cell suspension. The sample may also be a suspension obtained from treating a fecal sample. A sample may also be a laboratory, chemical, industrial or production line sample comprising particles, such as a cell culture sample. The term sample may be used to refer to a sample obtained from a patient or laboratory or any fraction, portion or aliquot thereof. The sample can be diluted, divided into portions, or treated with a contrast agent in some processes.

The methods disclosed herein are applicable to samples from a wide range of organisms, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

The samples can be obtained by any conventional method, e.g., excretion, draw, harvesting, aspirate, or a biopsy. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment and/or therapy, a clinician can choose an alternative or adjunctive agent. Depending upon the condition of the subject and the particular disorder, if any, samples can be collected once (or twice, three times, etc.) daily, weekly, monthly, or yearly.

The particles can vary depending upon the sample. The particles can be biological cells, for example, blood cells, fetal cells, stem cells, tumor cells or fragments thereof. In some embodiments the particles can be an infectious agent, for example, a virus or bacterium.

Reference to "blood cells" made in this disclosure will be understood to encompass any normal or abnormal, mature or immature cells which potentially exist in a biological fluid, for example, red blood cells (RBCs), white blood cells (WBCs), platelets (PLTs) and other cells. In general, normal RBCs, PLTs, and WBCs have a particle diameter in the range of 6-8 µm, 2-3 µm, and 8-15 µm, respectively. Normal RBCs, PLTs and WBCs are present in whole blood samples from normal patients in an approximate concentration range of $3.9-5.7 \times 10^{12}$ cells/L, $1.4-4.5 \times 10^{11}$ cells/L, $3.5-11 \times 10^{9}$ cells/L, respectively. See, Barbara J. Bain, Blood Cells, A Practical Guide, 4th ed., Blackwell Publishing, 2007, 34-36.

Reference to a "formed element" will be understood to encompass non-fluid elements present in biological fluid samples. Formed elements include, for example, classes of blood cells based on scientific classification or physiological function including erythrocytes (RBCs), leukocytes (WBCs) and platelets (PLTs), WBC clumps, subclasses of leukocytes, which include mature lymphocytes, and immature leukocytes such as monocytes, neutrophils, eosinophils, basophils. "Formed elements" for use herein will also include particles such as microorganisms, bacteria, fungi, parasites, or fragments thereof or other cell fragments. Major members of WBCs include but are not limited to neutrophils, lymphocytes, monocytes, eosinophils, and basophils. The members also include immature or abnormal cells. For example, immature WBCs may include metamyelocytes, myelocytes, pro-myelocytes. In addition to mature RBCs, members of RBCs may include nucleated RBCs (NRBCs) and reticulocytes. PLTs may include regular PLTs, and "giant" PLTs whose size is close to that of regular WBCs. Reference to a "member" or "members" of a category and/or subcategory of particles made in this disclosure will be understood to encompass individual particles within a category or sub-category of particles.

Unless expressly indicated otherwise, reference to a "category" of particles made in this disclosure will be understood to encompass a group of particles detected using at least one detection criterion measured, detected or derived such as size, shape, texture, or color. In some embodiments the members of at least one category and/or subcategory of particles counted by the apparatus of this disclosure will be the same type of formed element.

Such particles may be detected in a "channel." Reference to "channel" made in this disclosure will be understood to encompass a portion of the particle counter comprising a detector coupled to a signal source, providing an output that varies with greater or lesser detection of particles that meet at least one channel detection criterion. For example, a channel detection criterion can be based on size or volume of the particles. In some embodiments, the number of channels in a particle counter is one. In some other embodiments, the number of the channels in a particle counter is two or more.

One category and/or subcategory of particles detected in one channel of particle counter may comprise different classes and subclasses of particles, and grouped members of particles in two or more subclasses. Reference to a "category" of particles made in this disclosure will be understood to encompass a grouping of particles corresponding to criteria measured, detected or derived such as size, shape, texture, or color. In some embodiments the members of at least one category and/or subcategory of particles counted by the apparatus of this disclosure will be the same type of formed element.

As used herein, the term high optical resolution imaging device can include devices that are capable of obtaining particles images with sufficient visual distinctions to differentiate morphological features and/or changes. Exemplary high optical resolution imaging devices can include devices with an optical resolution of 1 µm or lower, including for example, 0.4 to 0.5 um, such as for example, 0.46 µm.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

As used herein, "alignment" can be characterized in part by the alignment of spherical and/or non-spherical particles. For example, particles such as non-spherical particles may be aligned in a plane substantially parallel to the direction of the flow. In certain embodiments, alignment of the non-spherical particles is characterized by the orientation of the particles increase an image projection of the non-spherical particles under imaging conditions in the focal plane of the high optical resolution imaging device. Particles such as spherical particles may have an increase in the amount of the in focus intraparticle contents of the particles and cells which is effective to generate visual distinctions for particle categorization and subcategorization. The intraparticle structures of particles such as spherical particles may be positioned, repositioned and/or better-positioned to be substantially parallel to the direction of flow. For example, intracellular structures, organelles or lobes may also be positioned, repositioned, and/or better-positioned to be substantially parallel to the direction of flow.

Reference to a "class" of particles made in this disclosure will be understood to encompass a group of particles based on scientific classification. For example, three major classes of blood cells exist in a whole blood sample, including RBCs, WBCs and PLTs.

Reference to a "member" or "members" of particles made in this disclosure will be understood to encompass particles in one category or subcategory of particles. For example, each category of blood cells can be further divided into subcategories or members. Major members of WBCs include but are not limited to neutrophils, lymphocytes, monocytes, eosinophils, and basophils. The members also include immature or abnormal cells. For example, immature WBCs may include metamyelocytes, myelocytes, and promyelocytes. In addition to mature RBCs, members of RBCs may include nucleated RBCs (NRBCs) and reticulocytes. PLTs may include regular PLTs, and "giant" PLTs whose size is close to that of regular WBCs.

Reference to "immature cells" will be understood to encompass cells in a certain developmental stage, for example, inside the bone marrow or shortly after release from bone marrow but before full development into a mature cell.

Reference to "abnormal cells" will be understood to encompass cells with irregular morphological characteristics or cells associated with a certain disease or condition, or irregularities associated which may in some instances be associated with certain diseases or conditions. Examples of certain disease include but are not limited to erythrocytosis, polycythemia, anemia, erythroblastopenia, leukocytosis, leukopenia, lymphocytosis, lymphocytopenia, granulocytosis, granulocytopenia or agranulocytosis, neutrophilia, neutropenia, eosinophilia, eosinopenia, basophilia, basopenia, thrombocytosis, thrombocytopenia, and pancytopenia. A class of cells may increase or decrease in the bloodstream. In some conditions, abnormal cells much larger than regular white cells exist at a small concentration in a blood sample. Variations in size, shape, color, and/or intracellular structures may be associated with certain diseases or conditions.

Reference to "count" of particles or "particle count" made in this disclosure will be understood to encompass the numbers of particles obtained from one channel of a particle counter. Reference to "concentration" of a class or a member of particles made in this disclosure will be understood to mean the numbers of the particles per unit volume (e.g., per liter) or per sample of a known volume. For example, a particle counter may provide counts or concentrations or other count based function for categories of particles, while a visual analyzer may provide counts, concentrations, ratios or other concentration based parameters for each category or subcategory of particles.

Reference to "ratio" made in this disclosure will be understood to encompass any quantitative and/or proportionate ratio of two categories/subcategories, classes or members of particles. Examples of such a ratio include but are not limited to a ratio by concentration, weight, and/or by numbers of particles. Typically the ratio concerns the numerical fraction of the count of one category, class or member over the count of another such category, class or member. In some embodiments, determinations using weighted counts or weighted and/or proportionate ratios may also be made.

Hematology—Particle Analysis System

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAL to a discharge 33.

As shown here, the narrowing zone 21 can have a proximal flowpath portion 21*a* having a proximal thickness PT and a distal flowpath portion 21*b* having a distal thickness DT, such that distal thickness DT is less than proximal thickness PT. The sample fluid can therefore be injected through the distal end 28 of sample tube 29 at a location that is distal to the proximal portion 21*a* and proximal to the distal portion 21*b*. Hence, the sample fluid can enter the PIOAL envelope as the PIOAL stream is compressed by the zone 21. wherein the sample fluid injection tube has a distal exit port through which sample fluid is injected into flowing sheath fluid, the distal exit port bounded by the decrease in flowpath size of the flowcell.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

The present disclosure provides a technique for automatically achieving a correct working position of the high optical resolution imaging device 24 for focusing on the ribbon-shaped sample stream 32. The flowcell structure 22 can be configured such that the ribbon-shaped sample stream 32 has a fixed and dependable location within the flowcell defining the flow path of sample fluid, in a thin ribbon between layers of PIOAL, passing through a viewing zone 23 in the flowcell 22. In certain flowcell embodiments, the cross section of the flowpath for the PIOAL narrows symmetrically at the point at which the sample is inserted through a flattened orifice such as a tube 29 with a rectangular lumen at the orifice, or cannula. The narrowing flowpath (for example geometrically narrowing in cross sectional area by a ratio of 20:1, or by a ratio between 20:1 to 70:1) along with a differential viscosity between the PIOAL and sample fluids, and optionally, a difference in linear speed of the PIOAL compared to the flow of the sample, cooperate to compress the sample cross section by a ratio of about 20:1 to 70:1. In some embodiments the cross section thickness ratio may be 40:1.

In one aspect, the symmetrical nature of the flowcell 22 and the manner of injection of the sample fluid and PIOAL provide a repeatable position within the flowcell 22 for the ribbon-shaped sample stream 32 between the two layers of the PIOAL. As a result, process variations such as the specific linear velocities of the sample and the PIOAL; do not tend to displace the ribbon-shaped sample stream from its location in the flow. Relative to the structure of the flowcell 22, the ribbon-shaped sample stream 32 location is stable and repeatable.

However, the relative positions of the flowcell 22 and the high optical resolution imaging device 24 of the optical system may be subject to change and may benefit from occasional position adjustments to maintain an optimal or desired distance between the high optical resolution imaging device 24 and the ribbon-shaped sample stream 32, thus providing a quality focus image of the enveloped particles in the ribbon-shaped sample stream 32. According to some embodiments, there can be an optimal or desired distance between the high optical resolution imaging device 24 and the ribbon-shaped sample stream 32 for obtaining focused images of the enveloped particles. The optics can first be positioned accurately relative to the flowcell 22 by autofocus or other techniques to locate the high optical resolution imaging device 24 at the optimal or desired distance from an autofocus target 44 with a fixed position relative to the flowcell 22. The displacement distance between the autofocus target 44 and the ribbon-shaped sample stream 32 is known precisely, for example as a result of initial calibration steps. After autofocusing on the autofocus target 44, the flowcell 22 and/or high optical resolution imaging device 24 is then displaced over the known displacement distance between the autofocus target 44 and the ribbon-shaped sample stream 32. As a result, the objective lens of the high optical resolution imaging device 44 is focused precisely on the ribbon-shaped sample stream 32 containing the enveloped particles.

Exemplary embodiments of the present invention involve autofocusing on the focus or imaging target 44, which is a high contrast figure defining a known location along the optical axis of the high optical resolution imaging device or the digital image capture device 24. The target 44 can have a known displacement distance relative to the location of the ribbon-shaped sample stream 32. A contrast measurement algorithm can be employed specifically on the target features. In one example, the position of the high optical resolution imaging device 24 can be varied along a line parallel to the optical axis of the high optical resolution imaging device or the digital image capture device, to find the depth or distance at which one or more maximum differential amplitudes are found among the pixel luminance values occurring along a line of pixels in the image that is known to cross over an edge of the contrast figure. In some cases, the autofocus pattern has no variation along the line parallel to the optical axis, which is also the line along which a motorized control operates to adjust the position of the high optical resolution imaging device 24 to provide the recorded displacement distance.

In this way, it may not be necessary to autofocus or rely upon an image content aspect that is variable between different images, that is less highly defined as to contrast, or that might be located somewhere in a range of positions, as the basis for determining a distance location for reference. Having found the location of optimal or desired focus on the autofocus target 44, the relative positions of the high optical resolution imaging device objective 24 and the flowcell 22 can be displaced by the recorded displacement distance to provide the optimal or desired focus position for particles in the ribbon-shaped sample stream 32.

According to some embodiments, the high optical resolution imaging device 24 can resolve an image of the ribbon-shaped sample stream 32 as backlighted by a light source 42 applied through an illumination opening (window) 43. In the embodiments shown in FIG. 1, the perimeter of the illumination opening 43 forms an autofocusing target 44. However the object is to collect a precisely focused image of the ribbon-shaped sample stream 32 through high optical resolution imaging device optics 46 on an array of photosensitive elements, such as an integrated charge coupled device.

The high optical resolution imaging device 24 and its optics 46 are configured to resolve an image of the particles in the ribbon-shaped sample stream 32 that is in focus at distance 50, which distance can be a result of the dimensions of the optical system, the shape of the lenses, and the refractive indices of their materials. In some cases, the optimal or desired distance between the high optical resolution imaging device 24 and the ribbon-shaped sample stream 32 does not change. In other cases, the distance between the flowcell 22 and the high optical resolution imaging device and its optics 46 can be changed. Moving the high optical resolution imaging device 24 and/or flowcell 22 closer or further apart, relative to one another (e.g. by adjusting distance 51 between the imaging device 24 and the flowcell 22), moves the location of the focusing point at the end of distance 50 relative to the flowcell.

According to embodiments of the present invention, a focus target 44 can be located at a distance from the ribbon-shaped sample stream 32, in this case fixed directly to the flowcell 22 at the edges of the opening 43 for light from illumination source 42. The focus target 44 is at a constant displacement distance 52 from the ribbon-shaped sample stream 32. Often, the displacement distance 52 is constant because the location of the ribbon-shaped sample stream 32 in the flowcell remains constant.

An exemplary autofocus procedure involves adjusting the relative positions of the high optical resolution imaging device 24 and flowcell 22 using a motor 54 to arrive at the appropriate focal length thereby causing the high optical resolution imaging device 24 to focus on the autofocus target 44. In this example, the autofocus target 44 is behind the ribbon-shaped sample stream 32 in the flowcell. Then the high optical resolution imaging device 24 is moved toward or away from flowcell 22 until autofocus procedures establish that the image resolved on photosensor is an accurately focused image of autofocus target 44. Then motor 54 is operated to displace the relative positions of high optical resolution imaging device 24 and flowcell 22 to cause the high optical resolution imaging device to focus on the ribbon-shaped sample stream 32, namely by moving the high optical resolution imaging device 24 away from flowcell 22, precisely by the span of the displacement distance 52. In this exemplary embodiment, imaging device 24 is shown to be moved by motor 54 to get to a focus position. In other embodiments, flowcell 22 is moved or both the flowcell 22 and imaging device 24 are moved by similar means to obtain focused images.

These directions of movement would of course be reversed if the focus target 44 was located on the front viewport window as opposed to the rear illumination window 43. In that case, the displacement distance would be the span between the ribbon-shaped sample stream 32 and a target 44 at the front viewport (not shown).

The displacement distance 52, which is equal to the distance between ribbon-shaped sample stream 32 and autofocus target 44 along the optical axis of the high optical resolution imaging device 24, can be established in a factory calibration step or established by a user. Typically, once established, the displacement distance 52 does not change. Thermal expansion variations and vibrations may cause the precise position of the high optical resolution imaging device 24 and flowcell 22 to vary relative to one another, thus necessitating re-initiation of the autofocus process. But autofocusing on the target 44 provides a position reference that is fixed relative to the flowcell 22 and thus fixed relative to the ribbon-shaped sample stream 32. Likewise, the displacement distance is constant. Therefore, by autofocusing on the target 44 and displacing the high optical resolution imaging device 24 and flowcell 22 by the span of the displacement distance, the result is the high optical resolution imaging device being focused on the ribbon-shaped sample stream 32.

According to some embodiments, the focusing target is provided as a high contrast circle printed or applied around the illumination opening 43. Alternative focusing target configurations are discussed elsewhere herein. When a square or rectangular image is collected in focus on the target 44, a high contrast border appears around the center of illumination. Seeking the position at which the highest contrast is obtained in the image at the inner edges of the opening automatically focuses the high optical resolution imaging device at the working location of the target 44. According to some embodiments, the term "working distance" can refer to the distance between the objective and its focal plane and the term "working location" can refer to the focal plane of the imaging device. The highest contrast measure of an image is where the brightest white and darkest black measured pixels are adjacent to one another along a line through an inner edge. The highest contrast measure can be used to evaluate whether the focal plane of the imaging device is in the desired position relative to the target 44. Other autofocus techniques can be used as well, such as edge detection techniques, image segmentation, and integrating the differences in amplitude between adjacent pixels and seeking the highest sum of differences. In one technique, the sum of differences is calculated at three distances that encompass working positions on either side of the target 44 and matching the resulting values to a characteristic curve, wherein the optimal distance is at the peak value on the curve. Relatedly, exemplary autofocus techniques can involve collecting images of the flow cell target at different positions and analyzes the images to find the best focus position using a metric that is largest when the image of the target is sharpest. During a first step (coarse) the autofocus technique can operate to find a preliminary best position from a set of images collected at 2.5 µm intervals. From that position the autofocus technique can then involve collecting a second set of images (fine) at 0.5 µm intervals, and calculating the final best focus position on the target.

In some cases, the focus target (autofocus pattern) can reside on the periphery of the area of view in which the sample is to appear. It is also possible that the focus target could be defined by contrasting shapes that reside in the field of view, such at that depicted in FIG. 15. Typically, the autofocus target is mounted on the flowcell or attached rigidly in fixed position relative to the flowcell. Under power of a positioning motor controlled by a detector responsive to maximizing the contrast of the image of the autofocusing target, the apparatus autofocuses on the target as opposed to the ribbon-shaped sample stream. Then by displacing the flowcell and/or the high optical resolution imaging device relative to one another, by the displacement distance known to be the distance between the autofocus target and the ribbon-shaped sample stream, the working position or the focal plane of the high optical resolution imaging device is displaced from the autofocus target to the ribbon-shaped sample stream. As a result, the ribbon-shaped sample stream appears in focus in the collected digital image.

In order to distinguish particle types by data processing techniques, such as categories and/or subcategories of red and white blood cells, it is advantageous to record microscopic pixel images that have sufficient resolution and clarity to reveal the aspects that distinguish one category or subcategory from the others. It is an object of the invention to facilitate autofocus techniques as described.

Figure 1A:
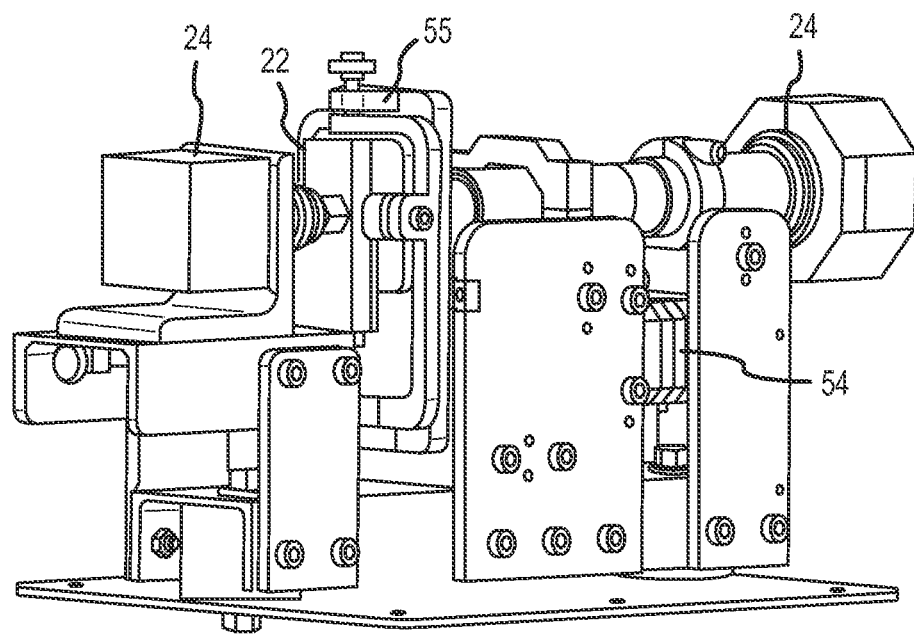
FIGS. 1A and 1B show an optical bench arrangement according to embodiments of the present invention.
Figure 1B:
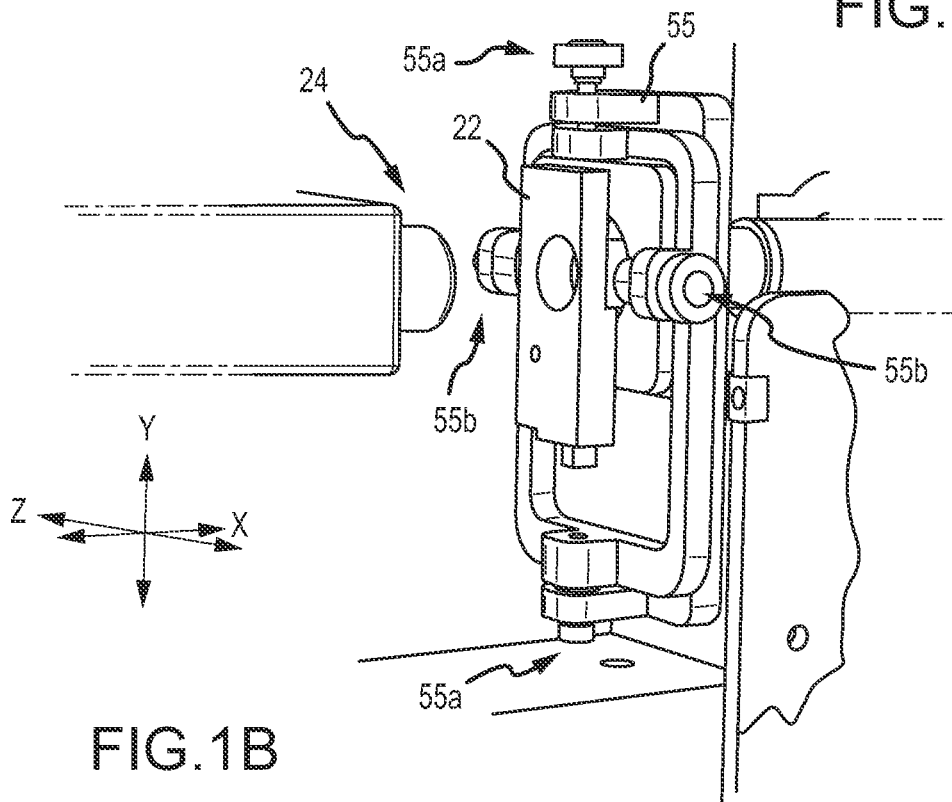

In a practical embodiment, the apparatus can be based on an optical bench arrangement such as shown in FIG. 1A and as enlarged in FIG. 1B, having a source of illumination 42 directed onto a flowcell 22 mounted in a gimbaled or flowcell carrier 55, backlighting the contents of the flowcell 22 in an image obtained by a high optical resolution imaging device 24. Carrier 55 is mounted on a motor drive so as to be precisely movable toward and away from the high optical resolution imaging device 24. Carrier 55 also allows a precise alignment of the flowcell relative to the optical viewing axis of the high optical resolution imaging device or the digital image capture device, so that the ribbon-shaped sample stream flows in a plane normal to the viewing axis in the zone where the ribbon-shaped sample stream is imaged, namely between the illumination opening 43 and viewing port 57 as depicted in FIG. 1. The focus target 44 can assist in adjustment of carrier 55, for example to establish the plane of the ribbon-shaped sample stream normal to the optical axis of the high optical resolution imaging device or the digital image capture device.

Hence, carrier 55 provides for very precise linear and angular adjustment of the position and orientation of flowcell 22, for example relative to the image capture device 24 or the image capture device objective. As shown here, the carrier 55 includes two pivot points 55a, 55b to facilitate angular adjustment of the carrier and flowcell relative to the image capture device. Angular adjustment pivot points 55a, 55b are located in the same plane and centered to the flow cell channel (e.g. at the image capture site). This allows for adjustment of the angles without causing any linear translation of the flow cell position. The carrier 55 can be rotated about an axis of pivot point 55a or about an axis of pivot point 55b, or about both axes. Such rotation can be controlled by a processor and a flowcell movement control mechanism, such as processor 440 and flowcell control mechanism 442 depicted in FIG. 4.

With returning reference to FIG. 1B, it can be seen that either or both of the image capture device 24 and the carrier 55 (along with flowcell 22) can be rotated or translated along various axes (e.g. X, Y, Z) in three dimensions. Hence, an exemplary technique for adjusting focus of the image capture device can include implementing axial rotation of the image capture device 24 about the imaging axis, for example by rotating device 24 about axis X. Focus adjustment can also be achieved by axial rotation of the flowcell 22 and/or carrier 55 about an axis extending along the imaging axis, for example about axis X, and within the field of view of the imaging device. In some cases, focus adjustment may include tip rotation (e.g. rotation about axis Y) of the image capture device. In some cases, focus adjustment may include tip rotation (e.g. rotation about axis Y, or about pivot point 55a) of the flowcell. As depicted here, pivot point 55a corresponds to a Y axis that extends along and within the flowpath of the flowcell. In some cases, focus adjustment can include tilt rotation (e.g. rotation about axis Z) of the image capture device. In some cases, focus adjustment may include tilt rotation (e.g. rotation about axis Z, or about pivot point 55b) of the flowcell. As depicted here, pivot point 55b corresponds to a Z axis that traverses the flowpath and the imaging axis. In some cases, the image capture device can be focused on the sample flowstream by implementing a rotation of the flowcell (e.g. about axis X), such that the rotation is centered in the field of view of the image capture device. The three dimensional rotational adjustments described herein can be implemented so as to account for positional drift in one or more components of the analyzer system. In some cases, the three dimensional rotational adjustments can be implemented so as to account for temperature fluctuations in one or more components of the analyzer system. In some cases, adjustment of an analyzer system may include translating imaging device 24 along axis X. In some cases, adjustment of analyzer system may include translating carrier 55 or flowcell 22 along axis X.

According to some embodiments, a visual analyzer for obtaining images of a sample containing particles suspended in a liquid includes flowcell 22, coupled to a source 25 of the sample and to a source 27 of PIOAL material as depicted in FIG. 1. As seen in the section view of FIG. 3, the flowcell 22 defines an internal flowpath that narrows symmetrically in the flow direction (right to left in FIG. 3 or bottom to top in FIG. 1). The flowcell 22 is configured to direct a flow 32 of the sample enveloped with the PIOAL through a viewing zone in the flowcell, namely behind viewing port 57.

Referring again to FIG. 1, the digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

The autofocus pattern 44, having a position that is fixed relative to the flowcell 22, is located at a displacement distance 52 from the plane of the ribbon-shaped sample stream 32. In the embodiment shown, the autofocus pattern (target 44) is applied directly to the flowcell 22 at a location that is visible in the image collected by the high optical resolution imaging device 24. In another embodiment, the target can be carried on a part that is rigidly fixed in position relative to the flowcell 22 and the ribbon-shaped sample stream 32 therein, if not applied directly to the body of the flowcell in an integral manner.

The light source 42, which can be a steady source or can be a strobe that is flashed in time with operation of the high optical resolution imaging device photosensor, is configured to illuminate the ribbon-shaped sample stream 32 and also to contribute to the contrast of the target 44. In the depicted embodiment, the illumination is from back-lighting.

Figure 1C:
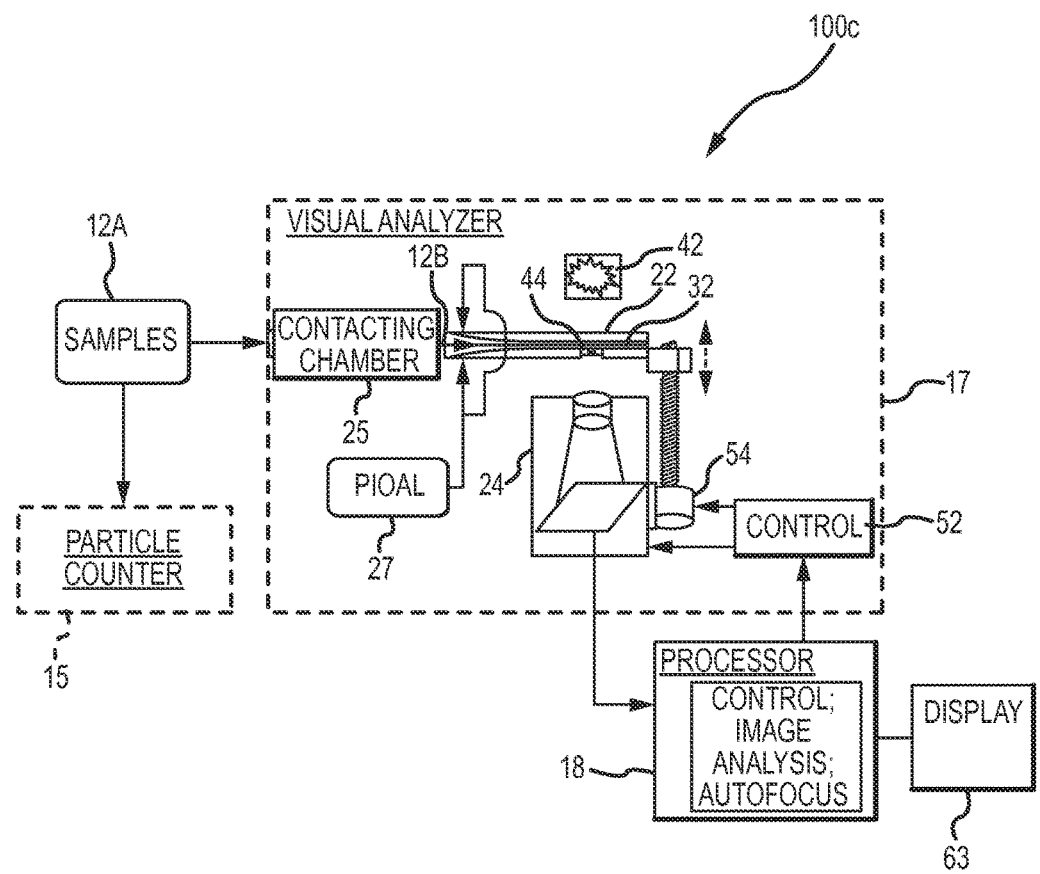
FIG. 1C is a block diagram of a hematology analyzer according to embodiments of the present invention.

FIG. 1C provides a block diagram showing additional aspects of an exemplary hematology analyzer. As shown here, the analyzer 100c includes at least one digital processor 18 coupled to operate the motor drive 54 and to analyze the digitized image from the photosensor array as collected at different focus positions relative to the target autofocus pattern 44. The processor 18 is configured to determine a focus position of the autofocus pattern 44, i.e., to autofocus on the target autofocus pattern 44 and thus establish an optimal distance between the high optical resolution imaging device 24 and the autofocus pattern 44. This can be accomplished by image processing steps such as applying an algorithm to assess the level of contrast in the image at a first distance, which can apply to the entire image or at least at an edge of the autofocus pattern 44. The processor moves the motor 54 to another position and assesses the contrast at that position or edge, and after two or more iterations determines an optimal distance that maximizes the accuracy of focus on the autofocus pattern 44 (or would optimize the accuracy of focus if moved to that position). The processor relies on the fixed spacing between the autofocus target autofocus pattern 44 and the ribbon-shaped sample stream, the processor 18 then controls the motor 54 to move the high optical resolution imaging device 24 to the correct distance to focus on the ribbon-shaped sample stream 32. More particularly, the processor operates the motor to displace the distance between the high optical resolution imaging device and the ribbon-shaped sample stream 32 by the displacement distance 52 (for example as depicted in FIG. 1) by which the ribbon-shaped sample stream is displaced from the target autofocus pattern 44. In this way, the high optical resolution imaging device is focused on the ribbon-shaped sample stream.

The motor 54 can comprise a geared stepping motor with precision somewhat smaller than the distinguishing features imaged by the high optical resolution imaging device or the digital image capture device, especially aspects of blood cells. Provided that the location of the high optical resolution imaging device 24 is adjusted to locate the position of the optical objective within the width of the ribbon-shaped sample stream, the view of the cell/particle in the ribbon-shaped sample stream is in focus. An autofocus pattern 44 can be located at an edge of a field of view of the high optical resolution imaging device or the digital image capture device, and does not interfere with viewing for that reason.

Figure 15:
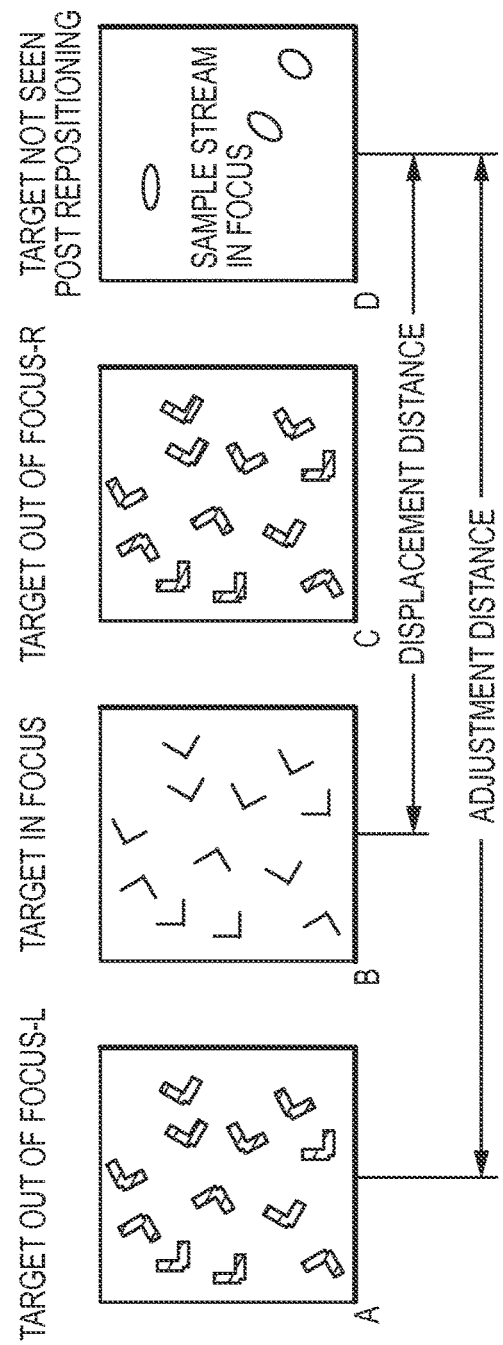
FIG. 15 depicts aspects of autofocus pattern and focusing techniques, according to embodiments of the present invention.

Furthermore, when the high optical resolution imaging device is moved over the displacement distance and the autofocus pattern goes out of focus, the features that appear in focus are the blood cells as opposed to the autofocus pattern. In the embodiment of FIG. 15, for example, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for hematology (blood cell) imaging applications. In some embodiments, the autofocus feature maintains the high optical resolution imaging device within 1 µm of the optimal focus distance.

The flowcell internal contour and the PIOAL and sample flow rates can be adjusted such that the sample is formed into a ribbon shaped stream. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. With returning reference to FIG. 1, the source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. In some cases the PIOAL viscosity can be up to 10 centipoise.

In the embodiment shown in FIG. 1C, the same digital processor 18 that is used to analyze the pixel digital image obtained from photosensor array is also used to control the autofocusing motor 54. However typically the high optical resolution imaging device 24 is not autofocused for every image captured. The autofocus process can be accomplished periodically (at the beginning of the day or at the beginning of a shift) or for example when temperature or other process changes are detected by appropriate sensors, or when image analysis detects a potential need for refocusing. In some cases, an automated autofocusing process may be performed within a time duration of about 10 seconds. In some cases, an autofocus procedure can be performed prior to processing a rack of samples (e.g. 10 samples per rack). It is also possible in other embodiments to have the hematology image analysis accomplished by one processor and to have a separate processor, optionally associated with its own photosensor array, arranged to handle the steps of autofocusing to a fixed target 44.

The digital processor 18 can be configured to autofocus at programmed times or in programmed conditions or on user demand, and also is configured to perform image based categorization and subcategorization of the particles. Exemplary particles include cells, white blood cells, red blood cells and the like.

In one embodiment, the digital processor 18 of FIG. 1 or FIG. 1C is configured to detect an autofocus re-initiation signal. The autofocus re-initiation signal can be triggered by a detected change in temperature, a decrease in focus quality as discerned by parameters of the pixel image date, passage of time, or user-input. Advantageously, it is not necessary to recalibrate in the sense of measuring the displacement distance 52 depicted in FIG. 1 to recalibrate. Optionally, the autofocus can be programmed to re-calibrate at certain frequencies/intervals between runs for quality control and or to maintain focus.

The displacement distance 52 varies slightly from one flowcell to another, but remains constant for a given flowcell. As a setup process when fitting out an image analyzer with a flowcell, the displacement distance is first estimated and then during calibration steps wherein the autofocus and imaging aspects are exercised, the exact displacement distance for the flowcell is determined and entered as a constant into the programming of processor 18.

Figure 1D:
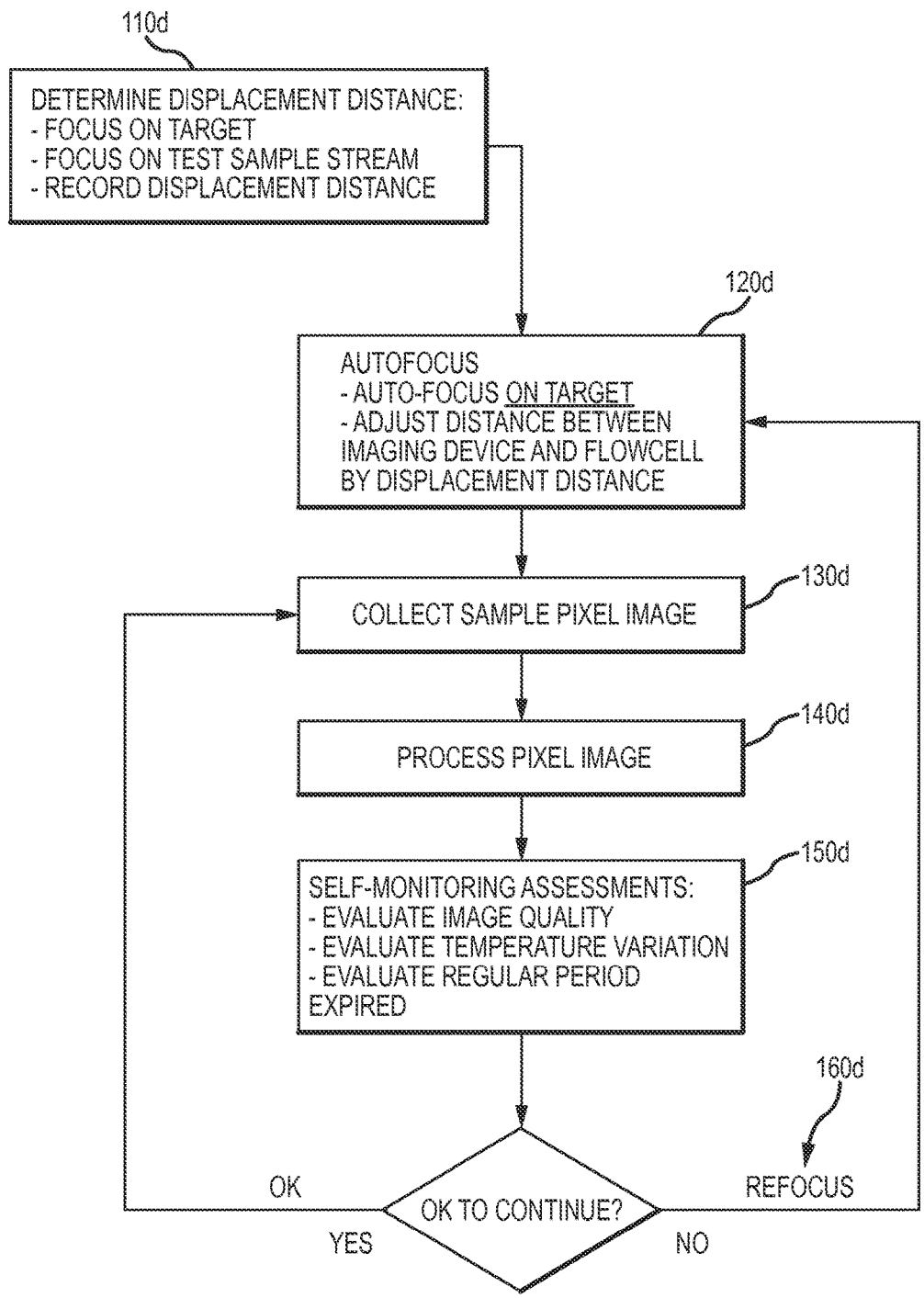
FIG. 1D shows a flowchart of a process according to embodiments of the present invention.

Accordingly, as shown in flowchart form in FIG. 1D, and with reference to hematology analyzer of FIG. 1 and/or FIG. 1C, the process undertaken according to the disclosed methods and apparatus may involve calibrating once or rarely. Calibration can include focusing on the contrast target 44, focusing on the ribbon-shaped sample stream 32, and noting the displacement along the optical axis between these two locations, as indicated in step 110d. That displacement can be noted as a constant. Thereafter by controlling motor 54 and analyzing image data from photosensor array, the processor 18 autofocuses on target 44 and displaces the high optical resolution imaging device 24 and/or flowcell 22 relative to one another by the noted displacement distance, as indicated in step 120d. The ribbon-shaped sample stream 32 is then in focus and its image can be collected (as indicated in step 130d) and processed (as indicated in step 140d) at regular intervals, especially at intervals sufficient to collect substantially non-overlapping adjacent views of portions of the ribbon-shaped sample stream passing through the viewing zone at viewing port 57. When self-monitoring (as indicated in step 150d) reveals a data anomaly or a temperature change that might have altered relative positions of the high optical resolution imaging device 24 and flowcell 22 due to differences in thermal expansion, then autofocus (at indicated in step 160d) is initiated, after which regular operation resumes. Hence, an autofocusing process may include detecting an autofocus re-initiation signal, and repeating autofocusing and image acquisition steps in response to the auto-focus re-initiation signal. In some embodiments the autofocus re-initiation signal can include or be based on change in temperature, a decrease in focus quality, a lapsed time interval, or a user-input.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

It is possible to use autofocusing on the target and displacement by the displacement distance to obtain a distance appropriate for focusing on the ribbon-shaped sample stream. Advantageously, however, autofocusing is not needed or repeated for each image capture. However autofocusing is commenced on certain conditions. An autofocus re-initiation signal can be detected or generated, leading to steps of refocusing on the autofocus pattern, operating the motor drive over the displacement distance, and refocusing the high optical resolution imaging device on the ribbon-shaped sample stream. The autofocus re-initiation signal can be cause by detection of a change for example in temperature, a decrease in focus quality, the passage of time, other process parameters or user-input.

Figure 1E:
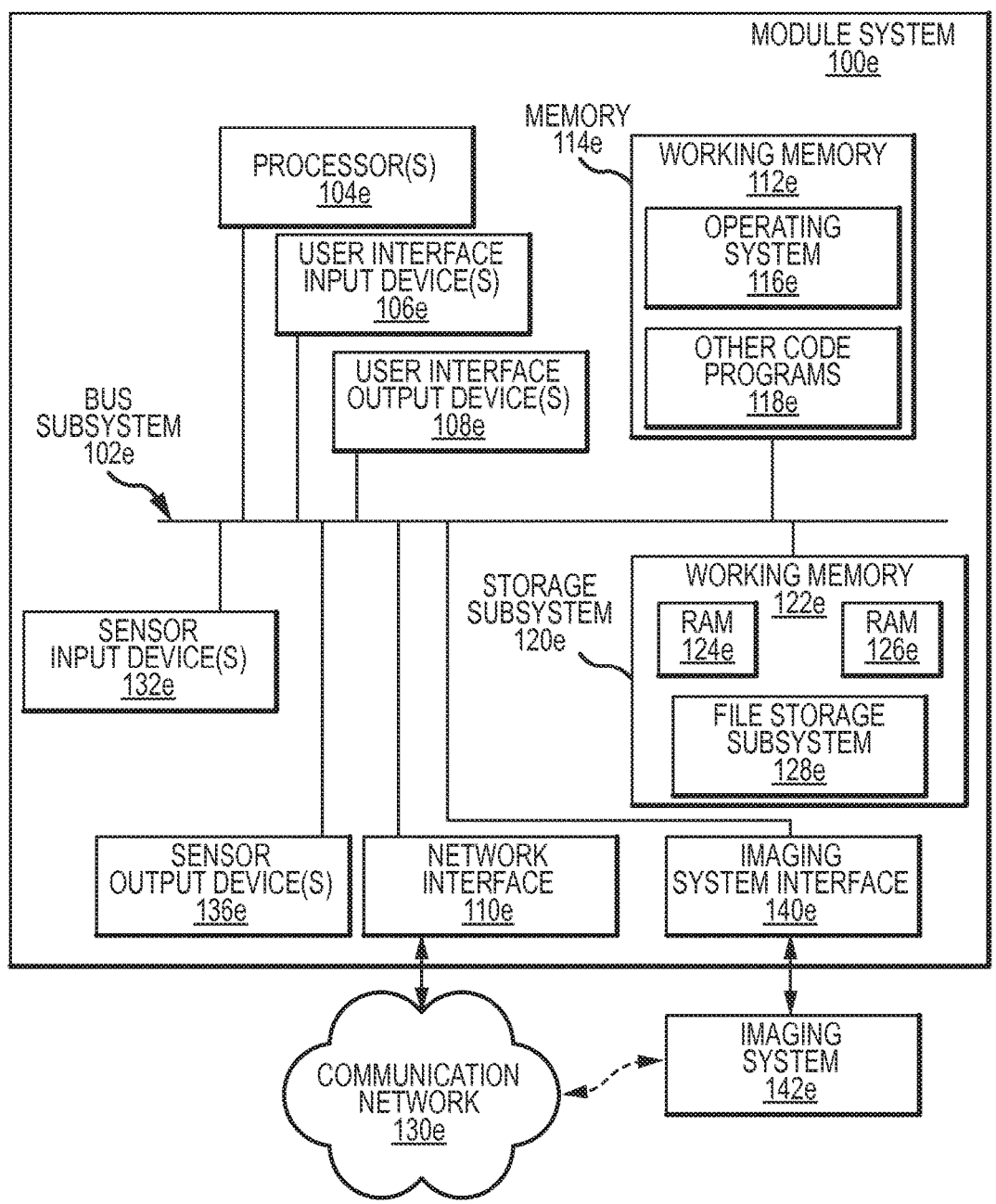
FIG. 1E shows aspects of an exemplary module system according to embodiments of the present invention.

FIG. 1E is a simplified block diagram of an exemplary module system that broadly illustrates how individual system elements for a module system 100e may be implemented in a separated or more integrated manner. Module system 100e may be part of or in connectivity with a particle analysis system for imaging particles in a blood sample fluid, according to embodiments of the present invention. Module system 100e is well suited for producing data or instructions related to focusing and imaging techniques, receiving input related to focusing and imaging techniques, and/or processing information or data related to focusing and imaging techniques, as described elsewhere herein. In some instances, module system 100e includes hardware elements that are electrically coupled via a bus subsystem 102e, including one or more processors 104e, one or more input devices 106e such as user interface input devices, and/or one or more output devices 108e such as user interface output devices. In some instances, system 100e includes a network interface 110e, and/or an imaging system interface 140e that can receive signals from and/or transmit signals to an imaging system 142e. In some instances, system 100e includes software elements, for example shown here as being currently located within a working memory 112e of a memory 114e, an operating system 116e, and/or other code 118e, such as a program configured to implement one or more aspects of the techniques disclosed herein.

In some embodiments, module system 100e may include a storage subsystem 120e that can store the basic programming and data constructs that provide the functionality of the various techniques disclosed herein. For example, software modules implementing the functionality of method aspects, as described herein, may be stored in storage subsystem 120e. These software modules may be executed by the one or more processors 104e. In a distributed environment, the software modules may be stored on a plurality of computer systems and executed by processors of the plurality of computer systems. Storage subsystem 120e can include memory subsystem 122e and file storage subsystem 128e. Memory subsystem 122e may include a number of memories including a main random access memory (RAM) 126e for storage of instructions and data during program execution and a read only memory (ROM) 124e in which fixed instructions are stored. File storage subsystem 128e can provide persistent (non-volatile) storage for program and data files, and may include tangible storage media which may optionally embody sample, patient, treatment, assessment, or other data. File storage subsystem 128e may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 100e. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 128e. In some embodiments, the software or code will provide protocol to allow the module system 100e to communicate with communication network 130e. Optionally, such communications may include dial-up or internet connection communications.

It is appreciated that system 100e can be configured to carry out various aspects of methods of the present invention. For example, processor component or module 104e can be a microprocessor control module configured to receive temperature parameter signals and/or flowcell operational parameters from a sensor input device or module 132e, from a user interface input device or module 106e, and/or from an imaging system 142e, optionally via an image system interface 140e and/or a network interface 110e and a communication network 130e. In some instances, sensor input device(s) may include or be part of a particle analysis system that is equipped to obtain images of blood fluid samples. In some instances, user interface input device(s) 106e and/or network interface 110e may be configured to receive image parameter signals generated by a particle analysis system that is equipped to obtain image parameters. In some instances, imaging system 142e may include or be part of a particle analysis system that is equipped to obtain image parameters related to blood fluid samples.

Processor component or module 104e can also be configured to transmit particle analysis parameter signals or image parameter signals, optionally processed according to any of the techniques disclosed herein, to sensor output device or module 136e, to user interface output device or module 108e, to network interface device or module 110e, to imaging system interface 140e, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 106e may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 106e may also download a computer executable code from a tangible storage media or from communication network 130e, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 100e.

User interface output devices 106e may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user.

Bus subsystem 102e provides a mechanism for letting the various components and subsystems of module system 100e communicate with each other as intended or desired. The various subsystems and components of module system 100e need not be at the same physical location but may be distributed at various locations within a distributed network. Although bus subsystem 102e is shown schematically as a single bus, alternate embodiments of the bus subsystem may utilize multiple busses.

Network interface 110e can provide an interface to an outside network 130e or other devices. Outside communication network 130e can be configured to effect communications as needed or desired with other parties. It can thus receive an electronic packet from module system 100e and transmit any information as needed or desired back to module system 100e. As depicted here, communication network 130e and/or imaging system interface 142e may transmit information to or receive information from an imaging system 142e that is equipped to obtain images or image parameters corresponding to blood fluid samples.

In addition to providing such infrastructure communications links internal to the system, the communications network system 130e may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 100e itself can be of varying types including a computer terminal, a personal computer, a portable computer, a workstation, a network computer, or any other data processing system. Due to the ever-changing nature of computers and networks, the description of module system 100e depicted in FIG. 1E is intended only as a specific example for purposes of illustrating one or more embodiments of the present invention. Many other configurations of module system 100e are possible having more or less components than the module system depicted in FIG. 1E. Any of the modules or components of module system 100e, or any combinations of such modules or components, can be coupled with, or integrated into, or otherwise configured to be in connectivity with, any of the particle analysis and/or imaging system embodiments disclosed herein. Relatedly, any of the hardware and software components discussed above can be integrated with or configured to interface with other medical assessment or treatment systems used at other locations.

In some embodiments, the module system 100e can be configured to receive one or more image parameters of a blood fluid sample at an input module. Image parameter data can be transmitted to an assessment module where diagnostic or other results can be predicted or determined based on analysis of the image data. Image or diagnostic data can be output to a system user via an output module. In some cases, the module system 100e can determine diagnostic results for a blood fluid sample, for example by using a diagnostic module. The diagnostic information can be output to a system user via an output module. Optionally, certain aspects of the diagnosis can be determined by an output device, and transmitted to a diagnosis system or a sub-device of a diagnosis system. Any of a variety of data related to the blood fluid samples or patients from whom samples are obtained can be input into the module system, including age, weight, sex, treatment history, medical history, and the like.

Parameters of treatment regimens or diagnostic evaluations can be determined based on such data.

Relatedly, in some instances a system includes a processor configured to receive the image data as input. Optionally, a processor, storage medium, or both, may be incorporated within a hematology or particle analysis machine. In some instances, the hematology machine may generate image data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Flowcell

Figure 2:
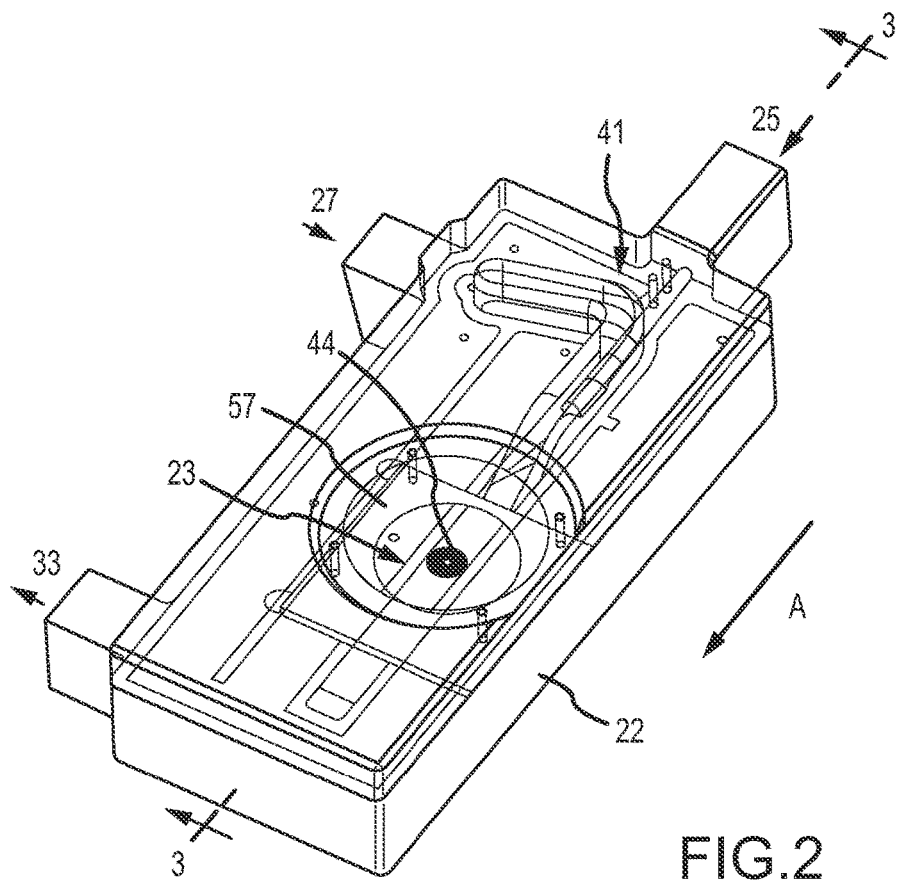
FIG. 2 is a perspective illustration of a flowcell according to an exemplary embodiment.
Figure 3:
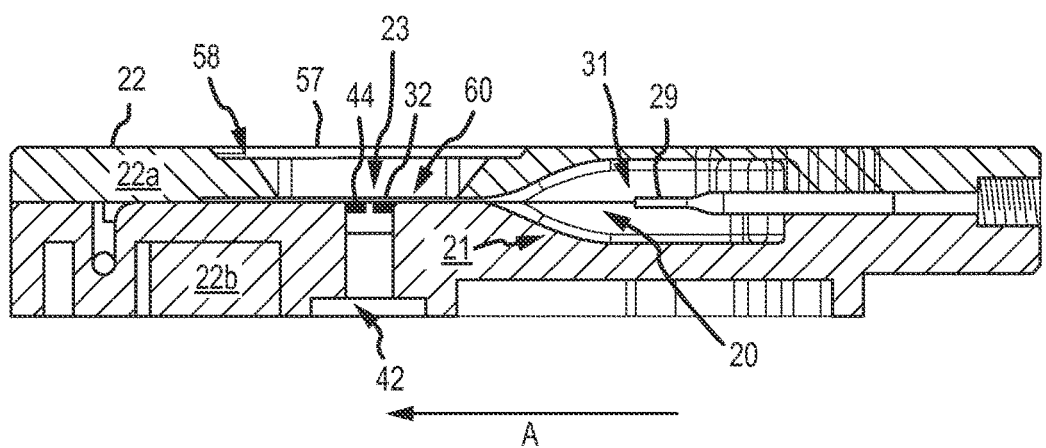
FIG. 3 is a longitudinal median section view along lines 3-3 of the flowcell shown in FIG. 2.

A practical embodiment of flowcell 22 is further depicted in FIGS. 2 and 3. As shown here, flowcell 22 can be coupled with a sample source 25 and also to a source 27 of PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an autofocus pattern 44. Flowcell 22 also has a rounded or recessed seat 58 which is configured to accept or receive a microscope objective (not shown).

According to some embodiments, the autofocus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 µm to about 170 µm. As noted above, the pane 60 can define or form part of the flowpath or sheath (e.g. PIAOL) channel. By using a thin pane 60, it is possible to place the microscope objective very close to the sample fluid ribbon, and hence obtain highly magnified images of particles flowing along the flowpath.

Figure 3A:
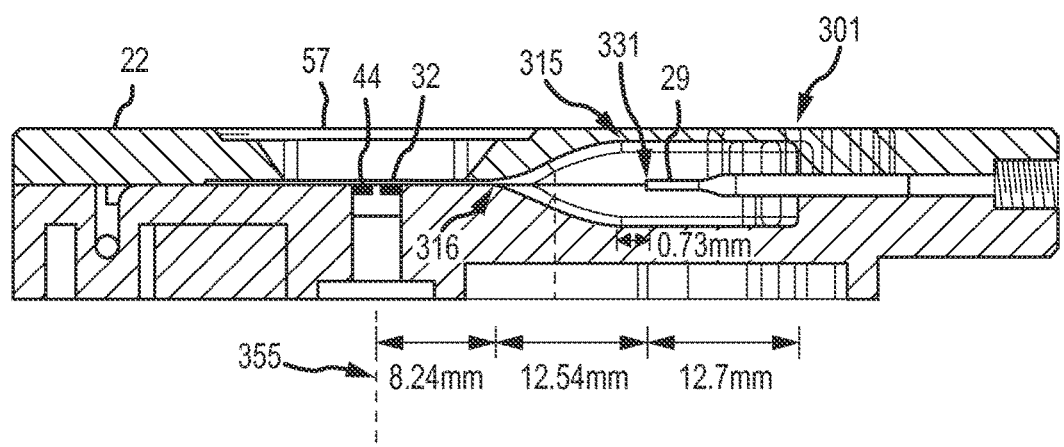
FIGS. 3A and 3B provide additional section views of flowcells according to embodiments of the present invention.
Figure 3B:
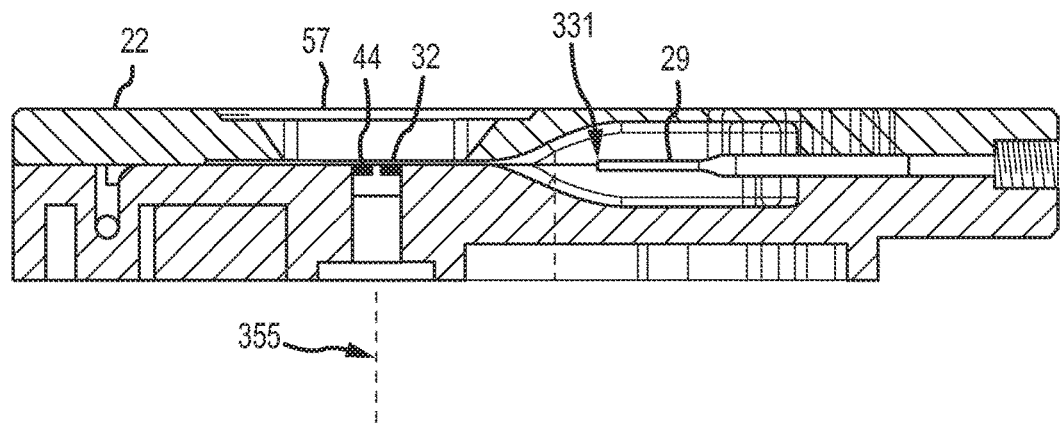

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 µm, and/or the internal flowpath produces a ribbon-shaped sample stream width of 500-3,000 µm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 µm in thickness, and/or the internal flowpath results in the ribbon-shaped sample stream of 2000 µm in width. These dimensions are particularly useful for hematology. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
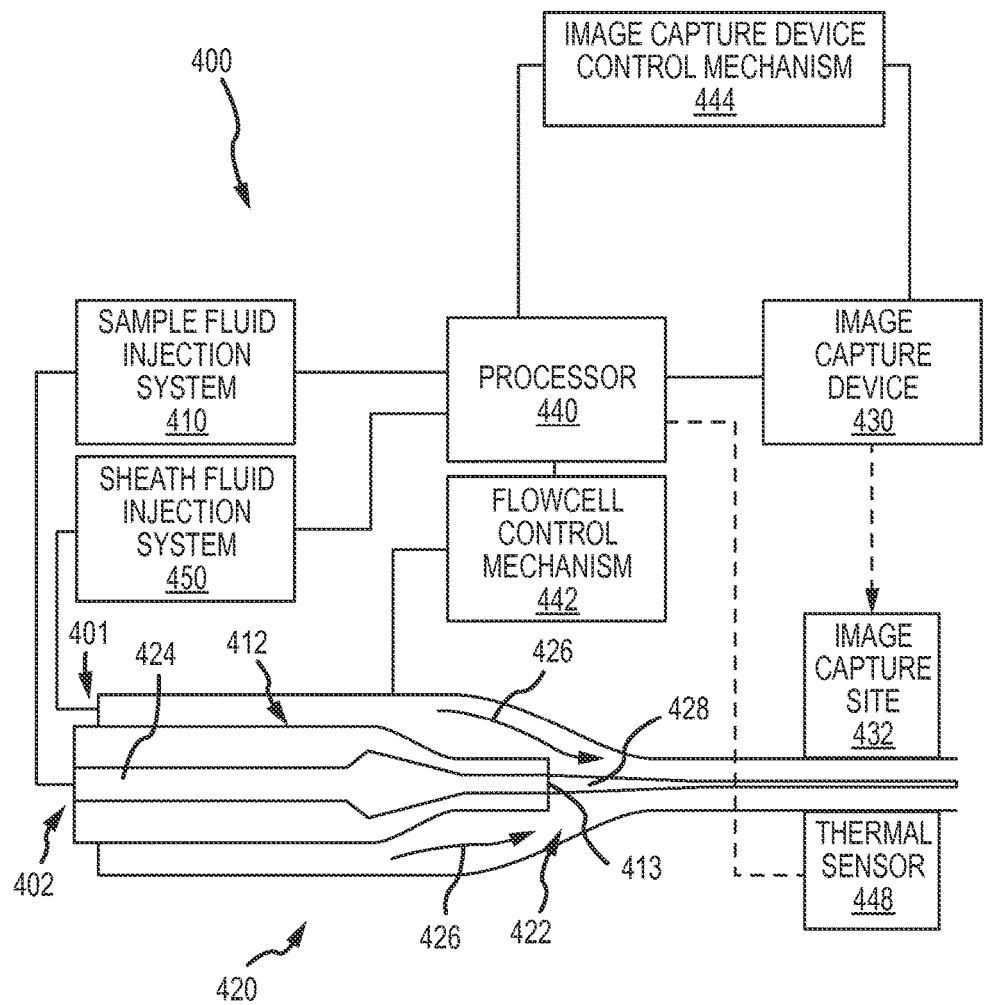
FIG. 4 illustrates aspects of an imaging system according to embodiments of the present invention.

FIG. 4 depicts aspects of a system 400 for imaging particles in a blood fluid sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422, and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450. For example, the processor 440 may include or be in operative association with a storage medium having a computer application that, when executed by the processor, is configured to cause the sheath fluid injection system 450 to inject sheath fluid 426 into the flowcell 420.

The sample fluid stream 428 has a first thickness T1 adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality the particles.

In some embodiments, processor 440 may include or be in operative association with a storage medium having a computer application that, when executed by the processor, is configured to cause a flowcell movement control mechanism 442 to adjust the position of the flowcell 420, for example relative to the image capture device 430. In some embodiments, processor 440 may include or be in operative association with a storage medium having a computer application that, when executed by the processor, is configured to cause an image capture device movement control mechanism 444 to adjust the position of the image capture device 430, for example relative to the flowcell 420. The movement control mechanisms 442, 444 may include motors, gimbals, and other mechanical features that facilitate and produce movement in the flowcell and image capture device, respectively. In some cases, flowcell control mechanism 442 and/or image capture device control mechanism 444 may include a high precision stepper motor control that provides motorized and automated focusing of image capture device relative to the flowcell. As depicted in FIG. 1, a processor can control movement of the image capture device 24. Similarly, as depicted in FIG. 1B, a processor can control movement of a flowcell carrier 55.

Hence, embodiments of the present invention encompass particle analysis systems that perform combined viscosity and geometric hydrofocusing for imaging particles in a blood fluid sample. Exemplary systems can include a flowcell having a flowpath with an injection tube and an imaging window with an imaging axis therethrough. The flowpath of the flowcell can have a decrease in flowpath size. Further, analyzer systems can include a sheath fluid input in fluid communication with the flowpath, and a blood fluid input in fluid communication with the injection tube. The blood fluid input can be configured for injecting the blood fluid sample into the flowing sheath fluid within the flowcell so that the blood fluid sample flows in a sample flowstream with a flowstream width greater than a flowstream thickness. The sheath fluid can have a viscosity that is greater than a viscosity of the blood fluid sample. What is more, the anaylzer system can include an image capture device, and a focusing mechanism that sets a focal state of the image capture device relative to the flowcell. Further, the system can include an imaging target having a position fixed relative to the flowcell, where the imaging target and sample flowstream defining a displacement distance along the imaging axis. The system can also include a processor, and a focusing module having a tangible medium embodying machine-readable code executed on the processor for operating the focusing mechanism to set the focal state of the image capture device, suitable for particle characterization and counting, using the displacement distance. The viscosity difference between the sheath fluid and blood fluid sample, in combination with the decrease in flowpath size, can be effective to hydrofocus the first and second sample fluids at the imaging axis while retaining viability of cells in the blood fluid sample. In some cases, the focusing mechanism can include a drive motor configured to adjust a distance between the image capture device and the flowcell.

In some cases, an analyzer system 400 may include a temperature or thermal sensor 448 that is thermally coupled with the flowcell 420, as depicted in FIG. 4. A focusing module, which may operationally associated with the processor, can include a tangible medium embodying machine-readable code that is executed on the processor for operating a focusing mechanism (e.g. flowcell control mechanism 442 or image capture device control mechanism 444) so as to set the focal state or focal plane of the image capture device, suitable for particle characterization and counting, in response to a change in temperature sensed by the temperature sensor and a known relationship between temperature and a desired focus.

Figure 4A:
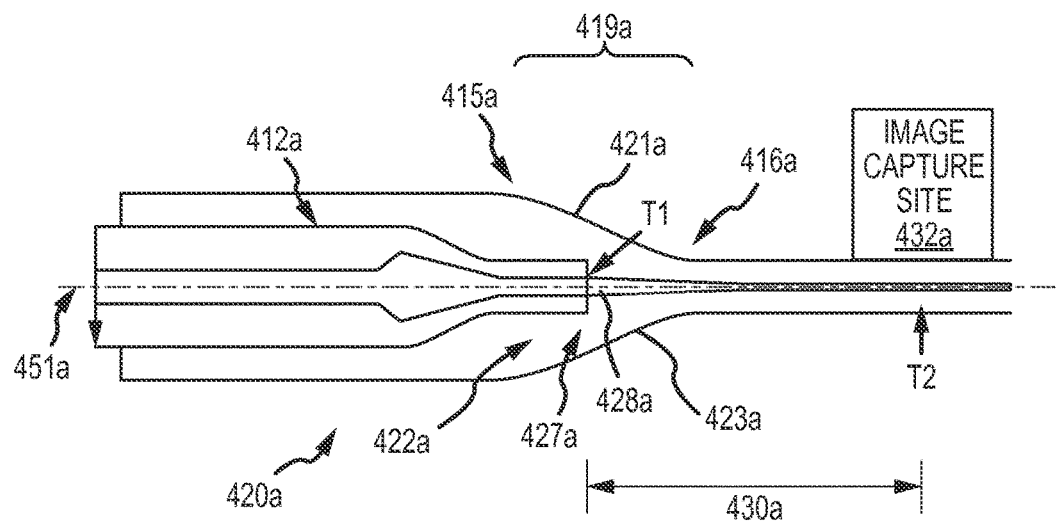
FIGS. 4A and 4B depict aspects of flowcells according to embodiments of the present invention.

As shown in the flowcell embodiment depicted in FIG. 4A, a decrease in flowpath size (e.g. at transition zone 419a) can be defined by opposed walls 421a, 423a of the flowpath 422a. The opposed walls 421a, 423a can angle radially inward along the flowpath 422a, generally symmetric about a transverse plane 451a that bisects the sample fluid stream 428a. The plane 451a can bisect the sample stream 428a where the sample stream has a first thickness T1, at a location where the sample stream 428a exits a distal portion 427a of the cannula or sample injection tube 412a. Similarly, the plane 451a can bisect the sample stream 428a where the sample stream has a second thickness T2, at a location where the sample stream 428a passes the image capture site 432a. According to some embodiments, the first thickness T1 has a value of about 150 µm and the second thickness T2 has a value of about 2 µm. In such cases, the compression ratio of the sample ribbon stream is 75:1. According to some embodiments, the first thickness T1 has a value within a range from about 50 µm to about 250 µm and the second thickness T2 has a value within a range from about 2 µm to about 10 µm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon.

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430a between the distal cannula portion 427a and the image capture site 432a. According to some embodiments, the distal portion 427a of the sample fluid injection tube 412a can be positioned at an axial separation distance 430a from the image capture site 432a, where the axial separation distance 432a has a value of about 21 mm. In some cases, the axial separation distance 430a has a value within a range from about 16 mm to about 26 mm.

The axial separation distance 430a between the cannula exit port and image capture site can impact the transition time for the sample fluid as the fluid travels from the exit port to the image capture site. For instance, a relatively shorter axial separation distance 430a can contribute to a shorter transition time, and a relatively longer axial sepration distance 430a can contribute to a longer transition time.

The position of the exit port at the cannula distal portion 427a relative to the flowpath transition zone 419a, or relative to the proximal portion 415a of the flowpath transition zone 419a, can also inference the transition time for the sample fluid as the fluid travels from the exit port to the image capture site. For example, the sheath fluid may have a relatively slower speed at the proximal portion 415a, and a relatively faster speed at a location between the proximal portion 415a and the distal portion 416a. Hence, if the cannula exit port at distal portion 427a is positioned at the proximal portion 415a, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415a) of the flowcell, the longer it takes the sample to reach the image capture site. Conversely, if the cannula exit port at distal portion 427a is positioned distal to the proximal portion 415a (e.g. at a central location between proximal portion 415a and distal portion 416a, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419a, due to the narrowing cross-sectional area of the zone 419a.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amoutn of time (e.g. images per minute).

Although there are advantages associated with positioning the exit port of the cannula distal portion 427a more closely to the image capture site 432a, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficient stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427a of the sample fluid injection tube 412a can be positioned distal to a proximal portion 415a of the flowpath transition zone 419a. Relatedly, the downstream end 427a of the sample fluid injection tube 412a can be positioned proximal to a distal portion 416a of the flowpath transition zone 419a. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the blood fluid sample. For example, such symmetry can be effective to limit red blood cells imaging orientation misalignment in the blood fluid sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 150 μm×150 μm and 400 μm×400 μm. In some cases, the image capture site 432a has a field of view 433a of about 275 μm×275 μm. In some cases, the field of view can be defined in terms of length times width. If expressed as surface area, a 275 μm×275 μm field of view has an area of 75,625 μm$^2$. According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

FIGS. 4A-1 and 4A-2 illustrate the effects of hydrofocusing on the sample stream as it travels from the cannula exit port to the image capture site. As shown in FIG. 4A-1, the sample stream can have a height H(S) of about 150 μm and a width W(S) of about 1350 μm. Further, the PIOAL sheath stream can have a height H(P) of about 6000 μm and a width W(P) of about 4000 μm. Subsequent to the hydrofocusing, as shown in FIG. 4A-2, the sample stream can have a height H(S) of about 2 μm and a width W(S) of about 1350 μm. Further, the PIOAL sheath stream can have a height H(P) of about 150 μm and a width W(P) of about 4000 μm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 μm and a width W(P) of about 4000 μm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 μL/second. The volumetric flow rate of sample fluid at the imaging area can be about 0.232 μL/second. In some cases, the cross-sectional area of the combined sheath and sample streams at the imaging site is 600,000 μm$^2$. In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 μL/s and the fluid sample can flow at a fluid sample volumetric flow rate of 0.232 µL/s (or within a range from 0.2 to 0.35 µL/s). In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath fluid and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

Figure 4B:
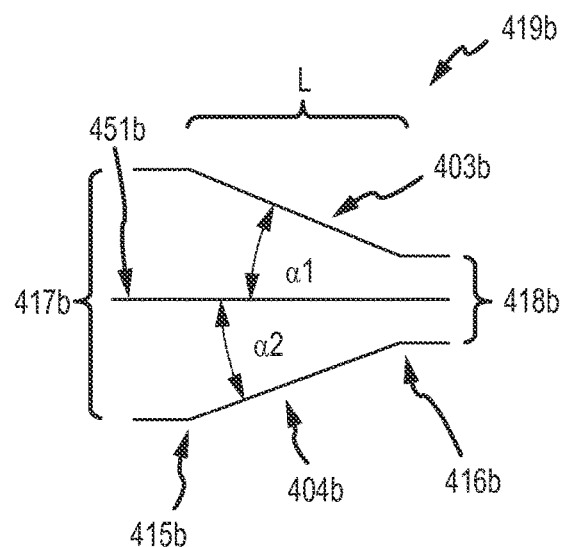
Figures 1, 4A:
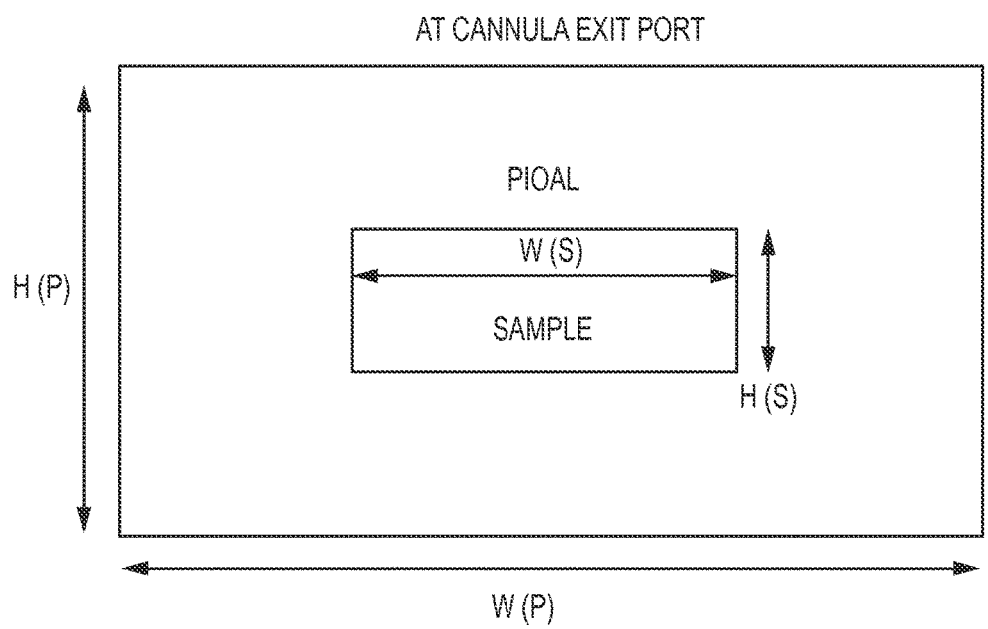
Figures 2, 4A:
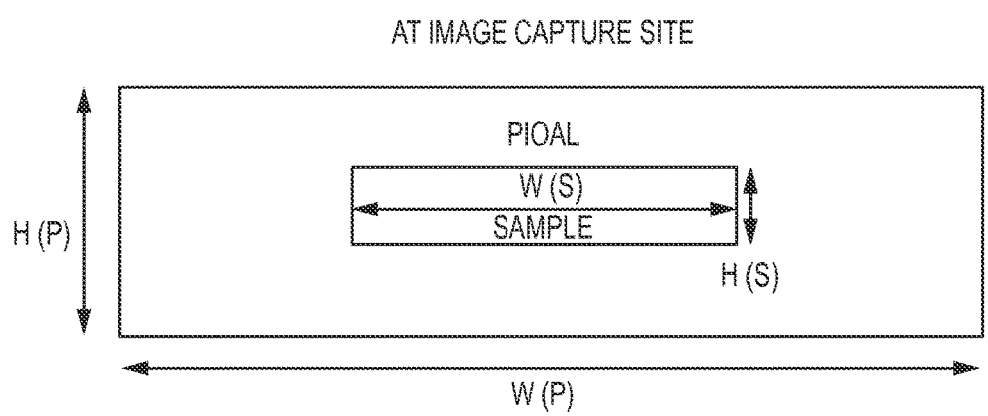

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial view of FIG. 4B, the transition zone 419b of the flowpath can have a length L between a proximal portion 415b and a distal portion 416b, where the proximal portion 415b has a proximal height 417b, and the distal portion 416b has a distal height 418b. As noted elsewhere herein, the shape or contour of the transition zone can be curved or smooth, and for example can be provided in the shape of an S-curve or a tangent curve. According to some embodiments, the proximal height 417b has a value of about 6000 µm. In some cases, the proximal height 417b has a value within a range from about 3000 µm to about 8000 µm. According to some embodiments, the distal height 418b has a value of about 150 µm. In some cases, the distal height 418b has a value within a range from about 50 µm to about 400 µm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figure 4K:
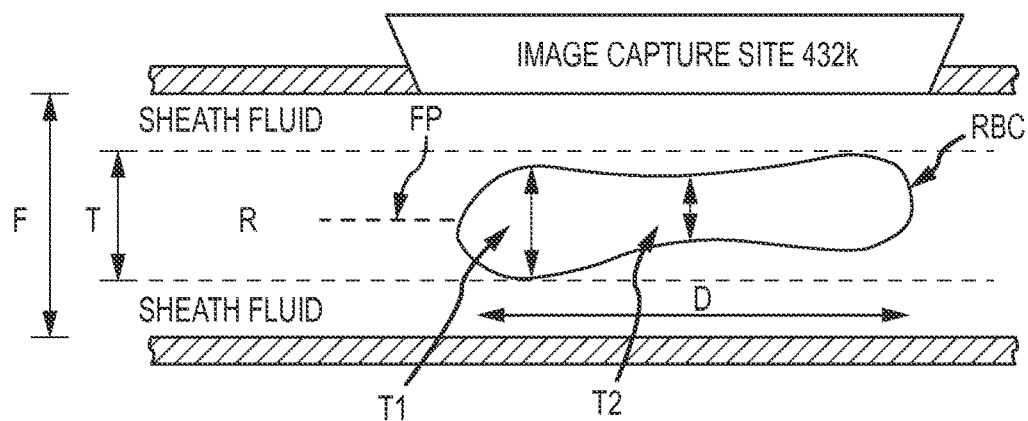
FIGS. 4K and 4L show a sample stream flowing through an image capture site of a flowcell according to embodiments of the present invention.

As shown in FIG. 4K, a sample stream ribbon R flowing through an image capture site 432k of a flowcell 420k can have a thickness T of about 2 µm. In some cases, thickness T of the sample stream ribbon can be up to about 3 µm. Typically, cells or particles that are smaller than the sample stream thickness will be contained within the ribbon. An exemplary red blood cell (RBC) can be present as a biconcave disk and can have a diameter D of between about 6.2 µm and about 8.2 µm. Further, an exemplary red blood cell can have a maximum thickness T1 of between about 2 µm and about 2.5 µm and a minimum thickness T2 of between about 0.8 µm and about 1 µm. In some cases, red blood cells can have a thickness of up to about 3 µm. Exemplary human platelets can vary in size, and can also have a thickness or diameter of about 2 µm. Although not shown to scale here, the flowcell can define a flow path thickness H having a value of about 150 µm, at the image capture site. In some cases, the flowpath thickness F has a value between 50 µm and 400 µm. This flowpath thickness F can also correspond to the distal height 418b of distal portion 461b depicted in FIG. 4B.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 µm to 5 µm. A viscosity differential between the sheath fluid and the sample fluid can be selected so as to achieve a desired positioning of the ribbon sample stream within the flowcell.

As discussed elsewhere herein, as well as in co-pending U.S. patent application Ser. No. 14/215,834, filed Mar. 17, 2014, viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the blood fluid sample. For example, viscosity differentials can be effective to limit red blood cells imaging orientation misalignment in the blood fluid sample to less than about 10%. That is, 90 or more red blood cells out of 100 red blood cells in a sample can be aligned so that their major surfaces face toward the imaging device. A symmetrical narrowing transition zone can provide a value of 20%. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14/216,533, filed Mar. 17, 2014, the content of which is incorporated herein by reference.

Figure 4L:
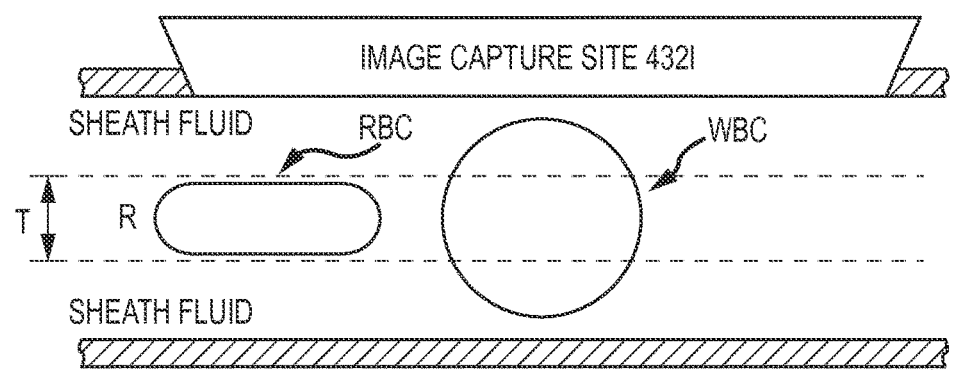
Figures 1, 4K:
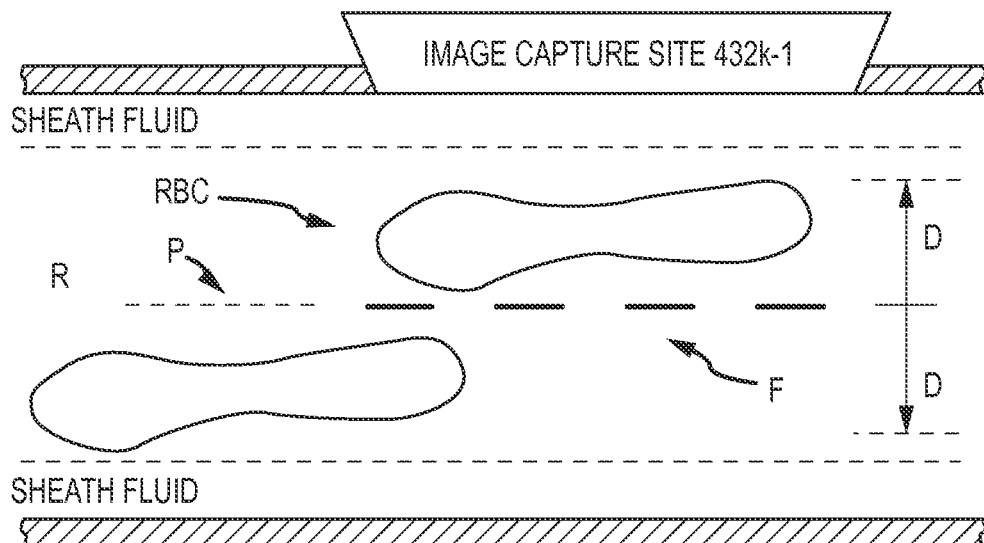
Figures 2, 4K:
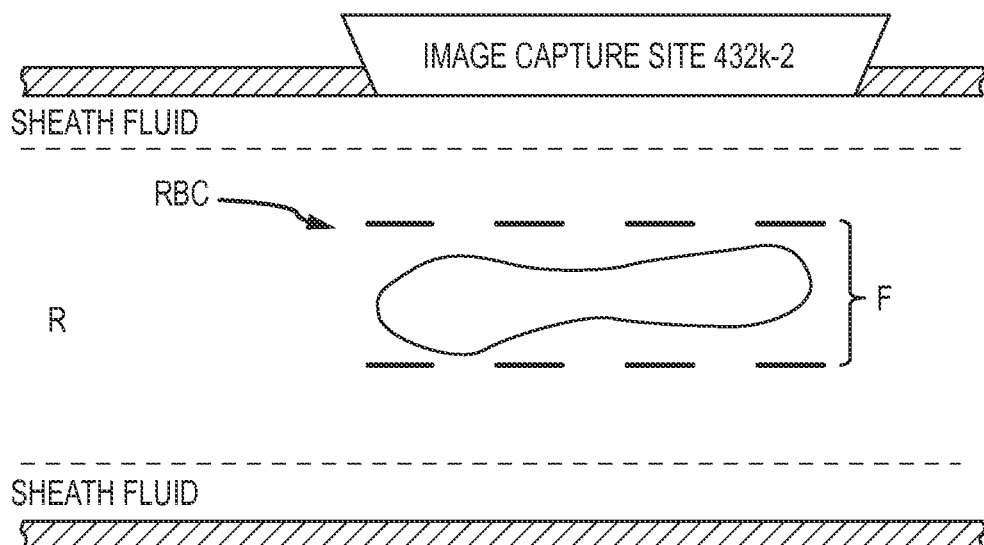
Figures 3, 4K:
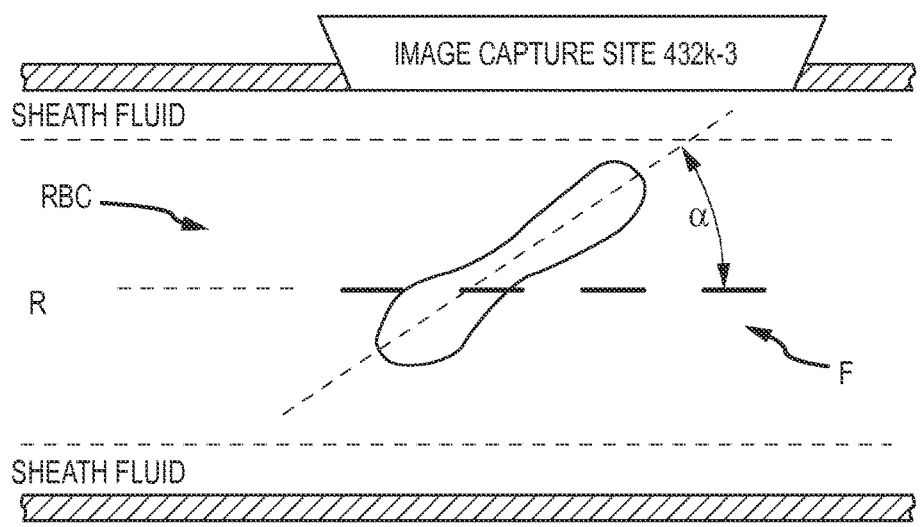

White blood cells are typically larger than red blood cells and platelets. For example, exemplary neutrophils and eosinophils can have a diameter of between about 10 µm and about 12 µm. Exemplary basophils can have a diameter of between about 12 µm and about 15 µm. Exemplary lymphocytes (small) can have a diameter of between about 7 µm and about 8 µm, and exemplary lymphocytes (large) can have a diameter of between about 12 µm and about 15 µm. Exemplary monocytes can have a diameter of between about 12 µm and about 20 µm. The configuration of the particle analysis system, including interaction between the sheath fluid and the fluid sample ribbon as they pass through the flowcell, can operate to compress white blood cells as they travel through the image capture site 432l, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid. The numerical values or ranges for the thickness T of sample stream ribbon R, and the thickness F of the flowpath as discussed above with regard to FIG. 4K are similarly applicable to FIG. 4L.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

As depicted in FIG. 4L, portions of a cell such as a white blood cell can extend into the sheath fluid. Embodiments of the present invention encompass sheath fluid compositions that do not lyse or shred the cell, or otherwise compromise the integrity of the outer cell membrane, when the cell is exposed to the sheath fluid. A viscosity agent in the sheath fluid can operate to retain viability of cells in the sample fluid stream, so as to leave the structure (e.g. shape) and the content (e.g. nucleus) of the cells intact when the cell membrane or wall traverses an interface between the sample fluid ribbon and the sheath fluid envelope or otherwise extends from the sample fluid stream into the flowing sheath fluid.

Often, there are compressive forces acting upon the cells or particles as they flow within the sample fluid ribbon along the flowcell. Hence, the cells may come into contact with the sheath fluid while the cells are in a compressed state or are otherwise subject to compressive forces as a result of a narrowing transition zone. The viscosity agent of the sheath fluid can operate to protect the compressed cells from being shredded or destroyed when they emerge from the thin sample fluid ribbon and become exposed to the viscous sheath fluid, at least until the cells reach the image capture site. Hence, the viscosity agent composition of the sheath fluid can operate as a cellular protectorant, while also enhancing alignment of the particles or intraparticle content.

With reference to FIGS. 4K and 4L, in some instances portions of the cell or particle may extend out of the thin sample fluid ribbon R and into the surrounding sheath fluid. As discussed in co-pending U.S. patent application Ser. No. 14/215,834, filed Mar. 17, 2014, the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sampel fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

As noted elsewhere herein, and with reference to FIGS. 4K and 4L, as the sheath fluid and the sample fluid R flow through a reduction in flowpath size or transition zone of a flowcell, and toward an imaging site 432k or 432l, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site 432k or 432l.

In some cases, the target imaging state is a target orientation relative to a focal plane F at the imaging site. For example, as depicted in FIG. 4K-1, the particle (RBC) can be displaced at a distance from the focal plane F. In some cases, the target orientation involves a target particle orientation relative to the focal plane F at the imaging site 432k-1. The particle can be a blood cell, such as a red blood cell, a white blood cell, or a platelet. As shown here, the flowpath at the imaging site 432k-1 can define a P plane that is substantially parallel to or coplanar with the focal plane F. In some cases, a portion of the particle may be positioned along the focal plane F, yet the central portion of the particle may otherwise be offset from the focal plane F. In some cases, the target orientation involves a target position relative to the focal plane F at the imaging site 432k-1. For example, the target position may involve positioning of the particle so that at least a portion of the particle is disposed along the focal plane F. In some cases, the target position may involve positioning of the particle so that a distance between the particle and the focal plane F does not exceed a certain threshold. In some cases, the target position involves a target particle position that is relative to the focal plane F at the imaging site 432k-1. In some cases, the target position is at or less than a distance D from the focal plane F, where distance D corresponds to a positional tolerance. A viscosity differential between the sheath fluid and the sample fluid can be selected so as to achieve a desired positioning of the ribbon sample stream within the flowcell (e.g. relative to flowpath plane P and/or focal plane F). In some cases, the viscosity differential can be selected so as to achieve a target particle position that is at or less than the positional tolerance D.

In some cases, the focal plane F has a thickness or depth of field as indicated in FIG. 4K-2, and the particle (RBC) has a target imaging state relative to the focal plane thickness. For example, the target position for the particle can be within the focal plane F or at least partially within the focal plane F. In some cases a high optical resolution imaging device or camera can have a depth of field or focal plane thickness of about 7 μm. In some cases, the depth of field or focal plane thickness has a value with a range from about 2 μm to about 10 μm. In some cases, the depth of the field of the camera is similar or equal to the sample ribbon thickness at the image capture site.

In some cases, the target orientation can involve a target alignment relative to the focal plane F at the imaging site. For example, the target alignment can indicate that a plane defined by the particle is aligned with the focal plane F, not to exceed a certain angle α relative to the focal plane F at the image capture site 432k-3 as shown in FIG. 4K-3. In some cases, the target imaging state can involve a limitation on the number or percentage of misaligned particles in a sample. For example, a difference in viscosity between the sheath fluid and the sample fluid R can be effective to limit red blood cells imaging orientation misalignment in the blood fluid sample to less than about 10%. That is, 90 or more red blood cells out of 100 red blood cells in a sample can be aligned so that their major surfaces face toward the imaging device (as depicted in FIGS. 4K-1 and 4K-2) or so that the alignment of those 90 or more RBCs is within 20 degrees from a plane substantially parallel to the direction of flow (e.g. RBC alignment angle α is 20 degrees or less). As discussed elsewhere herein, in some cases at least 92% of non-spherical particles such as RBCs can be aligned in a plane substantially parallel to the direction of flow. In some cases, at least between 75% and 95% of non-spherical particles such as RBCs can be substantially aligned, namely within 20 degrees from a plane substantially parallel to the direction of flow (e.g. alignment angle α is 20 degrees or less). According to some embodiments, 90% or more of certain particles (e.g. red blood cells and/or platelets) can be oriented transverse to the imaging axis of the imaging device.

In some cases, embodiments of the present invention include compositions for use with a hematology system as described herein, such as a sheath fluid or particle and intracellular organelle alignment liquid (PIOAL). Such sheath fluids or PIOALs are suitable for use in a combined viscosity and geometric hydrofocusing visual analyzer. The PIOAL can operate to direct or facilitate flow of a blood sample fluid of a given viscosity through a narrowing flowcell transition zone of the visual analyzer. The PIOAL can include a fluid having a higher viscosity than the viscosity of the sample. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, can be effective to provide a target imaging state in at least some of the plurality of particles at an imaging site of the visual analyzer while retaining viability of cells in the blood sample fluid.

Figure 4M:
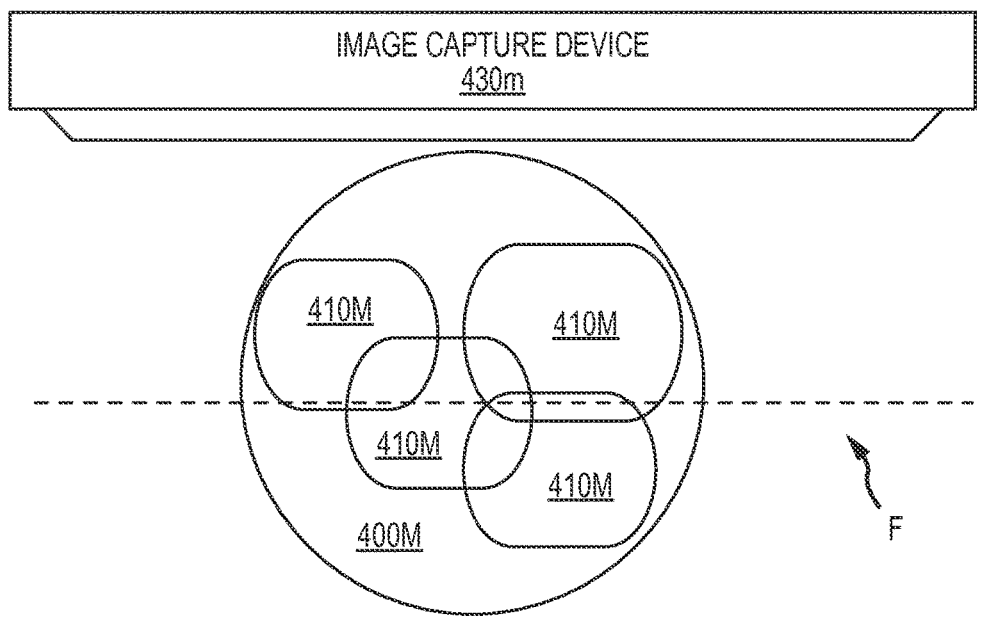
FIGS. 4M and 4N show exemplary intracellular particle alignment features according to embodiments of the present invention.
Figure 4N:
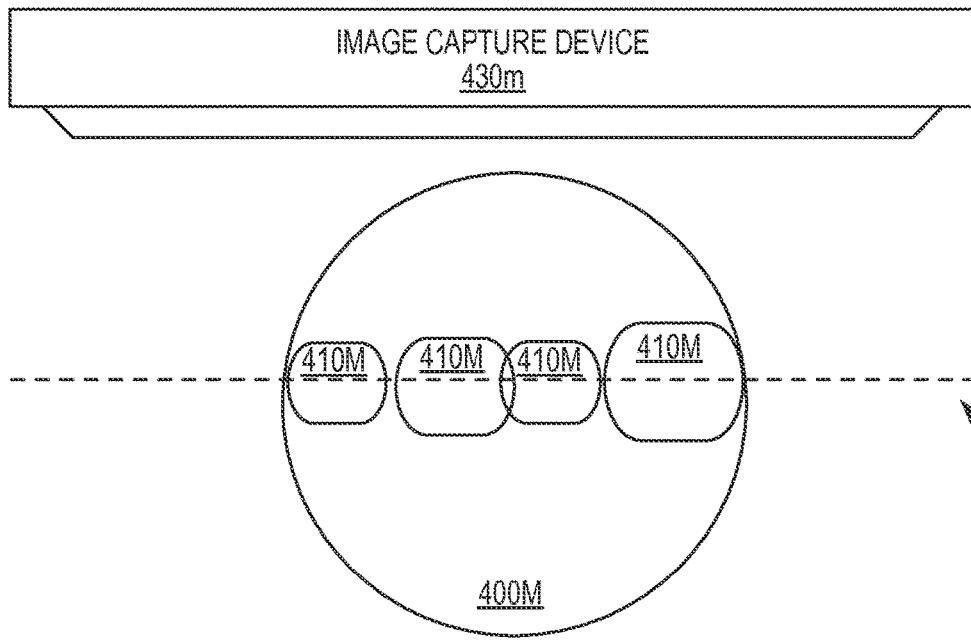

FIG. 4M depicts an exemplary neutrophil 400*m* (a type of white blood cell) having internal organelles such as lobes 410*m*. As a result of the viscosity differential between the sample fluid and the sheath fluid, the internal organelles can align within the cell, as indicated by FIG. 4N. Hence, the intracellular organelles can be effectively imaged with an image capture device 430*m*, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids. Accordingly, enhanced imaging results corresponding to cell alignment and in-focus are achieved using the viscosity differential, hydrodynamic flow, and geometric compression features.

As noted elsewhere herein, and with reference to FIGS. 4M and 4N, as the sheath fluid and the sample fluid R flow through a reduction in flowpath size or transition zone of a flowcell, and toward an imaging site of an image capture device 430*m* or 430*n*, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site. According to some embodiments, the target imaging state may correspond to a distribution of imaging states.

In some cases, the target imaging state can involve a target intraparticle structure orientation (e.g. alignment and/or position) relative to a focal plane at the imaging site. For example, as depicted in FIG. 4N, the internal structures 410*m* (e.g. intracellular structure, organelle, lobe, or the like) can be oriented relative to the focal plane F. In some cases, the target alignment involves a target intraparticle structure alignment relative to a focal plane F at the imaging site, similar to the particle alignment relationship depicted in FIG. 4K-3. In some cases, the target position involves a target intraparticle structure position relative to a focal plane at the imaging site, similar to the particle position relationship depicted in FIG. 4K-1. In some cases, the target orientation of the intraparticle structure can include both a target alignment relative to the focal plane and also a target position relative to the focal plane. In some cases, the target imaging state can involve a target deformation at the imaging site. For example, as depicted in FIG. 4N, the particle 400*m* has a compressed shape as compared to the particle shape depicted in FIG. 4M. Hence, it can be seen that operation of the flowcell can produce a lateral compression effect on the particle shapes. Relatedly, the intraparticle features can be positionally or directionally oriented (e.g. aligned with respect to the focal plane F and/or ribbon flow plane) as the particle itself is compressed in shape. According to some embodiments, a velocity difference between the sheath and sample fluids can produce friction within the flowstream, and a viscosity difference between the sheath and sample fluids can amplify that hydrodynamic friction.

Any of a variety of hematology or blood particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flowcell can support a 5-part WBC differential test. In some cases, images obtained using the flowcell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. For example, diagnostic or testing techiques can be used to differentiate various cells (e.g. neutrophils, lymphocytes, monocytes, eosinophils, basophils, metamyelocytes, myelocytes, promyelocytes, and blasts).

Methods

Figure 5:
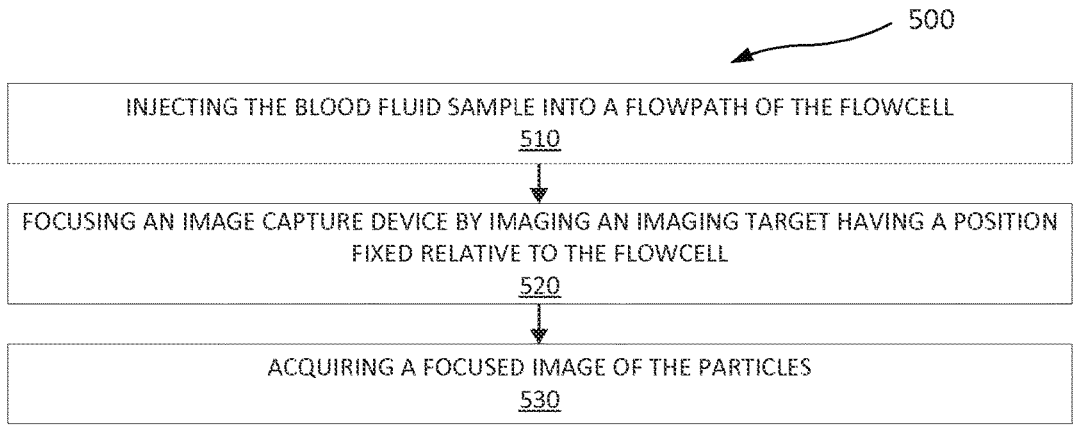
FIG. 5 illustrates aspects of a focusing technique according to embodiments of the present invention.

FIG. 5 depicts aspects of an exemplary method 500 for imaging particles in a blood fluid sample, according to embodiments of the present invention. Method 500 can include injecting a blood fluid sample into a flowpath of the flowcell, as indicated by step 510. The method may also include focusing an image capture device by imaging an imaging target having a position fixed relative to the flowcell, as indicated by step 520. Further, the method may include acquiring a focused image of the particles, as indicated by step 530. The focused image can be suitable for particle characterization and counting, within the flowstream with the image capture device, wherein the image capture device is focused on the sample flowstream using a displacement distance.

Figure 6:
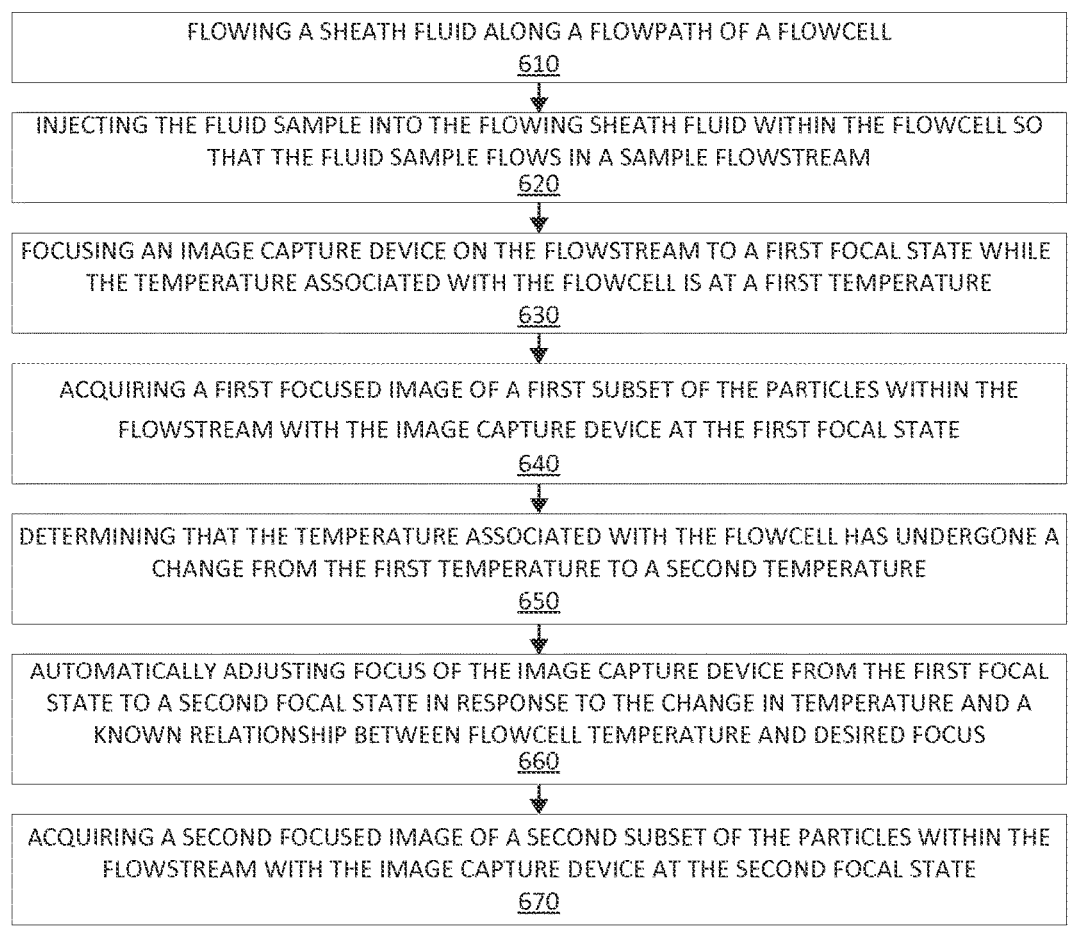
FIG. 6 illustrates aspects of a focusing technique according to embodiments of the present invention.

FIG. 6 depicts aspects of an exemplary method for imaging particles in a blood fluid sample. As shown here, method 600 can flowing a sheath fluid along a flowpath of a flowcell as indicated by step 610, injecting the fluid sample into the flowing sheath fluid within the flowcell so that the fluid sample flows in a sample flowstream as indicated by step 620, focusing an image capture deviceon the flowstream to a first focal state while the temperature associated with the flowcell is at a first temperature as indicated by step 630, acquiring a first focused image of a first subset of the particles within the flowstream with the image capture device at the first focal state as indicated by step 640, determining that the temperature associated with the flowcell has undergone a change from the first temperature to a second temperature as indicated by step 650, automatically adjusting focus of the image capture device from the first focal state to a second focal state in response to the change in temperature and a known relationship between flowcell temperature and desired focus as indicated by step 660, and acquiring a second focused image of a second subset of the particles within the flowstream with the image capture device at the second focal state as indicated by step 670.

Shear Strain Rate

Figure 7:
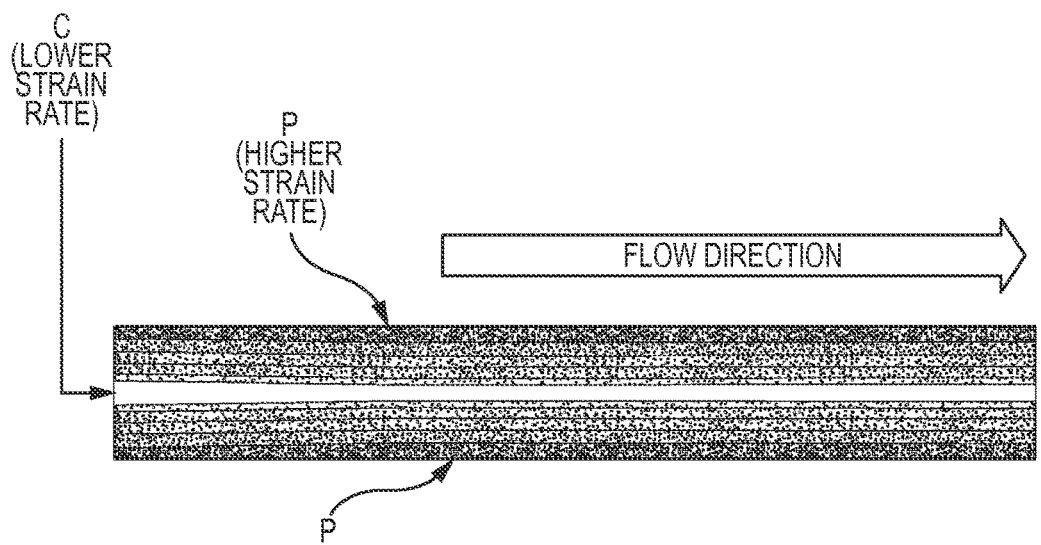
FIGS. 7 and 8 depict aspects of flowstream strain rate according to embodiments of the present invention.
Figure 8:
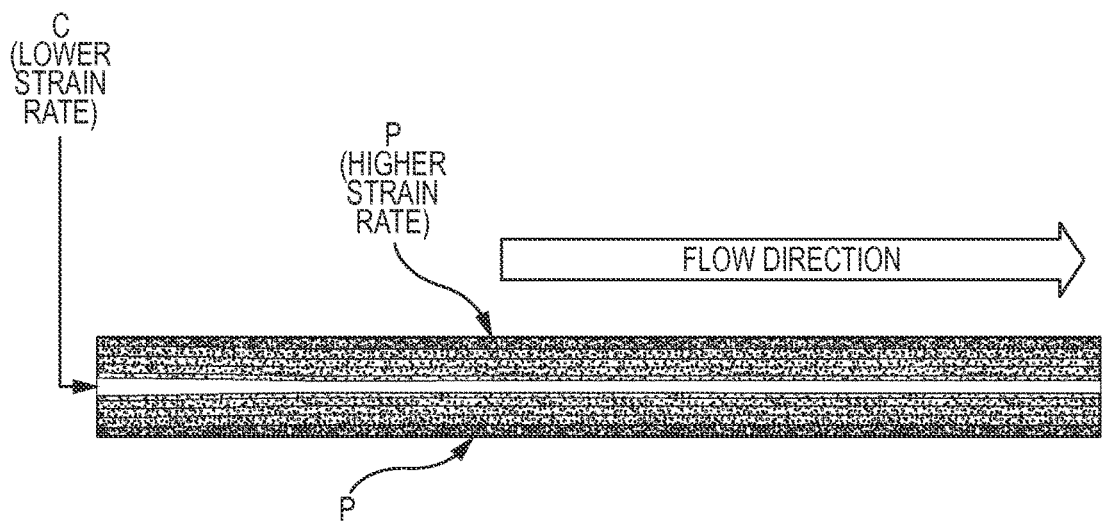

FIGS. 7 and 8 depict aspects of shear strain rate values for certain flow conditions in a flowcell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 7, the sample can have a flow rate of 0.3 µL/sec and the sheath fluid can have a flow rate of 21 µL/sec. With regard to FIG. 8, the sample can have a flow rate of 1 µL/sec and the sheath fluid can have a flow rate of 70 µL/sec. In each of these figures, it can be seen that the flow presents a lower strain value toward the center (C) and a higher strain value toward the periphery (P). Such strain values can correspond to an asymmetric flowcell configuration, in some embodiments.

As depicted in FIG. 7, according to some embodiments, the lower strain rate toward the center (C) portion of the flowstream can have a value of about 500 (1/s) or lower and the higher strain rate toward the periphery (P) of the flowstream can have a value of about 3000 (1/s) or higher. As depicted in FIG. 8, according to some embodiments, the lower strain rate toward the center (C) portion of the flowstream can have a value of about 1000 (1/s) or lower and the higher strain rate toward the periphery (P) of the flowstream can have a value of about 9000 (1/s) or higher.

Hence, it can be seen that lower sample and sheath fluid rates (e.g. FIG. 7) correspond to lower strain rates, and higher sample and sheath fluid rates (e.g. FIG. 8) correspond to higher strain rates. It is understood that embodiments of the present invention encompass the use of sample and/or sheath fluids corresponding to various viscosity values, various strain rate values, and/or various shear stress values.

Autofocus Target

With returning reference to FIG. 1, particle imaging systems can include an autofocus pattern or imaging target 44 that is fixed relative to the flowcell 22. The autofocus target 44 can be used to achieve focused images of blood fluid particles that flow through the flowcell.

Figure 9A:
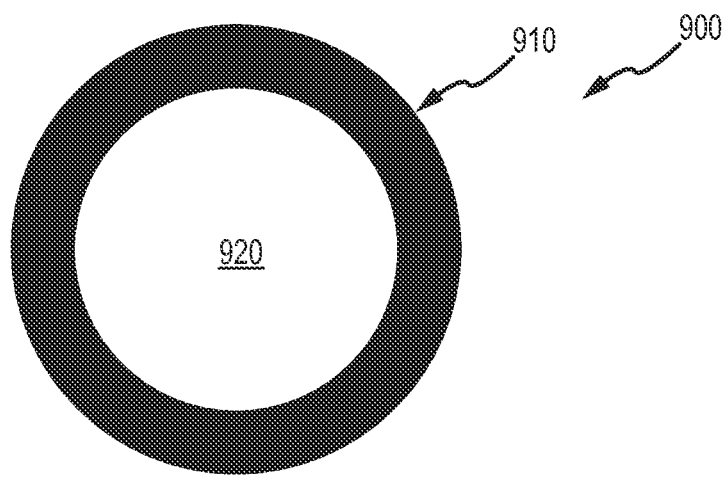
FIG. 9A depicts an exemplary autofocus target according to embodiments of the present invention.
Figure 9B:
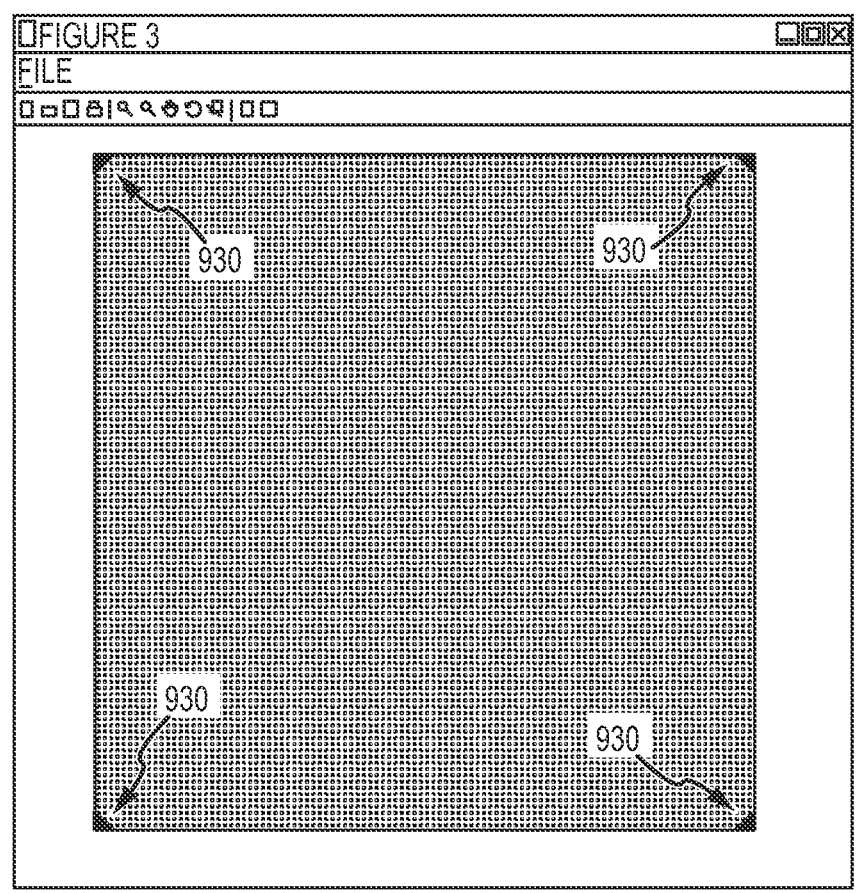
FIG. 9B shows a captured image according to embodiments of the present invention.

FIG. 9A depicts an exemplary autofocus target 900 according to embodiments of the present invention. As shown here, the target 900 includes an opaque annular band or iris 910 and a transparent center or aperture 920. In operation, the imaging device focuses on the band 910, and captures the image through the aperture. As discussed elsewhere herein, an image capture process can involve first focusing (or auto-focusing) on the band 910, and then adjusting a distance between the image capture device and the sample fluid stream prior to obtaining the image through the aperture 920. Accordingly, the band 910 can present a target upon which an auto-focus system of the image capture device can detect and focus upon, and certain portions of the target (e.g. edges or segments) can be included in the image. In some cases, the target can be provided as a chrome disc having a central aperture. An exemplary target can be provided with a central pinhole, having a diameter of about 0.5 mm, that is glued or fixed to the flowcell. The size of the central pinhole or aperture 920 can be selected so that only four edge portions 930 of the opaque annular band 910 are visible in the captured image 940, as illustrated in FIG. 9B. Hence, the annular band 910 does not interfere with the capturing of cell images (e.g. light can pass through the aperture 920 so as to illuminate the sample particles, and the field of view is substantially unimpeded by the annular band). In this way, the band 910 shows up only in the corners of the image.

Figure 11:
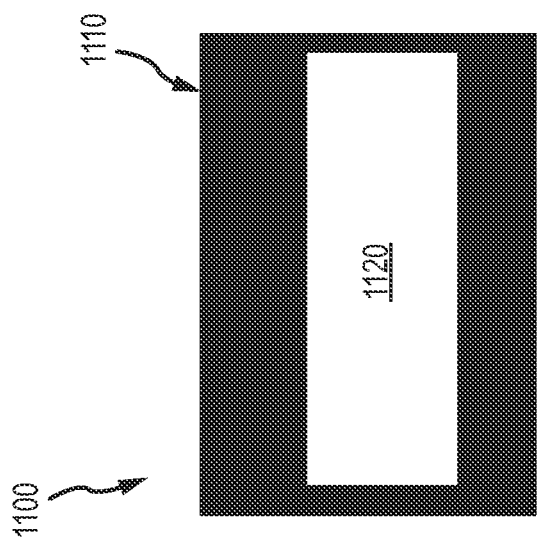
FIGS. 10 and 11 depict exemplary autofocus targets according to embodiments of the present invention.
Figure 10:
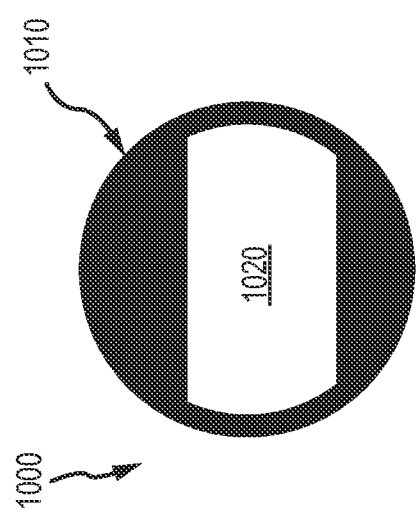

FIG. 10 depicts an exemplary autofocus or imaging target 1000 according to embodiments of the present invention. The target 1000 includes an band or border 1010 and a central aperture 1020. The band or iris 1010 can be opaque, and the aperture 1020 can be transparent. FIG. 11 shows another exemplary autofocus target 1100 according to embodiments of the present invention. The target 1100 includes a band or border 1110 and a central aperture 1120. The band or iris 1110 can be opaque, and the aperture 1120 can be transparent. According to some embodiments, the autofocus target 1100 provides an Image having 50 pixels of black on the top and the bottom. In some cases, the autofocus target 1100 provides a flowcell focus offset (FCFO) of about 65.3 µm.

Figure 12A:
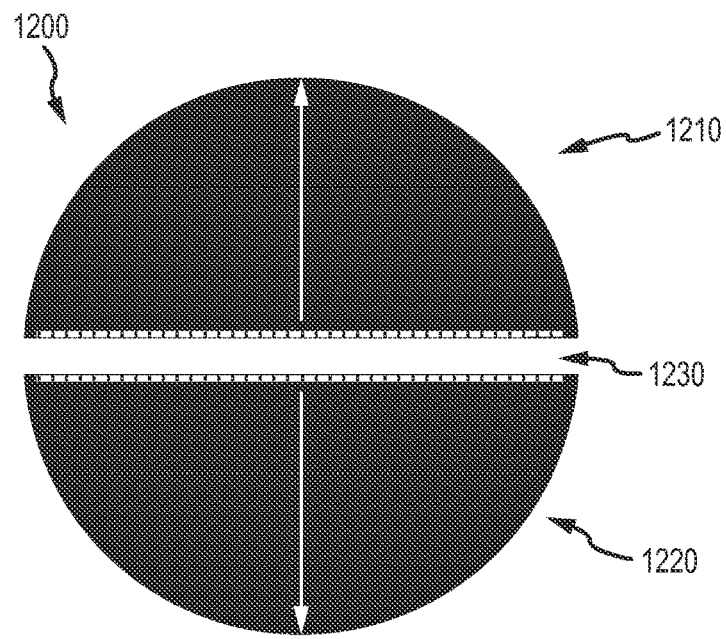
FIG. 12A depicts an exemplary autofocus target according to embodiments of the present invention.

FIG. 12A depicts an exemplary autofocus target 1200 according to embodiments of the present invention. The target 1200 is presented as a letterbox design, and includes a first or upper border 1210 and a second or lower border 1220. The target 1200 also includes an aperture or transparent passage 1230 between the first and second borders. According to some embodiments, the target has a diameter of about 4 mm, and the height of the letterbox is 265 µm. In some cases, the upper and lower borders can be present as half circles, and can be produced with a deposited metal such as chromium oxide or some other opaque material.

Figure 12B:
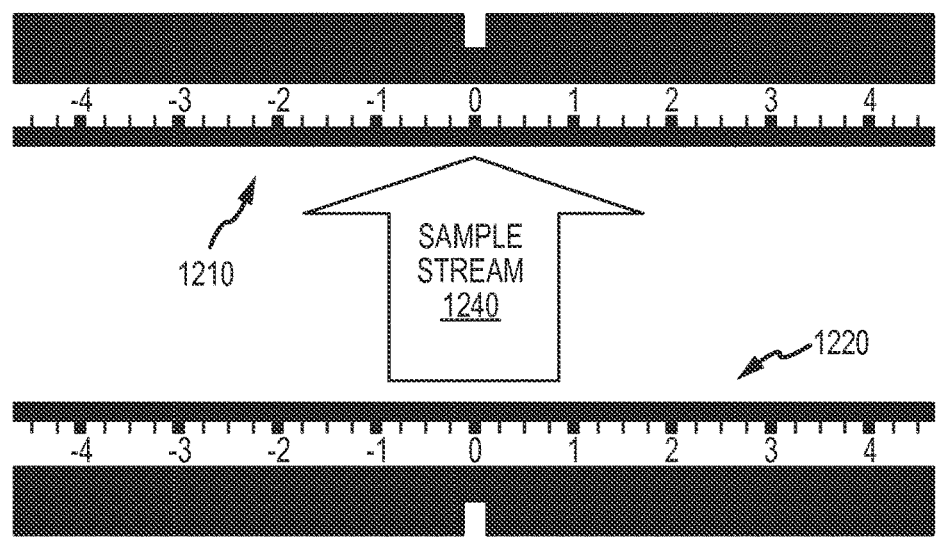
FIG. 12B shows a close-up view of the central portion of the autofocus target according to embodiments of the present invention.

FIG. 12B shows a close-up view of the central portion of the autofocus target 1200. As shown here, the first border 1210 includes a negative/positive numerical scale, with a centered zero value. The second border 1220 includes a similar scale. In some cases, the scale increments are 100 µm. According to some embodiments, the scales can be used to facilite positioning of the flow cell so that the field of view of the imaging device or camera can be centered on the sample stream. As shown here, the sample stream 1240 flows in a direction perpendicular to the scales of the first and second borders. As part of a focusing protocol, the image capture device can operate to focus on the numbers or other characters or imageable objects present on the borders 1210, 1220.

Figure 13A:
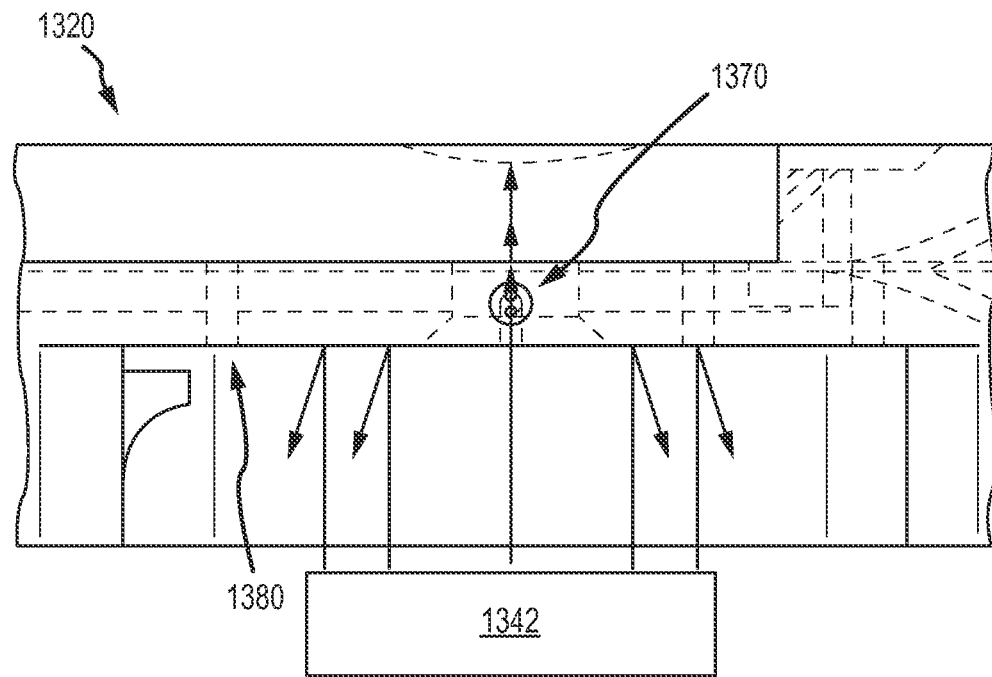
FIGS. 13A, 13B, and 13C depict views of flowcell temperature sensors according to embodiments of the present invention.
Figure 13B:
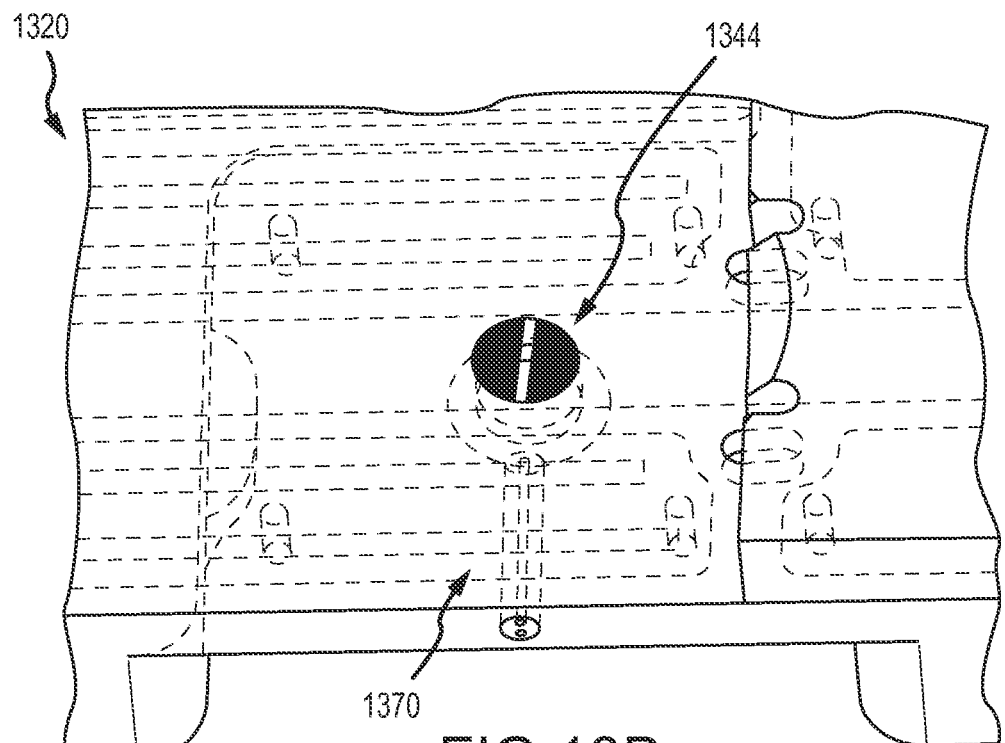

Embodiments of the present invention encompass techniques for addressing thermal drift associated with use of the particle analysis system, whereby such thermal effects may otherwise compromise the quality of images obtained with the imaging device. FIG. 13A depicts a partial side view of a flowcell 1320 having a thermal sensor 1370, a reflector 1380, and an autofocus target 1344. During operation of a particle analysis system, thermal effects may cause the sample stream to slowly drift out of focus of the imaging device. For example, thermal effects can be caused by thermal expansion of the flow cell through radiated heat coming from the lamp. Further, thermal effects can be caused by thermal expansion of the flowcell and optical bench assembly (OBA) assembly through conductive and radiative heating. In some embodiments, certain components of the OBA can expand, which may contribute to focusing errors. For example, such components may include metal plates that hold camera 24 together, a metal plate that holds or is connected to the flow cell, or a metal plate that holds both the flowcell and camera 24 together. FIG. 13B depicts a partial perspective view of flowcell 1320 having thermal sensor 1370 and autofocus target 1344. Further, FIG. 13C depicts another perspective view of flowcell 1320 having a thermal sensor 1370, reflector 1380, and autofocus target 1344.

FIG. 13B depicts a partial perspective view of flowcell 1320 having thermal sensor 1370 and autofocus or imaging target 1344. According to some embodiments of the present invention, an image capture device can be focused on the sample flowstream using a temperature that is sensed by a thermal sensor associated with the analyzer. For example, the temperature can correspond to a sample fluid temperature, a sheath fluid temperature, a flowcell temperature, or an image capture device temperature. In some cases, the temperature is a temperature at the imaging site of a flowcell. In some cases, the temperature is a temperature at a location downstream of the imaging site. In some cases, the temperature is a temperature at a location upstream of the imaging site. According to some embodiments of the present invention, an image capture device can be focused on the sample flowstream using a temperature rate of change associated with the analyzer. For example, the temperature rate of change correspond to a sample fluid temperature rate of change, a sheath fluid temperature rate of change, a flowcell temperature rate of change, or an image capture device temperature rate of change.

Figure 13C:
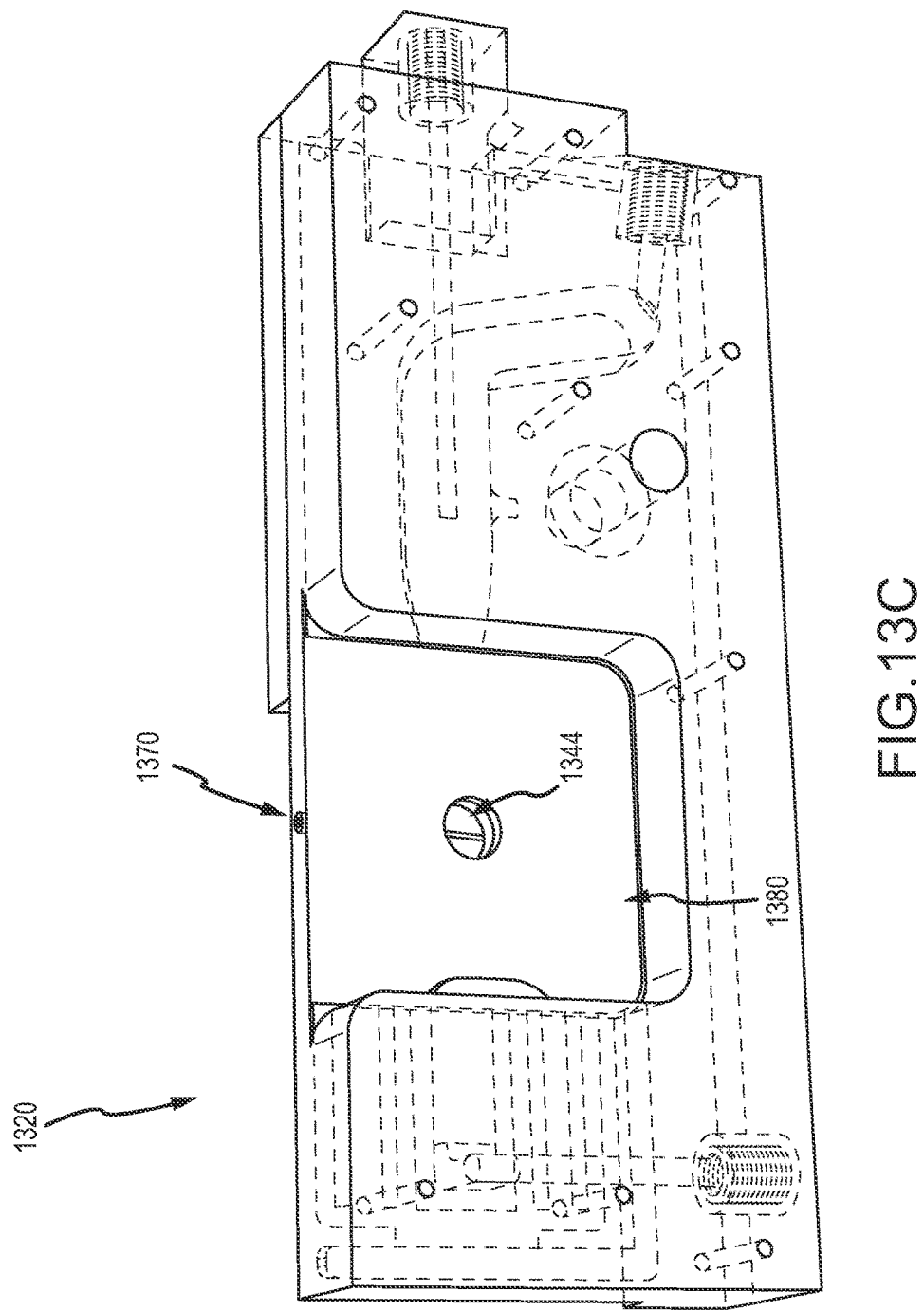

FIG. 13C depicts another perspective view of flowcell 1320 having a thermal sensor 1370, reflector 1380, and autofocus or imaging target 1344. Reflector 1380 can operate to reduce or limit the amount of heat absorbed by flowcell 1320. For example, reflector 1380 can block heat radiated by a flash lamp 1342 as indicated in FIG. 13A. Hence, reflector 1380 can minimize the thermal impact of the lamp. Reflector 1342 can also reduce glare and light scatter generated by the lamp, thus resulting in improved image quality. Thermal sensor 1370 is positioned near the fluid flow channel and adjacent to the image capture site, so that accurate temperature readings can be obtained. Information from the temperature sensor can be used to focus the image capture device on the sample fluid ribbon stream. Exemplary autofocusing techniques disclosed herein can be based on temperature fluctuations occurring within certain elements of the analyzer.

According to some embodiments, a method for imaging particles in a blood fluid sample may include flowing a sheath fluid along a flowpath of a flowcell, and injecting the blood fluid sample into the flowing sheath fluid within the flowcell so that the blood fluid sample flows in a sample flowstream with a flowstream width greater than a flowstream thickness, such that the flowcell has an associated temperature. Further, the method may include focusing an image capture device, along an imaging axis, on the flowstream to a first focal state while the temperature associated with the flowcell is at a first temperature, and acquiring a first focused image of a first subset of the particles within the flowstream with the image capture device at the first focal state. What is more, the method may include determining that the temperature associated with the flowcell has undergone a change from the first temperature to a second temperature, and automatically adjusting focus of the image capture device from the first focal state to a second focal state in response to the change in temperature and a known relationship between flowcell temperature and desired focus. Still further, the method may include acquiring a second focused image of a second subset of the particles within the flowstream with the image capture device at the second focal state.

In some cases, the process of adjusting focus of the image capture device includes adjusting a distance between the image capture device and the flowcell using the change in temperature and the known relationship between flowcell temperature and desired focus. In some cases, the process of adjusting focus of the image capture device includes adjusting a focal distance of the image capture device using the change in temperature and the known relationship between flowcell temperature and desired focus.

Focused Images

Figures 14A, 14B:
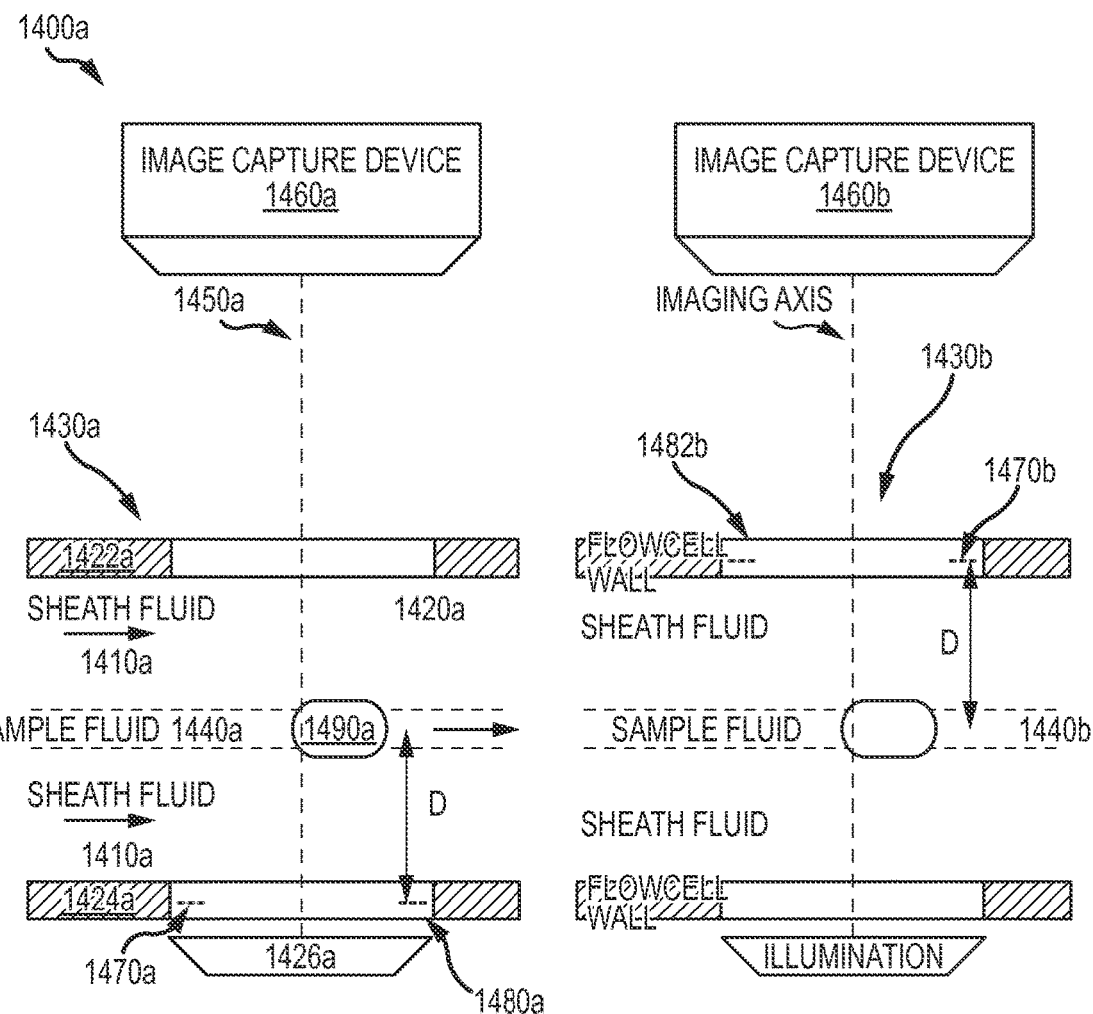
FIGS. 14A and 14B provide cross-section side views that illustrate aspects of focusing systems and methods, according to embodiments of the present invention.

FIGS. 14A and 14B provide cross-section side views that illustrate aspects of imaging systems and methods, according to embodiments of the present invention. With reference to FIG. 14A, a particle analysis system 1400a such as a hematology analyzer can be configured for combined viscosity and geometric hydrofocusing, for example using flowcell and viscous sheath fluid techniques such as those described in co-pending U.S. patent application Ser. Nos. 14/216,533 and 14/215,834, both filed Mar. 17, 2014, the contents of which are incorporated herein by reference. An exemplary method for imaging particles in a blood fluid sample using the particle analysis system can include flowing a sheath fluid 1410a along a flowpath 1420a of a flowcell 1430a of the particle analysis system. The flowpath 1420a can be defined at least in part by opposing flowcell walls 1422a, 1424a of the flowcell. The sheath fluid 1410a can have a viscosity that is different from a viscosity of the blood fluid sample. The imaging method can further include injecting the blood fluid sample into the flowing sheath fluid 1410a within the flowcell 1430a so that the blood fluid sample fluid flows in a sample flowstream 1440a. The sample flowstream 1440a can have a flowstream width greater than a flowstream thickness. The sample flowstream 1440a can also flow through a decrease in flowpath size and traverse an imaging axis 1450a. In the FIG. 14A illustration, the direction of flow is from the left to the right.

Additionally, the imaging method can include focusing an image capture device 1460a by imaging an imaging target 1470a having a position fixed relative to the flowcell 1430a. For example, as depicted here, the imaging target 1470a can have a position fixed relative to an illumination window 1480a of the flowcell. In some cases, the imaging target 1470a can be embedded within or fixed upon the window 1480a. Methods can also include acquiring a focused image of the particles of the sample fluid (e.g. particle 1490a, disposed at least partially within the flowstream 1440a) with the image capture device 1460a. The focused image is suitable for particle characterization and counting.

The image capture device 1460a can be focused on the sample flowstream 1440a using a displacement distance. For example, the displacement distance can correspond to a distance D between the sample flowstream 1440a and the imaging target 1470a. The viscosity difference between the sheath fluid 1410a and blood fluid sample, in combination with the decrease in flowpath size, is effective to hydrofocus the sample fluid in the sample flowstream 1440a at the imaging axis 1450a while retaining viability of cells in the blood fluid sample. For example, a viscosity hydrofocusing effect induced by an interaction between the sheath fluid 1410a and the sample fluid stream 1440a associated with the viscosity difference, in combination with a geometric hydrofocusing effect induced by an interaction between the sheath fluid 1410a and the sample fluid stream 1440a associated with the reduction in flowpath size, can be effective to provide a target imaging state in at least some of the fluid sample particles at the imaging axis 1450a while a viscosity agent in the sheath fluid 1410a retains viability of cells in the sample fluid stream 1440a leaving structure and content of the cells intact when the cells extend from the sample fluid stream 1440a into the flowing sheath fluid 1410a.

As the image capture device 1460a is focused on the sample flowstream 1440a using the displacement distance, the image capture device 1460a can obtain images of particles or cells within the sample flowstream 1440a at the imaging axis 1450a, or at an image capture site associated with the imaging axis 1450a. In some cases, the particles can be illuminated with an illumination source or lamp 1426a. Images of the sample flowstream 1440a can be obtained as particles approach the imaging axis 1450a, as the particles traverse the imaging axis 1450a, and/or as the particles flow away from the imaging axis 1450a.

FIG. 14B depicts aspects of an alternative flowcell configuration, where the imaging target 1470b has a position fixed relative to a viewport window 1482b of the flowcell 1430b. For example, the imaging target 1470b can be embedded within or fixed upon the window 1482b. As shown here, the imaging method can include focusing an image capture device 1460b by imaging an imaging target 1470b having a position fixed relative to the flowcell 1430b. Further, the image capture device 1460b can be focused on the sample flowstream 1440b using a displacement distance. For example, the displacement distance can correspond to a distance D between the sample flowstream 1440b and the imaging target 1470b.

Figure 14C:
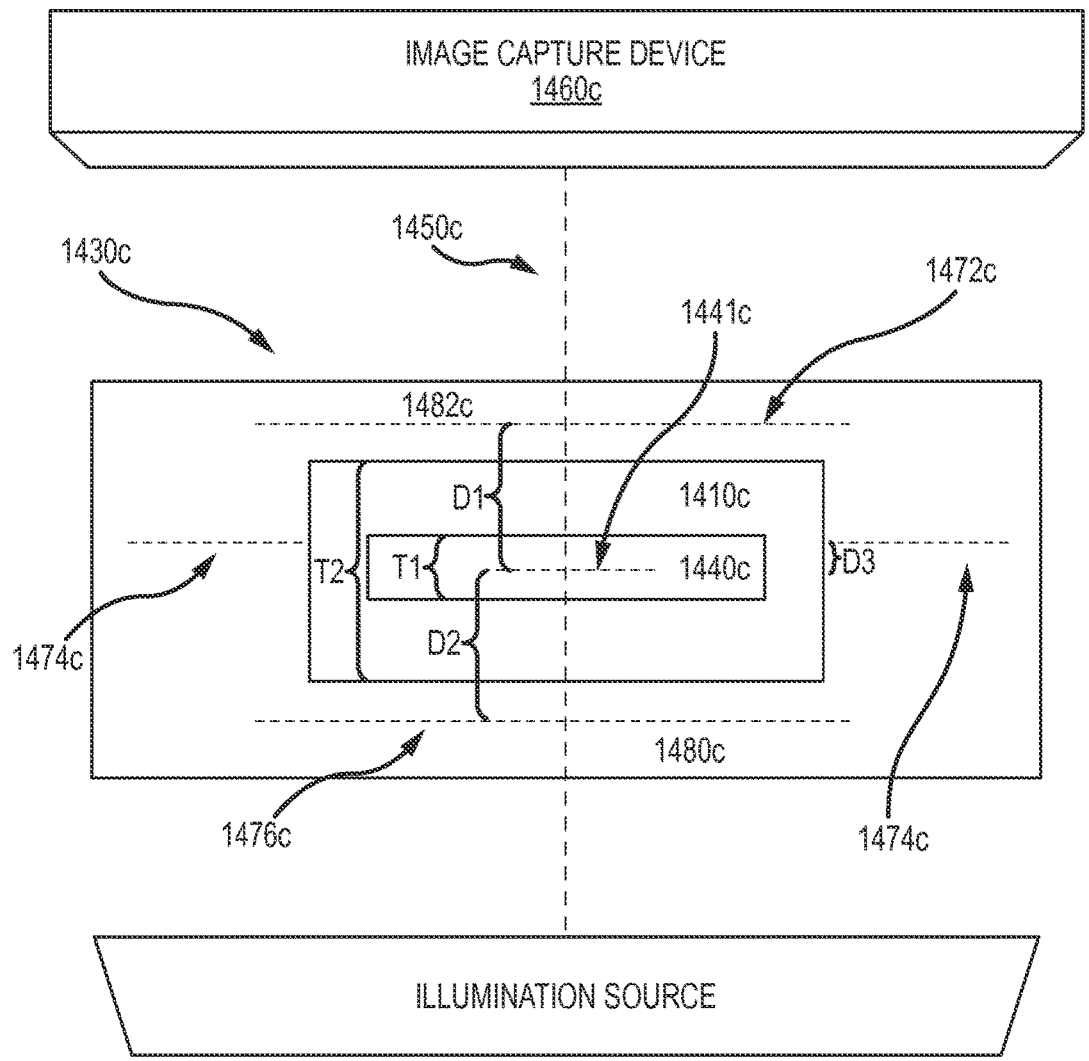
FIG. 14C depicts a cross-section side view of a flowcell illustrating aspects of focusing systems and methods, according to embodiments of the present invention.

FIG. 14C depicts a cross-section end view of a flowcell 1430c, illustrating various alternative placement locations for an autofocus or imaging target. For example, an imaging target 1472c can be located at a viewport window 1482c of the flowcell 1430c. Optionally, an imaging target 1474c can be located at an illumination window 1480c of the flowcell 1430c. Further optionally, an imaging target 1476c can be located in a lateral flowcell wall (e.g. 1432c and/or 1434c). The image capture device 1460c can be focused on a sample flowstream 1440c, which is enveloped within a sheath fluid 1410c, a using the displacement distance. In some embodiments, the displacement distance can correspond to or be defined by a distance D1 along the imaging axis 1450c between the sample flowstream 1440c (or a central plane 1441c defined by the flowstream 1440c) and the viewport window imaging target 1472c. In some embodiments, the displacement distance can correspond to or be defined by a distance D2 along the imaging axis between the sample flowstream 1440a (or the central plane 1441c) and the illumination window imaging target 1476c. In some embodiments, the displacement distance can correspond to or be defined by a distance D3 along the imaging axis between the sample flowstream 1440a (or the central plane 1441c) and the flowcell lateral wall imaging target 1474c. In some cases, distance D3 has a value greater than zero. In some cases, distance D3 has a value of zero; that is, where the sample flowstream 1440a (or the central plane 1441c) is coplanar with the imaging target 1474c. In some cases, it is possible to define a displacement distance that is not calculated based on distance D1, distance D2, or distance D3. For example, a displacement distance may be a predetermined number or value that is provided by a flowcell or hematology analyzer manufacturer.

According to some embodiments, the sample flowstream 1440c can have a thickness T1 at the imaging axis within a range from about 2 µm to about 10 µm. In some cases, the flowpath or the sheath fluid 1410c can have a thickness T2 of about 150 µm at the imaging axis. As shown here, an imaging target 1472c can be located on a viewport window 1482c disposed between the sample flowstream 1440c and the image capture device 1460c. In some cases, an imaging target (e.g. 1474c) can be located between an illumination window 1480c and a viewport window 1482c. As discussed elsewhere herein, the process of acquiring a focused image can include adjusting a distance between the image capture device 1460c and the flowcell 1430c using the displacement distance. In some cases, as discussed elsewhere herein, the process of acquiring a focused image can include adjusting a focal distance of the image capture device 1460c using the displacement distance. In some cases, the process of acquiring a focused image can include adjusting the distance between the image capture device 1460c and the flowcell 1430c, and the process of adjusting the distance includes moving the flowcell 1430c, for example to a position closer to the image capture device 1460c, or to a position more distant from the image capture device 1460c.

Figure 14D:
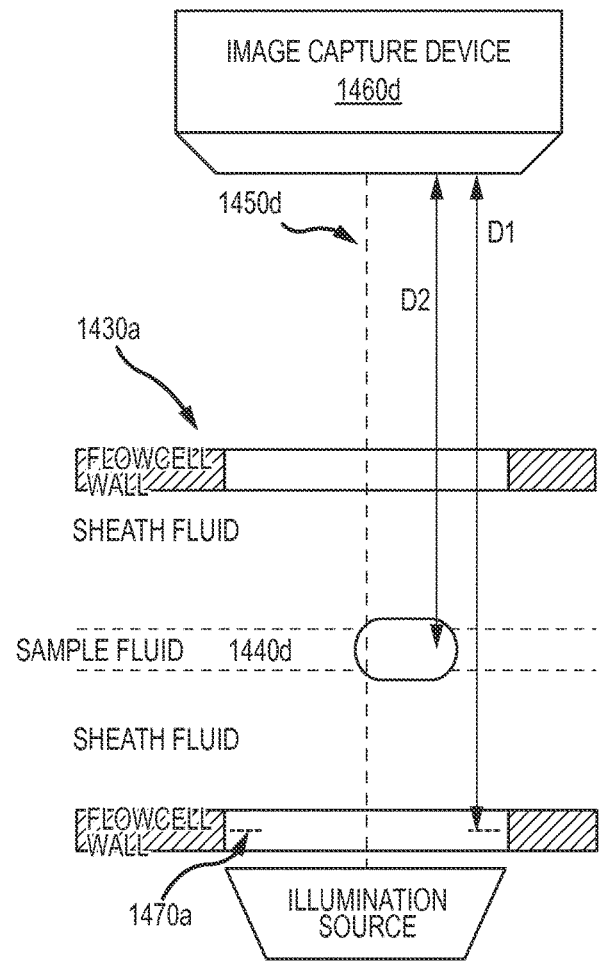
FIG. 14D provides a cross-section side view that illustrates aspects of focusing systems and methods, according to embodiments of the present invention.

As depicted in FIG. 14D, a first focal distance of the image capture device 1460d can correspond to a distance D1 (e.g. along the imaging axis 1450d) between the image capture device 1460d and the imaging target 1470d, and a second focal distance of the image capture device 1460d can correspond to a distance D2 (e.g. along the imaging axis 1450d) between the image capture device 1460d and the sample flow stream 1440d (or a central plane defined by the sample flow stream). In some cases, the imaging target may be located in another location in the flowcell, for example as depicted in FIG. 14C. According to some embodiments, the displacement distance can correspond to a distance difference between the first focal distance (or distance D1) and the second focal distance (or distance D2). The image capture device 1460d can be focused on the sample flowstream 1440d using this displacement distance (e.g. difference between D1 and D2).

FIG. 15 depicts an elevation view showing embodiments of an autofocus pattern (or imaging target), which for example can be located on illuminating orifices or window, on a viewing portal or window, or at another flowcell location. The target can fade as the distance or position of the high optical resolution imaging device is moved relative to the ribbon-shaped sample stream. As depicted in FIGS. 9-12B, an imaging or focus target (autofocus pattern) can reside on the periphery of the area of view in which the sample is to appear. With returning reference to FIG. 15, it can be seen that it is also possible that the focus target can be defined by contrasting shapes that reside in the field of view.

Figure 16A:
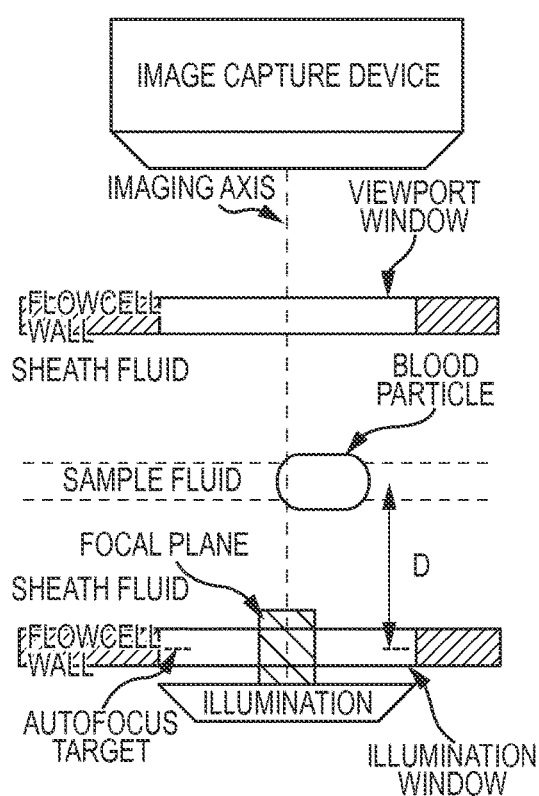
FIGS. 16A and 16B show aspects of focusing systems and methods, according to embodiments of the present invention.

When the imaging device is in focus on the autofocus pattern (target) (panel B in FIG. 15), the shapes as imaged by the device are well defined and can be used for autofocusing as described herein, namely to seek the distance between the target and the imaging device at which the shapes produce the highest contrast in amplitude between adjacent pixels located along lines that cross over the shapes, such as the lines shown as arrow heads. The focus configuration depicted in panel B corresponds to an analogous focus configuration depicted in FIG. 16A. As illustrated in FIG. 16A, the focal plane of the image capture device is aligned with the autofocus target, and hence the image capture device is in a position to obtain sharp images of the autofocus target.

Figure 16B:
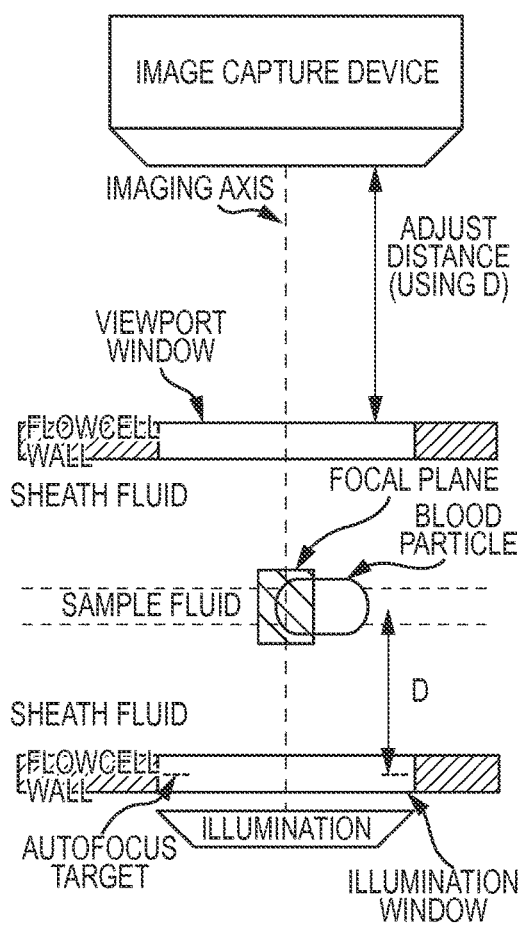

With returning reference to FIG. 15, when the working location (e.g. focal plane of imaging device) is moved away from the autofocus pattern (shown in panels A and C, shown left and right of autofocus pattern in FIG. 15), for example by adjusting the working distance of the objective or the distance between the objective and its focal plane, the focus target shapes now go out of focus, and at the position where the high optical resolution imaging device is focused on the ribbon-shaped sample stream, the focus target shapes are no longer discernable at all (see panel D in FIG. 15). The focus configuration depicted in panel D can corresponds to an analogous focus configuration depicted in FIG. 16B. As illustrated in FIG. 16B, the focal plane of the image capture device is aligned with the sample fluid stream, and hence the image capture device is in a position to obtain sharp images of particles in the sample flowstream. The focal plane of FIG. 16A is separated from the focal plane of FIG. 16B by a distance D. As shown in FIG. 16B, by moving the image capture device a distance D it is possible to also move the focal plane a distance D, and hence move the focal plane from the autofocus target to the sample flowstream. In some cases, the focal plane can be moved from the autofocus target to the sample flowstream by internally adjusting the focal distance of the image capture device while keeping the image capture device in a fixed position relative to the flowcell. In some cases, the focal plane can be moved from the autofocus target to the sample flowstream by internally adjusting the focal distance of the image capture device in combination with adjusting the position of the image capture device relative to the flowcell. The autofocus shapes can be provided at any location that is within view and is fixed relative to the flowcell, such as on the illumination opening or window, or on the front or back of the viewing port or window through which the high optical resolution imaging device is directed, or at a fixture attached to the photocell to hold a target in position to be imaged.

According to some embodiments, when the high optical resolution imaging device is moved over the displacement distance and the autofocus pattern goes out of focus, the features that appear in focus are the blood cells as opposed to the autofocus pattern. In the embodiment of FIG. 15, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for hematology (blood cell) imaging applications. In some embodiments, the autofocus feature maintains the high optical resolution imaging device within 1 µm of the optimal focus distance.

Accordingly, the features described in FIG. 15 provide an exemplary technique for determining a displacement distance. For example, a method of determining a displacement distance may include an autofocusing process that involves injecting a test fluid sample into a sheath fluid to form a test sample flowstream within a flow cell, and obtaining a first focused image of the imaging target using an image capture device. The first focused image can correspond to panel B in FIG. 15, where the focused imaging target and the image capture device define a first focal distance. As depicted here, the focal plane or working distance/location of the image capture device is positioned at the imaging target. The autofocusing process can also include obtaining a second focused image of the test sample flowstream using the image capture device. The second focused image can correspond to panel D in FIG. 15, where the focused test sample flow stream and the image capture device define a second focal distance. As depicted here, the focal plane or working distance/location of the image capture device is positioned at the imaging target. The autofocusing procees may further include obtaining the displacement distance by calculating a difference between the first focal distance and the second focal distance. In some cases, the test fluid sample is the same as the blood fluid sample and the test sample flowstream is the same as the sample flowstream. In some cases, the autofocusing process establishes a focal plane associated with the image capture device, and the focal plane remains stationary relative to the image capture device. In some cases, the process of autofocusing the image capture device includes determining an optimal focus position from among a plurality of focus positions.

According to some embodiments, the image capture device can be focused on the sample flowstream without using temperature data. For example, a process of focusing the image capture device on the sample flowstream can be performed independently of a temperature of the image capture device. In some cases, an imaging target can include a scale (e.g. as depicted in FIG. 12B) for use in positioning the imaging axis of the image capture device relative to the sample flowstream. In some cases, the imaging target can include an iris aligned relative to the imaging axis, such that the imaged particles are disposed within an aperture defined by the iris, and one or more edge portions of the iris are imaged during autofocusing.

In exemplary embodiments, autofocusing techniques can position the flowcell to within ±1 µm from an optimal focal position of the sample stream. In some cases, embodiments encompass autofocus techniques that can automatically focus the imaging system without the need for a separate focusing liquid or solution or any user intervention. Exemplary autofocusing techniques can also acount for mechanical causes of suboptimal focusing performance, such as drift or thermal expansion which can cause fluctuations in the distance between the imaging device objective and flowcell. In some cases, it was observed that the location of the sample flow within the flowcell can be very stable and temperature independent. Hence, exemplary imaging techniques can involve focusing on an imaging target in the flowcell, and using a fixed offset to achieve optimal focus on the sample stream.

According to some embodiments, the microscope objective that is used on an imaging system has a numerical aperture of 0.75, resulting in a theoretical depth of field (DoF) of ±0.5 µm. In certain experimental trials, it was observed that good image quality could be obtained at ±1.25 µm from an optimal focal point. It was also observed that a practical or experimental depth of field could be different from the theoretical depth of field. For example, in certain experimental trials it was observed that the depth of field was around 2.5 to 3 µm. Based on certain experimental studies, it was determined that autofocus performance for positioning the flowcell within ±1.25 µm could ensure good image quality. In some embodiments, an autofocus system can operate to position the flowcell within ±1 μm from an optimal focus position of the sample stream. In certain experimental trials, it was observed that autofocus techniques as disclosed herein can repeatedly locate a target in a flowcell with a standard deviation of less than 0.3 μm. In some cases, trial autofocus system runs demonstrated excellent repeatability (standard deviation ≤0.23 μm) and were able to determine the focus position of the sample stream to within <0.6 μm from an optimized metric position which is within a ±1 μm positional tolerance. Additional autofocus trial runs at a variety of temperature conditions also exhibited excellent positioning performance (e.g. flowcell positioning within a required ±1 μm tolerance of and optimal focus position). This degree of accuracy in an automated analyzer system is well suited for consistently and reliably obtaining high quality images of particles from a blood fluid sample flowing in a thin ribbon flowstream as disclosed elsewhere herein, over an operational temperature range corresponding to standard laboratory conditions.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A particle analysis system that performs geometric hydrofocusing for imaging particles in a blood fluid sample, the system comprising:
   a flowcell having a flowpath with an injection tube and an imaging window with an imaging axis therethrough, the flowpath of the flowcell having a decrease in flowpath size comprising a narrowing zone, the flowcell comprises an illumination window on a first wall and a viewport window on a second wall, wherein the illumination window is placed opposite to the viewport window;
   a sheath fluid input in fluid communication with the flowpath;
   a blood fluid input in fluid communication with the injection tube, wherein the blood fluid input injects the blood fluid sample into the flowing sheath fluid within the flowcell at the narrowing zone of the flowpath so that the blood fluid sample enters the flowing sheath fluid and is compressed at the narrowing zone, flowing in a sample flowstream with a flowstream width greater than a flowstream thickness;
   an image capture device comprising an objective lens, the viewport window is positioned between the image capture device and the illumination window on an imaging axis of the image capture device, wherein the image capture device is configured to image a blood fluid sample particle in the blood fluid sample;
   a flowcell control mechanism, the flow cell control mechanism provided to vary to distance between the flowcell and the objective lens;
   an autofocus pattern having a position fixed relative to the flowcell, the autofocus pattern having a transparent portion that admits light, an opaque border around the transparent portion, and a high contrast pattern having sharply contrasting features and edges, the autofocus pattern and the sample flowstream defining a displacement distance along the imaging axis; wherein the autofocus pattern is located between the illumination window and the viewport window, and
   a data processing module in connectivity with the image capture device and with the flowcell control mechanism, the data processing module comprising a processor and a tangible non-transitory computer readable medium,
   the computer readable medium programmed with a computer application that, when executed by the processor, (i) determines a focus position of the autofocus pattern to generate a focused image, (ii) causes the flowcell control mechanism to adjust the position of the flowcell relative to the objective lens of the image capture device, based on the displacement distance in order to focus the imaging device on the sample flowstream, so that the sample flowstream at the imaging axis is aligned with a focal plane of the objective lens of the image capture device, (iii) causes the image capture device to acquire an image of the blood fluid sample particle, suitable for particle characterization and counting, after the flowcell control mechanism has adjusted the position of the flowcell, and (iv) causes the system to inject a test fluid sample into the sheath fluid to form a test sample flowstream within the flow cell, causes the image capture device to obtain a first focused image of the autofocus pattern, where the focused autofocus pattern and the image capture device define a first focal distance, causes the image capture device to obtain a second focused image of the test sample flowstream, where the focused test sample flow stream and the image capture device define a second focal distance, and causes the system to obtain the displacement distance by calculating a difference between the first focal distance and the second focal distance.

2. The system of claim 1, wherein the particle analysis system is configured for combined viscosity and geometric hydrofocusing, wherein the sheath fluid has a sheath fluid viscosity that differs from the sample fluid viscosity by a viscosity difference in a predetermined viscosity difference range, and wherein the viscosity difference between the sheath fluid and blood fluid sample, in combination with the decrease in flowpath size, is effective to hydrofocus the sample flowstream at the imaging axis while a viscosity agent in the sheath fluid retains viability of cells in the sample flowstream leaving structure and content of the cells intact when the cells extend from the sample flowstream into the flowing sheath fluid.

3. The system of claim 1, wherein the autofocus pattern is located on a viewport window disposed between the sample flowstream and the image capture device.

4. The system of claim 1, wherein the computer application, when executed by the processor, causes the system to detect an autofocus re initiation signal, and to repeat auto-focusing and image acquisition steps in response to the auto-focus re-initiation signal.

5. The system of claim 1, wherein the autofocus pattern comprises a scale for use in positioning the imaging axis of the image capture device relative to the sample flowstream.

6. The system of claim 1, wherein the autofocus pattern comprises an iris aligned relative to the imaging axis, such that the imaged particles are disposed within an aperture defined by the iris.

7. The system of claim 1, wherein the image capture device comprises a digital microscope camera.

8. The system of claim 1, wherein the image capture device comprises an optical resolution imaging device having an optical resolution of no greater than 1 µm.

9. The system of claim 1, wherein the image capture device has a depth of field between 1 µm and 4 µm.

10. The system of claim 1, wherein the image capture device comprises a camera having a depth of field between 2 µm and 10 µm and the sample flowstream has a thickness between 2 µm and 10 µm.

11. The system of claim 1, wherein the image of the blood fluid sample particle comprises in-focus cellular contents of the blood fluid sample particle.

12. The system of claim 1, wherein the image of the blood fluid sample particle comprises an in-focus organelle of the blood fluid sample particle.

13. The system of claim 1, wherein the image capture device comprises a camera having a focal plane, wherein the focal plane of the camera extends across the imaging target before the flowcell control mechanism has adjusted the position of the flowcell thereby enabling an in-focus image of the autofocus pattern, and wherein the focal plane of the camera extends across the sample stream after the flowcell control mechanism has adjusted the position of the flowcell thereby enabling an in-focus image of the blood fluid sample particle.

14. The system of claim 1, wherein the displacement distance is adjustable via moving a zoom lens of the image capture device or a mirror of the image capture device.

\* \* \* \* \*